US008148572B2

(12) United States Patent
Luker et al.

(10) Patent No.: US 8,148,572 B2
(45) Date of Patent: Apr. 3, 2012

(54) COMPOUNDS

(75) Inventors: Timothy Jon Luker, Loughborough (GB); Rukhsana Tasneem Mohammed, Loughborough (GB); Stephen Thom, Loughborough (GB); Anil Patel, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 498 days.

(21) Appl. No.: 12/089,275

(22) PCT Filed: Oct. 5, 2006

(86) PCT No.: PCT/GB2006/003689
§ 371 (c)(1),
(2), (4) Date: Apr. 4, 2008

(87) PCT Pub. No.: WO2007/039736
PCT Pub. Date: Apr. 12, 2007

(65) Prior Publication Data
US 2009/0192163 A1    Jul. 30, 2009

(30) Foreign Application Priority Data

Oct. 6, 2005  (GB) .................................. 0520323.7
Apr. 27, 2006 (GB) .................................. 0608299.4

(51) Int. Cl.
C07C 62/00 (2006.01)
C07C 63/00 (2006.01)
C07C 59/00 (2006.01)
(52) U.S. Cl. ..................... 562/466; 562/405; 562/465
(58) Field of Classification Search .................. 562/466, 562/405, 465
See application file for complete search history.

(56) References Cited

U.S. PATENT DOCUMENTS

| 3,278,524 | A |   | 10/1966 | Johnson et al. |
|---|---|---|---|---|
| 3,920,846 | A |   | 11/1975 | Hanauye et al. |
| 3,985,779 | A | * | 10/1976 | Tanaka et al. ............... 556/183 |
| 4,234,742 | A |   | 11/1980 | Cognacq et al. |
| 4,248,618 | A |   | 2/1981 | Serban et al. |
| 4,670,566 | A |   | 6/1987 | Walsh et al. |
| 5,006,542 | A |   | 4/1991 | Hall et al. |
| 5,145,790 | A |   | 9/1992 | Mattingly et al. |
| 5,411,972 | A |   | 5/1995 | Komoto et al. |
| 5,413,891 | A |   | 5/1995 | Matsuura et al. |
| 5,532,371 | A |   | 7/1996 | Komoto et al. |
| 5,703,099 | A |   | 12/1997 | Hamanaka et al. |
| 6,150,413 | A |   | 11/2000 | Bernardon et al. |
| 6,376,546 | B1 |   | 4/2002 | Shoda et al. |
| 6,417,212 | B1 |   | 7/2002 | Brooks et al. |
| 7,056,942 | B2 |   | 6/2006 | Hildesheim et al. |
| 7,067,507 | B2 |   | 6/2006 | Pullet et al. |
| 7,737,135 | B2 |   | 6/2010 | Luker et al. |
| 2004/0029933 | A1 |   | 2/2004 | Zhao et al. |
| 2004/0097555 | A1 |   | 5/2004 | Ohkawa et al. |
| 2004/0220237 | A1 |   | 11/2004 | Fu et al. |
| 2005/0239881 | A1 |   | 10/2005 | Dunn et al. |
| 2006/0211765 | A1 |   | 9/2006 | Pairaudeau et al. |
| 2006/0264435 | A1 |   | 11/2006 | Bonnert et al. |
| 2006/0293352 | A1 |   | 12/2006 | Bonnert et al. |
| 2007/0249686 | A1 |   | 10/2007 | Bonnert et al. |
| 2008/0114002 | A1 |   | 5/2008 | Bonnert et al. |
| 2008/0132480 | A1 |   | 6/2008 | Luker et al. |
| 2008/0255150 | A1 |   | 10/2008 | Luker |
| 2008/0293775 | A1 |   | 11/2008 | Bonnert et al. |
| 2009/0012151 | A1 |   | 1/2009 | Bonnert et al. |
| 2009/0036535 | A1 |   | 2/2009 | Luker et al. |
| 2009/0149448 | A1 |   | 6/2009 | Alcaraz et al. |
| 2009/0192163 | A1 |   | 7/2009 | Luker et al. |
| 2010/0160285 | A1 |   | 6/2010 | Luker et al. |

FOREIGN PATENT DOCUMENTS

| CH | 432119 | 9/1967 |
|---|---|---|
| EP | 0006789 | 1/1980 |
| EP | 0114734 | 8/1984 |
| EP | 0455058 | 11/1991 |
| EP | 0540165 | 5/1993 |
| EP | 0622690 | 11/1994 |
| EP | 0622816 | 11/1994 |
| EP | 0839808 | 5/1998 |
| EP | 1012142 | 6/2000 |
| EP | 1170594 | 1/2002 |
| EP | 1211513 | 6/2002 |
| EP | 1471057 | 10/2004 |
| GB | 690816 | 4/1953 |
| GB | 1 356 834 | 6/1974 |
| GB | 1 464 977 | 2/1977 |
| GB | 1 469 687 | 4/1977 |
| GB | 2 031 408 | 4/1980 |
| GB | 2 041 363 | 9/1980 |
| GB | 1 585 963 | 3/1981 |
| JP | 07140725 | 6/1995 |
| JP | 2003-508389 | 3/2003 |
| JP | 2006-521382 | 9/2006 |
| JP | 2006-522117 | 9/2006 |
| WO | WO 93/12086 | 6/1993 |
| WO | WO 97/08126 | 3/1997 |
| WO | WO98/03164 | * 1/1998 |

(Continued)

OTHER PUBLICATIONS

Alfred Burger, Isosterism and Bioisosterism in Drug Design, in Progress in Drug Research 287-328 (Ernst Jucker, ed., Birkhauser Verlag, 1991).*
George Patani & Edmond LaVoie, Bioisosterism: A Rational Approach in Drug Design, 96 Chem. Rev. 3147 (1996).*
Amin et al., "The Fries Reaction: Part VI—the rearrangement of aryl p-toluene-sulphonates & a convenient method for synthesis of hydroxy-diarylsulphones", *Journal of Scientific Industrial Research*, vol. 13B, 1954, pp. 181-183.
Atkinson et al., "Substituted (2-Phenoxyphenyl)acetic Acids with Antiinflammatory Activity", *J. Med. Chem.*, vol. 26, 1983, pp. 1353-1360.

(Continued)

*Primary Examiner* — Karlheinz R Skowronek
*Assistant Examiner* — Sean Basquill

(57) ABSTRACT

The invention relates to substituted phenylacetic acids as useful pharmaceutical compounds for treating respiratory disorders, pharmaceutical compositions containing them, and processes for their preparation.

12 Claims, No Drawings

FOREIGN PATENT DOCUMENTS

| WO | WO 99/11605 | 3/1999 |
|---|---|---|
| WO | WO 99/11627 | 3/1999 |
| WO | WO 01/16120 | 3/2001 |
| WO | WO 01/60807 | 8/2001 |
| WO | WO 01/81312 | 11/2001 |
| WO | WO 01/92224 | 12/2001 |
| WO | WO 03/064387 | 8/2003 |
| WO | WO 03/066047 | 8/2003 |
| WO | WO 03/068744 | 8/2003 |
| WO | WO 03/097042 | 11/2003 |
| WO | WO 03/097598 | 11/2003 |
| WO | WO 03/101961 | 12/2003 |
| WO | WO 2004/007451 | 1/2004 |
| WO | WO 2004/048314 | 6/2004 |
| WO | WO 2004/058164 | 7/2004 |
| WO | WO2004/058164 * | 7/2004 |
| WO | WO 2004/089884 | 10/2004 |
| WO | WO 2004/089885 | 10/2004 |
| WO | WO 2004/094386 | 11/2004 |
| WO | WO 2004/096777 | 11/2004 |
| WO | WO 2005/018529 | 3/2005 |
| WO | WO 2005/044260 | 5/2005 |
| WO | WO 2005/105727 | 11/2005 |
| WO | WO 2005/115382 | 12/2005 |
| WO | WO 2006/005909 | 1/2006 |
| WO | WO 2006/021759 | 3/2006 |
| WO | WO 2006/037982 | 4/2006 |
| WO | WO 2006/056752 | 6/2006 |
| WO | WO 2006/125596 | 11/2006 |
| WO | WO 2007/039736 | 4/2007 |
| WO | WO 2007/039741 | 4/2007 |
| WO | WO 2007/052023 | 5/2007 |
| WO | WO 2007/068894 | 6/2007 |

OTHER PUBLICATIONS

Baliah et al., "Fries rearrangement of the benzenesulphonates of xylenols", *Recueil des Travaux Chimiques des Pays-Bas*, vol. 80, 1961, pp. 139-148.

Bartl et al., "Thioxanthene Derivatives of Pharmacological Interest: 1,2,4-Trichloro and 2,4,5,6-Tetrachloro Derivatives of 9-(3-Dimethylaminopropylidene)Thioxanthene", *Collection Czechoslov. Chem. Commun.*, vol. 49, 1984, pp. 2295-2308.

Brown et al., "Some Chlorinated Hydroxyphenoxyacetic Acids", *Journal of the Chemical Society*, 1955, pp. 3681-3687.

Budavari, S., "The merck Index, 13$^{th}$ edition", p. 3106, monograph 3108, XP-002347170, 2001.

Cavill et al., "The chemistry of plant-growth regulators. Part I. 2:4-dichloro-6-hydroxyphenoxyacetic acid and related compounds", *Journal of the Chemical Society*, 1954, pp. 565-569.

*Cecil Textbook of Medicine*, 20$^{th}$ ed. (1996), vol. 2, pp. 1992-1996.

*Cecil Textbook of Medicine*, 20$^{th}$ ed. (1996), vol. 2, pp. 2050-2057.

Clemo et al., "Strychnine and brucine. Part II", *Journal of the Chemical Society*, vol. 125, 1924, pp. 1751-1804, XP008053173.

Cocco et al., "Annulation of functionalized hexadienones as an efficient regioselective approach to N-Aryl-2-(trifluoromethyl)-4-pyridinamines", *Tetrahedron Letters*, vol. 40, No. 23, 1999, pp. 4407-4410.

FDA mulls drug to slow late-stage Alzheimer's [online], [retrieved Sep. 24, 2003]. Retrieved from the Internet, URL; http://www.cnn.com/2003/HEALTH/conditions/09/24/alzheimers.drug.ap/index.html>.

Gallo et al., "Spirodioxolanonarenones. II. Synthesis of a halogenated 1,4-dioxaspiro[4,5]deca-7,9-diene-2,6-dione", *Journal of Chemistry*, vol. 30, No. 5, 1965, pp. 1657-1658.

Gaunt et al., "Metabolism of 4-chloro-2-methylphenoxyacetate by a soil pseudomonad", *Biochem. J.*, vol. 122, 1971, pp. 519-526.

Hazeldine et al., "Design, Synthesis and Biological Evaluation of Analogues of the Antitumor Agent, 2-{4-[(7-Chloro-2-quinoxalinyl)oxy]phenoxy}propionic Acid (XK469)", *J. Med. Chem.*, vol. 44, 2001, pp. 1758-1776.

Huston et al., "Chloro derivatives of *o*- and *p*-benzyl phenols. II. Some monochloro, dichloro and trichloro derivatives of ortho and para benzyl phenols", *Journal of the American Chemical Society*, vol. 55, No. 11, 1933, pp. 4639-4643.

Inukai et al., "*ortho*-Disubstituted *F*-benzenes. III. Preparation of (*F*-benzo)heterocyclic compounds from *F*-benzoic acid and *F*-phenol, and the reactions of some intermediary *F*-benzoyl- and *F*-phenoxy compounds", *Bull. Chem. Soc. Jpn.*, vol. 54, No. 11, 1981, pp. 3447-3452.

Janczewski et al., "Effect of Molecular Structure on Optical Properties of Sulfoxide Systems. *o*-Phenoxyphenylsulfinylacetic Acid and some of Their Derivatives. Part II", *Polish Journal of Chemistry*, vol. 62, No. 1-3, 1964, pp. 91-105, XP008053171.

Kmonicek et al., "(Tert-Amino)-11-(4-Methylpiperazino)Dibenzo[*b,f*]Thiepins and their 10,11-Dihydro Derivatives; Synthesis and Neuroleptic Activity", *Collection Czechoslov. Chem. Commun.*, vol. 52, 1987, pp. 792-803, XP-002347166.

Lehmler et al., "Synthesis of hydroxylated PCB metabolites with the Suzuki-coupling", *Chemosphere*, vol. 45, 2001, pp. 1119-1127.

Litvak et al., "Synthesis and S$_N$Ar reactions of new dioxins and predioxins", *Chemosphere*, vol. 43, No. 4-7, 2001, pp. 493-495.

Lupus erythematosus [online], [retrieved Dec. 28, 2006]. Retrieved from the Internet, URL; http://en.wikipedia.org,/wiki/Lupus_erythematosus>.

Maeda et al., "Studies on the Synthesis and Analgesic and Anti-inflammatory Activities of 2-Thiazolylamino- and 2-Thiazolyloxy-arylacetic Acid Derivatives", *Chem. Pharm. Bull.*, vol. 31, No. 10, 1983, pp. 3424-3445, XP-002347167.

Manoury et al., "Synthesis and Analgesic Activities of Some (4-Substituted phenyl-1-piperazinyl)alkyl 2-Aminobenzoates and 2-Aminonicotinates", Journal of Medicinal Chemistry, vol. 22(5), pp. 554-559 (1979).

Meunier et al., "Photochemical behaviour of dichlorprop [(±)-2-(2,4-dichlorophenoxy)propanoic acid] in aqueous solution", *Pest Management Science*, vol. 58, No. 8, 2002, pp. 845-852.

Moser et al., "Synthesis and Quantitative Structure-Activity Relationships of Diclofenac Analogues", *J. Med. Chem.*, vol. 33, 1990, pp. 2358-2368, XP-001024801.

Moshchitskii et al., "Smiles rearrangement of tetrachloropyridyl methyl-hydroxyphenyl sulfone", *Chemistry of Heterocyclic Compounds*, vol. 15, No. 7, 1979, pp. 1085-1088.

Ong et al., "Synthesis and Analgesic Activity of Some Spiro[dibenz[*b,f*]oxepin-10,4'-piperidine] Derivatives", *J. Med. Chem.*, vol. 22, No. 7,1979, pp. 834-839, XP-002347163.

Rajsner et al., "Fluorinated tricyclic Neuroleptics: Synthesis and Pharmacology of 8-Fluoro-4-(4-Methylpiperazino)-4,5-Dihydrothieno[2,3-*b*]-1-Benzothiepin", *Collection Czechoslov. Chem. Commun.*, vol. 44, 1979, pp. 2997-3007, XP-002347164.

Selvi et al., "Vilsmeier cyclization of 2-amino phenoxyacetic acid", *Synthetic Communications*, vol. 31, No. 14, 2001, pp. 2199-2202.

Sindelar et al., "Synthesis of 3-Chloro-5-(4-Methylpiperazino)-6,7-Dihydro-5*H*-Dibenzo[*b,g*]Thiocin, An Eight-Membered Ring Homologue of the Neuroleptic Agent Octoclothepin", *Collection Czechoslov. Chem. Commun.*, vol. 45, 1980, pp. 491-503, XP-002347160.

Sindelar et al., "Fluorinated Tricyclic Neuroleptics with Prolonged Action: 3-Fluoro-8-Trifluoromethyl Derivatives of 10-(4-Methylpiperazino)- and 10-[4-(2-Hydroxyethyl)Piperazino]-10,11-Dihydrodibenzo-[*b,f*]Thiepin", *Collection Czechoslov. Chem. Commun.*, vol. 46, 1981, pp. 118-140, XP-002347168.

Sindler-Kulyk et al., "Synthesis of New 3-(Phenoxyphenyl)sydnones", *J. Hetercyclic Chem.*, vol. 29, No. 2, 1992, pp. 1013-1015, XP-002347161.

Stokker et al., "3-Hydroxy-3-methylglutaryl-coenzyme a Reductase Inhibitors. 5. 6-(Fluoren-9-yl)- and 6-(Fluoren-9-ylidenyl)-3,5-dihydroxyhexanoic Acids and Their Lactone Derivatives", *J. Med. Chem.* 29:852-855 (1986).

Thuillier, G., "Derives des acides 24 aryloxyacetiques a activite neurotrope", *Chimique Therapeutique*, vol. 1, No. 2, 1966, pp. 82-86.

Walsh et al., "Antiinflammatory Activity of *N*-(2-Benzoylphenyl)alanine Derivatives", *J. Med. Chem.*, vol. 27, 1984, pp. 1317-1321, XP-002347162.

Wheatley et al., "2-Benzylphenol Derivatives. III. Basic Ethers", *Journal of American Chemical Society*, vol. 71, No. 11, 1949, pp. 3795-3797.

Database CA [Online] Chemical Abstracts Service, Columbus, Ohio, US; XP002372494 retrieved from STN Database accession No. 1956:16264 abstract & OTT, Donald G. et al: "A carbon-14 tracer study of the alkaline rearrangement of chlorophenanthraquinones" Journal of the American Chemical Society, 77, 2325-9 CODEN:JACSAT; ISSN:0002-7863, 1955.
Database CAPLUS [Online] Chemical Abstracts Service, Columbus, Ohio, US; 1992, XP002372495 retrieved from STN Database accession No. 1992:255529 abstract & RAM, Bhagat et al: "Potential hypolipidemic agents part VI: synthesis and biological activity of some new 4-chloro/methyl-2-pyrazolylphenoxy alkanoates" Indian Drugs, vol. 29, No. 6, 1992, pp. 258-262.
Database WPI 1-3, 5, Section Ch, Week 200365 19, 20, Derwent Publications Ltd., London, GB, Class B03, AN 2003-689635 XP-002301315, WO03068744A1, Ishihara Sangyo Kaisha, Ltd., Aug. 21, 2003.
STN International, File CAPLUS, CAPLUS accession 1-10, No. 1987:597776, document No. 107:197776, Otsuka Pharmaceutical Factory, "Preparation of aminophenol derivatives as anticoagulants, analgesics, hypotensives, and diuretics", JP, A2, 62108859, 19870520.
STN International, File CAPLUS, CAPLUS accession 1-5, 10, No. 1979:186607, document No. 90:186607, Ciba-Geigy, "Phenoxyphenoxyalkanecardoxylic acid derivatives", DE, A1, 2832435, 19790208.
STN International, File CAPLUS, CAPLUS accession 1-5, 10, No. 1971:53748, document No. 74:53748, Walker et al., "Synthesis of 5-phenyl-2,3,4,5-tetrahydro-1,4-benzoxazepines and corresponding 3-ones", & Journal of Organic Chemistry (1970), 36(2), 305-308.
STN International, File CAPLUS, CAPLUS accession 1-3, 5, 10, No. 1992:407796, document No. 117:7796, Tokuyama Soda Co., Ltd., "Preparation of thienyloxphenoxy group-containing carboxylic acids as microbicides", JP, A2, 04021677, 19920124.
STN International, File CAPLUS, CAPLUS accession 1-3, 5, 10, No. 1975:402045, document No. 83:2045, Shiley et al., "Fungicidal activity of some fluoroaromatic compounds", Journal of Fluorine Chemistry (1975), 5(4), 371-376.
STN International, File CAPLUS, CAPLUS accession 1, 3, 5, 10, No. 1972:405106, document No. 77:5106, Oniscu et al., "Monoethanolaminosulfonyl-,diethanolaminosulfonyl- and morpholinosulfonyl-phenoxyacetic derivatives", Buletinul Institutului Politehnic din Iasi, (1971), 14(3-4), 101-114.
STN International, File CAPLUS, CAPLUS accession 1, 3, 5, 10, No. 1961:22702, document No. 55:22702, Takano, K., "Condensation products of furfuryl alcohol. IV. Condensation products of furfuryl alcohol with cresols", Nippon Kagaku Zasshi (1959), 80, 678-681.
STN International, File CAPLUS, CAPLUS accession 1, 3-5, 10, No. 1958:25331, document No. 52:25331, Landa et al., "Properties of sulfide catalysts. V. Preparation of alkylphenols", Chemicke Listy pro Vedu a Prumysl (1957), 51, 1851-1857.
STN Intenational, File CAPLUS, CAPLUS accession 1, 3, 5, 10, No. 1971:498288, document No. 75:98288, Botez et al., "Phenoxybutyric acid sulfamides. I. Sulfamide derivatives of the α-phenoxy-, α-cresoxy-, and α-xylenoxybutyric acids", Buletinul Institutului Politehnic din Iasi (1970), 16(1-2), 161-172.
STN International, File CAPLUS, CAPLUS accession 1-7, 10, No. 1986:109631, document No. 104:109631, Yoshitomi Pharmaceutical Industries, Ltd., "Imidazole derivatives", JP, A2, 60142965, 19850729.
Vippagunta et al., "Crystalline solids", Advanced Drug Delivery Reviews 48:3-26 (2001).
Inflammatory Bowel Disease [online] {retrieved on Apr. 7, 2008 from the internet} {URL:http://www.emedicinehealth.com/script/main/art.asp?articlekey=59121&pf=3&page=8}.
Rheumatoid arthritis [online] {retrieved on Apr. 7, 2008 from the internet} {URL:http://www.nlm.nih.gov/medlineplus/ency/article/000431.htm}.
Asthma [online] [retrieved on May 30, 2008] retrieved from the Internet URL:http://www.nlm.nih.gov/medlineplus/ency/article/000141.htm.

AstraZeneca AB: WO03066046 & WO03066047, "The use of indole-3-acetic acids as CRTH2 receptor antagonists", Expert Opin. Ther. Patents 14(1):125-128 (2004).
Berhenke et al., "Some Aryloxyaliphatic Acids", Journal of the American Chemical Society 73:4458 (1951).
Chemical abstract 123:213132 in CAS (or JP07140725), 1995.
Chemical abstract 123:22081 in CAS (or EP622690), 1994.
Chemical abstract 116:123167 in CAS (or EP455058), 1993.
Chemical abstract 85:56485 in CAS or Parli et al., "The relation between the metabolism of 2,4-dichloro-6-phenylphenoxyethylamine (DPEA) and related compounds and their activities as microsomal mono-oxygenase inhibitors", Drug Metabolism and Disposition 1(4):628-33 (1973).
Chemical abstract 69:93942 in CAS or Cheng et al., "Phenylphenol derivatives with biological activity. III. Fungistatic activity of phenylphenol derivatives", Agricultural and Biological Chemistry 32(9):1162-74 (1968).
Chemical abstract 49:86470 in CAS or Mel'nikov et al., "Structure and physiological activity of alkyl- and aryl-phenoxyacetic acids and their derivatives", Fiziologiya Rastenii 2:267-70 (1955).
Chemical abstract 35:37645 in CAS or Hazlet et al., "The Bromination of 2-Phenylphenyl Acetate", Journal of the American Chemical Society 63:1890-2 (1941).
Chiu et al., "Derivation and Properties of Recombinant Fab Antibodies to Coplanar Polychlorinated Biphenyls", J. Agric. Food Chem. 48:2614-2624 (2000).
Coxworth, "Synthesis of Chlorinated 2-(3-Benzofuranyl)Phenols", Canadian Journal of Chemistry 44:1092-1096 (1966).
Dalal et al., "Synthetic insecticides. I. Synthesis of α, α-bis(aryl)-β, β, γ-trichlorobutanes", STN Accession No. 1950:35789, Document No. 44:35789, Abstract of Journal of the Indian Chemical Society 26:549-52 (1949).
"DialogWeb Records", http://www.dialogweb.com/cgi/document?req=1284661379410, accessed Sep. 16, 2010.
Ebenezar et al., "Prostaglandins in the patent literature", Expert Opin. Ther. Patents 17(9):1131-1145 (2007).
Fromageot et al., "Photodecarboxylation of 2-(2'-carboxymethoxy-5'-methylphenyl)-benzotriazole", Journal of Photochemistry and Photobiology, A: Chemistry 44(1):93-98 (1988).
Gavezzotti, "Are Crystal Structures Predictable?", Acc. Chem. Res. 27:309-314 (1994).
Golub et al., "Molecular Classification of Cancer: Class Discovery and Class Prediction by Gene Expression Monitoring", Science 286:531-537 (1999).
Hazlet et al., "Bromination of 2-phenylphenyl acetate", STN Accession No. 1941:37645, Document No. 35:37645, Abstract of Journal of the American Chemical Society 63:1890-2 (1941).
Hazlet et al., "The Bromination of 2-Phenylphenyl Acetate", Journal of the American Chemical Society 63:1890-1892 (1941).
Ly et al., "Small-molecule CRTH2 antagonists for the treatment of allergic inflammation: an overview", Expert Opin. Invest. Drugs 14(7):769-773 (2005).
Manske et al., "Synthesis and Reactions of Some Dibenzoxepins", Journal of American Chemical Society 72:4797-4799 (1950).
Morissette et al., "High-throughput crystallization: polymorphs, salts, co-crystals and solvates of pharmaceutical solids", Advanced Drug Delivery Reviews 56:275-300 (2004).
Ono Pharm. Co. Ltd: WO03022813 & WO03022814, "The use of prostaglandin $D_2$ receptor antagonists to treat allergic rhinitis", Expert Opin. Ther. Patents 13(10):1657-1661 (2003).
Ram et al., "Potential Hypolipidemic Agents Part VI: Synthesis and Biological Activity of Some New 4-Chloro/Methyl-2-pyrazolylphenoxy Alkanoates", Indian Drugs 29(6), 258-262 (1992).
Ueda et al., "The Synthesis of 10-(4-Methylpiperazino)dibenzo[*bf*] thiepin and Related Compounds. Neurotropic and Psychotropic Agents", Chem. Pharm. Bull. 23(10):2223-2231 (1975).
Ulven et al., "Targeting of the Prostaglandin $D_2$ Receptors DP and CRTH2 for Treatment of Inflammation", Current Topics in Medicinal Chemistry 6:1427-1444 (2006).
Wermuth, "Molecular Variations Based on Isosteric Replacements", The Practice of Medicinal Chemistry, 1996, chapter 13, pp. 203-237.

Rhinitis [online] [retrieved on Nov. 12, 2008 from the internet] URL:http://www.healthline.com/galecontent/rhinitis?print=true.

Preventing Asthma Symptoms [online] [retrieved on Apr. 23, 2010 from the internet] URL:http://www.webmd.com/asthma/guide/asthma-prevention.

Allergic Rhinitis—Prevention [online] [retrieved on Apr. 23, 2010 from the internet] URL:http://www.webmd.com/allergies/tc/allergic-rhinitis-prevention.

COPD Treatments: Improving Your Quality of Life [online] [retrieved on Apr. 23, 2010 from the internet] URL:http://www.webmd.com/lung/copd/copd-treatments-improving-your-quality-of-life.

RN 110624-55-0, retrieved from CAPLUS; retrieved on Apr. 7, 2008.

Database Beilstein chemical extract accession No. 6722243, Jan. 2010.

Database Beilstein chemical extract accession No. 6722682, Jan. 2010.

Database Beilstein chemical extract accession No. 3532059, Jan. 2010.

Database Beilstein chemical extract accession No. 2533336, Jan. 2010.

Database Beilstein chemical extract accession No. 2537173, Jan. 2010.

Database Beilstein chemical extract accession No. 3385275, Jan. 2010.

Database Beilstein chemical extract accession No. 3386554, Jan. 2010.

USPTO Office Action in U.S. Appl. No. 10/552,082, mailed Oct. 29, 2007, 6 pages.

Fish & Richardson P.C., Amendment in Reply to Action of Oct. 29, 2007 in U.S. Appl. No. 10/552,082, filed Feb. 29, 2008, 18 pages.

USPTO Final Office Action in U.S. Appl. No. 10/552,082, mailed Jun. 9, 2008, 18 pages.

Fish & Richardson P.C., Amendment in Reply to Action of Jun. 9, 2008 in U.S. Appl. No. 10/552,082, filed Sep. 9, 2008, 11 pages.

USPTO Office Action in U.S. Appl. No. 10/552,082, mailed Dec. 4, 2008, 23 pages.

Fish & Richardson P.C., Amendment in Reply to Action of Dec. 4, 2008 in U.S. Appl. No. 10/552,082, filed Apr. 6, 2009, 8 pages.

USPTO Notice of Allowance in U.S. Appl. No. 10/552,082, mailed Jul. 1, 2009, 9 pages.

Fish & Richardson P.C., RCE and Interview Summary in response to Notice of Allowance of Jul. 1, 2009 in U.S. Appl. No. 10/552,082, filed Sep. 30, 2009, 2 pages.

USPTO Office Action in U.S. Appl. No. 10/552,082, mailed Jan. 7, 2010, 12 pages.

Fish & Richardson P.C., Amendment in Reply to Action of Jan. 7, 2010 in U.S. Appl. No. 10/552,082, filed Jul. 2, 2010, 8 pages.

USPTO Notice of Allowance in U.S. Appl. No. 10/552,082, mailed Sep. 15, 2010, 12 pages.

USPTO Office Action in U.S. Appl. No. 10/551,783, mailed Dec. 7, 2009, 15 pages.

Fish & Richardson P.C., Amendment in Reply to Action of Dec. 7, 2009 in U.S. Appl. No. 10/551,783, filed Mar. 8, 2010, 17 pages.

USPTO Office Action in U.S. Appl. No. 10/551,783, mailed Apr. 23, 2010, 9 pages.

Fish & Richardson P.C., Amendment in Reply to Action of Apr. 23, 2010 in U.S. Appl. No. 10/551,783, filed Jul. 2, 2010, 23 pages.

USPTO Notice of Allowance in U.S. Appl. No. 10/551,783, mailed Sep. 7, 2010, 6 pages.

Fish & Richardson P.C., RCE and IDS in reply to Notice of Allowance of Sep. 7, 2010 in U.S. Appl. No. 10/551,783, filed Dec. 6, 2010, 4 pages.

USPTO Office Action in U.S. Appl. No. 10/569,065, mailed May 4, 2007, 12 pages.

Fish & Richardson P.C., Amendment in Reply to Action of May 4, 2007 in U.S. Appl. No. 10/569,065, filed Aug. 3, 2007, 14 pages.

USPTO Final Office Action in U.S. Appl. No. 10/569,065, mailed Oct. 17, 2007, 4 pages.

Fish & Richardson P.C., Amendment in Reply to Action of Oct. 17, 2007 in U.S. Appl. No. 10/569,065, filed Jan. 17, 2008, 9 pages.

USPTO Office Action in U.S. Appl. No. 10/569,065, mailed Apr. 16, 2008, 14 pages.

Fish & Richardson P.C., Amendment in Reply to Action of Apr. 16, 2008 in U.S. Appl. No. 10/569,065, filed Jul. 16, 2008, 38 pages.

USPTO Office Action in U.S. Appl. No. 10/569,065, mailed Oct. 28, 2008, 15 pages.

Fish & Richardson P.C., Amendment in Reply to Action of Oct. 28, 2008 in U.S. Appl. No. 10/569,065, filed Jan. 27, 2009, 7 pages.

USPTO Office Action in U.S. Appl. No. 10/569,065, mailed May 13, 2009, 10 pages.

Fish & Richardson P.C., Amendment in Reply to Action of May 13, 2009 in U.S. Appl. No. 10/569,065, filed Jul. 14, 2009, 9 pages.

USPTO Notice of Allowance in U.S. Appl. No. 10/569,065, mailed Oct. 23, 2009, 10 pages.

Fish & Richardson P.C., RCE and IDS in Reply to Notice of Allowance of Oct. 23, 2009 in U.S. Appl. No. 10/569,065, filed Nov. 5, 2009, 3 pages.

USPTO Notice of Allowance in U.S. Appl. No. 10/569,065, mailed Jan. 28, 2010, 9 pages.

Fish & Richardson P.C., RCE and IDS in Reply to Notice of Allowance of Jan. 28, 2010 in U.S. Appl. No. 10/569,065, filed Mar. 31, 2010, 5 pages.

USPTO Notice of Allowance in U.S. Appl. No. 10/569,065, mailed May 13, 2010, 10 pages.

Fish & Richardson P.C., RCE and IDS in Reply to Notice of Allowance of May 13, 2010 in U.S. Appl. No. 10/569,065, filed Aug. 2, 2010, 4 pages.

USPTO Notice of Allowance in U.S. Appl. No. 10/569,065, mailed Sep. 1, 2010, 9 pages.

Fish & Richardson P.C., RCE and IDS in Reply to Notice of Allowance of Sep. 1, 2010 in U.S. Appl. No. 10/569,065, filed Nov. 8, 2010, 5 pages.

USPTO Notice of Allowance in U.S. Appl. No. 10/569,065, mailed Dec. 2, 2010, 10 pages.

Fish & Richardson P.C., RCE and IDS in Reply to Notice of Allowance of Dec. 2, 2010 in U.S. Appl. No. 10/569,065, filed Feb. 15, 2011, 5 pages.

USPTO Notice of Allowance in U.S. Appl. No. 10/569,065, mailed Apr. 8, 2011, 10 pages.

USPTO Office Action in U.S. Appl. No. 11/571,707, mailed Mar. 12, 2010, 16 pages.

Fish & Richardson P.C., Amendment in Reply to Action of Mar. 12, 2010 in U.S. Appl. No. 11/571,707, filed Sep. 3, 2010, 14 pages.

USPTO Notice of Allowance in U.S. Appl. No. 11/571,707, mailed Nov. 22, 2010, 12 pages.

Fish & Richardson P.C., Response to Notice of Allowance of Nov. 22, 2010 in U.S. Appl. No. 11/571,707, filed Feb. 18, 2011, 12 pages.

Fish & Richardson P.C., RCE, Petition to Withdraw from Issue, and IDS in U.S. Appl. No. 11/571,707, filed Apr. 13, 2011, 7 pages.

USPTO Office Action in U.S. Appl. No. 11/574,076, mailed Oct. 27, 2008, 23 pages.

Fish & Richardson P.C., Amendment in Reply to Action of Oct. 27, 2008 in U.S. Appl. No. 11/574,076, filed Apr. 27, 2009, 21 pages.

USPTO Final Office Action in U.S. Appl. No. 11/574,076, mailed Aug. 18, 2009, 7 pages.

Fish & Richardson P.C., RCE and Amendment in Reply to Action of Aug. 18, 2009 in U.S. Appl. No. 11/574,076, filed Dec. 18, 2009, 13 pages.

USPTO Notice of Allowance in U.S. Appl. No. 11/574,076, mailed Feb. 3, 2010, 12 pages.

Fish & Richardson P.C., Response to Notice of Allowance of Feb. 3, 2010 in U.S. Appl. No. 11/574,076, filed Apr. 30, 2010, 2 pages.

USPTO Office Action in U.S. Appl. No. 11/576,372, mailed Jul. 22, 2009, 19 pages.

Fish & Richardson P.C., Amendment in Reply to Action of Jul. 22, 2009 in U.S. Appl. No. 11/576,372, filed Jan. 22, 2010, 18 pages.

USPTO Final Office Action in U.S. Appl. No. 11/576,372, mailed May 7, 2010, 7 pages.

Fish & Richardson P.C., Reply to Action of May 7, 2010 in U.S. Appl. No. 11/576,372, filed Aug. 9, 2010, 10 pages.

USPTO Office Action in U.S. Appl. No. 11/576,372, mailed Sep. 2, 2010, 7 pages.

Fish & Richardson P.C., RCE, IDS and Amendment in Reply to Action of Sep. 2, 2010 in U.S. Appl. No. 11/576,372, filed Dec. 2, 2010, 16 pages.

USPTO Office Action in U.S. Appl. No. 11/719,832, mailed Apr. 30, 2010, 20 pages.
Fish & Richardson P.C., Amendment in Reply to Action of Apr. 30, 2010 in U.S. Appl. No. 11/719,832, filed Aug. 30, 2010, 18 pages.
USPTO Office Action in U.S. Appl. No. 11/719,832, mailed Oct. 6, 2010, 12 pages.
Fish & Richardson P.C., RCE, IDS and Amendment in Reply to Action of Oct. 6, 2010 in U.S. Appl. No. 11/719,832, filed Apr. 6, 2011, 27 pages.
USPTO Office Action in U.S. Appl. No. 12/089,276, mailed Jun. 17, 2009, 28 pages.
Fish & Richardson P.C., Amendment in Reply to Action of Jun. 17, 2009 in U.S. Appl. No. 12/089,276, filed Sep. 22, 2009, 10 pages.
USPTO Notice of Allowance in U.S. Appl. No. 12/089,276, mailed Jan. 4, 2010, 6 pages.
Fish & Richardson P.C., RCE and IDS in Reply to Notice of Allowance of Jan. 4, 2010 in U.S. Appl. No. 12/089,276, filed Mar. 31, 2010, 7 pages.
USPTO Notice of Allowance in U.S. Appl. No. 12/089,276, mailed Apr. 21, 2010, 11 pages.
Fish & Richardson P.C., RCE and IDS in Reply to Notice of Allowance of Apr. 21, 2010 in U.S. Appl. No. 12/089,276, filed Jul. 21, 2010, 5 pages.
USPTO Notice of Allowance in U.S. Appl. No. 12/089,276, mailed Sep. 21, 2010, 9 pages.
Fish & Richardson P.C., RCE and IDS in Reply to Notice of Allowance of Sep. 21, 2010 in U.S. Appl. No. 12/089,276, filed Dec. 20, 2010, 6 pages.
USPTO Notice of Allowance in U.S. Appl. No. 12/089,276, mailed Jan. 4, 2011, 11 pages.
Fish & Richardson P.C., RCE and IDS in Reply to Notice of Allowance of Jan. 4, 2011 in U.S. Appl. No. 12/089,276, filed Apr. 4, 2011, 4 pages.
USPTO Notice of Allowance in U.S. Appl. No. 12/089,276, mailed Apr. 12, 2011, 9 pages.
USPTO Office Action in U.S. Appl. No. 12/092,431, mailed Aug. 4, 2009, 8 pages.
Fish & Richardson P.C., Amendment in Reply to Action of Aug. 4, 2009 in U.S. Appl. No. 12/092,431, filed Feb. 3, 2010, 15 pages.
USPTO Final Office Action in U.S. Appl. No. 12/092,431, mailed May 4, 2010, 13 pages.
Fish & Richardson P.C., RCE, IDS and Amendment in Reply to Action of May 4, 2010 in U.S. Appl. No. 12/092,431, filed Sep. 7, 2010, 16 pages.
USPTO Office Action in U.S. Appl. No. 12/167,513, mailed Nov. 2, 2009, 19 pages.
Fish & Richardson P.C., Amendment in Reply to Action of Nov. 2, 2009 in U.S. Appl. No. 12/167,513, filed Feb. 2, 2010, 19 pages.
USPTO Final Office Action in U.S. Appl. No. 12/167,513, mailed Apr. 22, 2010, 22 pages.
Fish & Richardson P.C., Amendment in Reply to Action of Apr. 22, 2010 in U.S. Appl. No. 12/167,513, filed Oct. 22, 2010, 22 pages.

* cited by examiner

COMPOUNDS

CROSS-REFERENCE TO RELATED APPLICATIONS

This application is a national phase application under 35 U.S.C. §371 of PCT International Application No. PCT/GB2006/003689, filed Oct. 5, 2006, which claims the benefit of United Kingdom Application Serial No. 0520323.7, filed Oct. 6, 2005 and United Kingdom Application Serial No. 0608299.4, filed Apr. 27, 2006. Each of these prior applications is incorporated herein by reference in its entirety.

The present invention relates to substituted phenylacetic acids as useful pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTH2. GB 1356834 discloses a series of compounds said to possess anti-inflammatory, analgesic and antipyretic activity. It has been found that certain phenylacetic acids are active at the CRTH2 receptor, and as a consequence are expected to be potentially useful for the treatment of various respiratory diseases, including asthma and COPD.

Phenyl acetic acids which bind to CRTh2 are disclosed in WO2004/058164. These compounds have dual activity at both the CRTh2 and DP receptors. The compounds disclosed in WO2004/058164 have embedded amino derived substituents which could potentially be metabolised to give mutagenic anilines.

Related compounds are disclosed in EP91402638, and are said to be useful in the treatment of various inflammatory and/or allergic diseases, particularly asthma, allergic rhinitis, arthritis and inflammation.

The present invention relates to compounds that bind selectively to the CRTh2 receptor. These phenyl acetic acids also do not contain any potentially toxic embedded anilines and are therefore advantageous as potential drug molecules.

In a first aspect the invention therefore provides a compound of formula (I) or a pharmaceutically acceptable salt thereof:

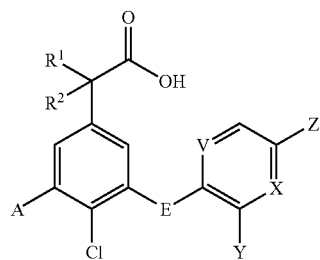

(I)

in which:

A and D are independently selected from hydrogen, halogen, CN, $OR^3$, $S(O)nR^3$ (where n is 0, 1 or 2), nitro, aryl, heteroaryl, $C_{3-8}$cycloalkyl or $C_{1-6}$alkyl, the latter two groups being optionally substituted by halogen atoms;

E is O, S, $NR^6$ or $CR^1R^2$;

V is N or C(H);

W is nitrogen or W is a carbon atom substituted by hydrogen, halogen, CN, $SO_2R^9$, or $C_{1-3}$ alkyl (the latter group being optionally substituted by halogen atoms);

X is nitrogen or X is a carbon atom substituted by hydrogen, halogen, CN, $SO_2R^9$, or $C_{1-3}$ alkyl (the latter group being optionally substituted by halogen atoms);

Y is selected from hydrogen, CN, halogen, $C_{1-6}$ alkyl (the latter being optionally substituted by one or more halogen atoms);

Z is selected from hydrogen, halogen, CN, $SO_2NR^4R^5$, $CONR^4R^5$, $COR^6$, $CO_2R^6$, $SO_2R^9$ or $OR^9$;

$R^1$ and $R^2$ independently represent a hydrogen atom, halogen, or a $C_{1-6}$alkyl group; or $R^1$ and $R^2$ together can form a 3-8 membered ring optionally containing one or more atoms selected from O, S, $NR^6$ and itself optionally substituted by one or more $C_{1-3}$ alkyl or halogen;

$R^3$ is hydrogen, $C_{1-6}$ alkyl (optionally substituted by halogen or $NR^4R^5$) or $SO_2R^7$;

$R^4$ and $R^5$ independently represent hydrogen, $C_{3-8}$ cycloalkyl or $C_{1-6}$alkyl the latter two groups being optionally substituted by one or more substituents independently selected from halogen, CN, $C_{3-7}$ cycloalkyl, $C_{1-6}$ alkyl, $OR^3$ and $NR^7R^8$, aryl, heteroaryl, $S(O)_nR^9$ (where n=0, 1 or 2), $CONR^7R^8$, $NR^3COR^{10}$, $SO_2NR^4R^5$ and $NR^3SO_2R^9$; or $R^4$ and $R^5$ together with the nitrogen atom to which they are attached can form a 3-8 membered saturated ring optionally containing one or more atoms selected from O, N, $S(O)_n$ (where n=0, 1 or 2), $NR^3$, and itself optionally substituted by one or more halogen, $OR^3$, $C_{3-9}$ cycloalkyl or $C_{1-6}$ alkyl, the latter two groups being optionally substituted by one or more halogen;

$R^6$ represents aryl, heteroaryl, $C_{3-8}$ cycloalkyl or $C_{1-6}$alkyl all of which being optionally substituted by one or more substituents independently selected from halogen, $C_{3-7}$ cycloalkyl, $C_{1-6}$ alkyl, $OR^3$, CN, $NR^7R^8$, aryl, heteroaryl, $S(O)_nR^9$ (where n=0, 1 or 2), $CONR^7R^8$, $NR^3COR^{10}$, $SO_2NR^4R^5$ and $NR^3SO_2R^9$;

$R^7$ independently represents a hydrogen atom or $C_1$-$C_6$ alkyl (the alkyl group can be optionally substituted by one or more halogen atoms);

$R^8$ is hydrogen, $C_{1-4}$ alkyl, —$COC_1$-$C_4$ alkyl, $CO_2C_1$-$C_4$alkyl or $CONR^6C_1$-$C_4$alkyl;

$R^9$ represents aryl, heteroaryl, $C_3$-$C_7$ cycloalkyl or $C_{1-6}$alkyl, the latter two groups may be optionally substituted by one or more substituents independently selected from halogen, $C_3$-$C_7$ cycloalkyl, aryl, heteroaryl, $OR^6$ and $NR^{10}R^{11}$, $S(O)_nR^6$ (where n=0, 1 or 2), $CONR^6R^7$, $NR^6COR^7$, $SO_2NR^4R^5$ and $NR^6SO_2R^7$;

$R^{10}$ and $R^{11}$ independently represent aryl or heteroaryl, hydrogen, $C_{3-7}$ cycloalkyl or $C_{1-6}$alkyl, the latter two groups being optionally substituted by one or more substituents independently selected from halogen, $C_{3-7}$ cycloalkyl, aryl, heteroaryl, OH, $OR^9$ and $NR^4R^5$, $S(O)_nR^6$ (where n=0, 1 or 2), $CONR^4R^5$, $NR^6COR^7$, $SO_2NR^4R^5$ and $NR^6SO_2R^7$; or $R^{10}$ and $R^{11}$ together with the nitrogen atom to which they are attached can form a 3-8 membered saturated heterocylic ring optionally containing one or more atoms selected from O, S(O), (where n=0, 1 or 2), $NR^8$, and itself optionally substituted by halogen or $C_1$-$C_3$ alkyl, provided that:

A and D cannot both be hydrogen;

A and D cannot be aryl substituted in the para-position by —$S(O)_n$—, where n is 0, 1 or 2;

when V, W and X are all carbon then all of the substituents on the phenyl ring (V, W, X, Y and Z) cannot be hydrogen.

In the context of the present specification, unless otherwise indicated, an alkyl or alkenyl group or an alkyl or alkenyl moiety in a substituent group may be linear or branched and maybe optionally substituted by one or more halogen atoms.

Examples of aryl include phenyl and naphthyl.

Heteroaryl is defined as a 5-7 member aromatic ring or can be 6,6- or 6,5-fused bicyclic ring optionally containing one or more heteroatoms selected from N, S, O. The bicyclic ring may be linked through carbon or nitrogen and may be attached through the 5 or 6 membered ring and can be fully or partially saturated.

Examples include but are not limited to pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, benzoxazole, purine, 4H-quinolizine, cinnoline, phthalazine, quinazoline, quinoxaline, 1,8-naphthyridine, pteridine, quinolone and 1,2-methylenedioxy benzene.

Aryl or heteroaryl groups as substituents can be optionally substituted by one or more substituents independently selected from halogen, CN, $OR^7$, $SO_2R^3$, $CONR^7R^8$, $SO_2NR^4R^5$, $C_{3-8}$ cycloalkyl or $C_{1-6}$ alkyl, the latter two groups being optionally substituted by one or more substituents independently selected from halogen, $OR^3$.

Preferably A is hydrogen, halogen, CN, $OR^3$, aryl, heteroaryl or $C_{1-6}$alkyl, the latter group being optionally substituted by one or more halogen atoms;

More preferably A is hydrogen, halogen or $C_{1-6}$alkyl, the latter group being optionally substituted by one or more halogen atoms;

Preferably D is hydrogen, halogen or $C_{1-6}$alkyl, the latter group being optionally substituted by one or more halogen atoms;

Preferably where D is not hydrogen then A is hydrogen; where A is not hydrogen then D is hydrogen;

Preferably E is oxygen or sulfur; more preferably E is oxygen;

Preferably V is C(H);

Preferably W is a carbon atom substituted by hydrogen, halogen, CN or $C_{1-3}$ alkyl (the latter group being optionally substituted by halogen atoms); more preferably W is a carbon atom substituted by hydrogen, halogen or $C_{1-3}$ alkyl (the latter group being optionally substituted by halogen atoms); most preferably W is C(H);

Preferably X is a carbon atom substituted by hydrogen or halogen; more preferably X is C(H);

Preferably Y is halogen, cyano or $C_{1-3}$ alkyl optionally substituted by halogen atoms;

Preferably Z is selected from $SO_2R^9$, $SO_2NR^4R^5$, $CONR^4R^5$ or $COR^6$;

More preferably Z is $SO_2R^9$;

Preferably $R^1$ and $R^2$ are both hydrogen, or one of $R^1$ or $R^2$ is methyl and the other is hydrogen. More preferably $R^1$ and $R^2$ are both hydrogen;

Preferred compounds of the invention include:
{4-chloro-3-[2-chloro-4-(methylsulfonyl)phenoxy]phenyl}acetic acid;
{4-chloro-3-[4-(methylsulfonyl)-2-(trifluoromethyl)phenoxy]phenyl}acetic acid;
{4-chloro-3-[2-chloro-4-(ethylsulfonyl)phenoxy]phenyl}acetic acid;
{4-chloro-3-[4-(ethylsulfonyl)-2-(trifluoromethyl)phenoxy]phenyl}acetic acid;
{4-chloro-3-[4-(methylsulfonyl)phenoxy]phenyl}acetic acid;
2-{4-chloro-3-[2-chloro-4-(methylsulfonyl)phenoxy]phenyl}propanoic acid;
(4-chloro-3-{2-chloro-4-[(dimethylamino)sulfonyl]phenoxy}phenyl)acetic acid;
[4-chloro-3-(3-cyanophenoxy)phenyl]acetic acid;
{4-chloro-3-[2-fluoro-4-(methylsulfonyl)phenoxy]phenyl}acetic acid;
{4-chloro-3-[4-(ethylsulfonyl)-2-fluorophenoxy]phenyl}acetic acid;
{4-chloro-3-[2-cyano-4-(methylsulfonyl)phenoxy]phenyl}acetic acid;
{4-chloro-3-[2-cyano-4-(ethylsulfonyl)phenoxy]phenyl}acetic acid;
{4-chloro-3-[4-(methylsulfonyl)-3-(trifluoromethyl)phenoxy]phenyl}acetic acid;
{4-chloro-3-[2-cyano-5-(trifluoromethyl)phenoxy]phenyl}acetic acid;
(4-chloro-3-{2-fluoro-4-[(4-fluorobenzyl)sulfonyl]phenoxy}phenyl)acetic acid;
[3-(4-benzoyl-2-fluorophenoxy)-4-chlorophenyl]acetic acid;
(4-chloro-3-{2-chloro-4-[(isobutylamino)carbonyl]phenoxy}phenyl)acetic acid;
{3-chloro-5-[2-chloro-4-(methylsulfonyl)phenoxy]phenyl}acetic acid;
{3-chloro-5-[2-chloro-4-(ethylsulfonyl)phenoxy]phenyl}acetic acid;
{3-[2-chloro-4-(ethylsulfonyl)phenoxy]-5-fluorophenyl}acetic acid;
{3-fluoro-5-[4-(methylsulfonyl)-2-(trifluoromethyl)phenoxy]phenyl}acetic acid;
{3-[2-chloro-4-(ethylsulfonyl)phenoxy]-4-fluorophenyl}acetic acid;
{4-fluoro-3-[4-(methylsulfonyl)-2-(trifluoromethyl)phenoxy]phenyl}acetic acid;
{4-chloro-3-[2-fluoro-4-(phenylsulfonyl)phenoxy]phenyl}acetic acid;
[3-[2-chloro-4-(methylsulfonyl)phenoxy]-5-(trifluoromethyl)phenyl]acetic acid;
[3-[2-chloro-4-(ethylsulfonyl)phenoxy]-5-(trifluoromethyl)phenyl]acetic acid;
{3-chloro-5-[2-fluoro-4-(methylsulfonyl)phenoxy]phenyl}acetic acid;
{3-chloro-5-[2-cyano-4-(ethylsulfonyl)phenoxy]phenyl}acetic acid;
{3-chloro-5-[2-chloro-4-(phenylsulfonyl)phenoxy]phenyl}acetic acid;
{3-chloro-5-[4-(ethylsulfonyl)-2-fluorophenoxy]phenyl}acetic acid;
{3-chloro-5-[2-fluoro-4-(phenylsulfonyl)phenoxy]phenyl}acetic acid;
[3-{2-fluoro-4-[(4-fluorobenzyl)sulfonyl]phenoxy}-5-(trifluoromethyl)phenyl]acetic acid;
(3-chloro-5-{4-[(4-fluorobenzyl)sulfonyl]phenoxy}phenyl)acetic acid;
(3-chloro-5-{2-chloro-4-[(4-fluorobenzyl)sulfonyl]phenoxy}phenyl)acetic acid;
{3-chloro-5-[4-(methylsulfonyl)-2-(trifluoromethyl)phenoxy]phenyl}acetic acid;
{3-chloro-5-[4-(ethylsulfonyl)-2-(trifluoromethyl)phenoxy]phenyl}acetic acid;
[3-[2-fluoro-4-(phenylsulfonyl)phenoxy]-5-(trifluoromethyl)phenyl]acetic acid;
[3-[2-chloro-4-(phenylsulfonyl)phenoxy]-5-(trifluoromethyl)phenyl]acetic acid;
[3-[4-(ethylsulfonyl)-2-fluorophenoxy]-5-(trifluoromethyl)phenyl]acetic acid;
[3-[2-cyano-4-(ethylsulfonyl)phenoxy]-5-(trifluoromethyl)phenyl]acetic acid;

[3-[4-(ethylsulfonyl)-2-(trifluoromethyl)phenoxy]-5-(trifluoromethyl)phenyl]acetic acid;
{3-[4-(benzylsulfonyl)-2-chlorophenoxy]-5-chlorophenyl}acetic acid;
{3-chloro-5-[4-(phenylsulfonyl)-2-(trifluoromethyl)phenoxy]phenyl}acetic acid;
{3-chloro-5-[2-cyano-4-(phenylsulfonyl)phenoxy]phenyl}acetic acid;
{3-[4-(benzylsulfonyl)-2-fluorophenoxy]-5-chlorophenyl}acetic acid;
(3-chloro-5-{2-fluoro-4-[(3-fluorobenzyl)sulfonyl]phenoxy}phenyl)acetic acid;
{3-[4-(benzylsulfonyl)-2-(trifluoromethyl)phenoxy]-5-chlorophenyl}acetic acid;
(3-chloro-5-{2-fluoro-4-[(2-fluorobenzyl)sulfonyl]phenoxy}phenyl)acetic acid;
(3-chloro-5-{4-[(4-chlorobenzyl)sulfonyl]-2-fluorophenoxy}phenyl)acetic acid;
2-[3-[4-(ethylsulfonyl)-2-(trifluoromethyl)phenoxy]-5-(trifluoromethyl)phenyl]propanoic acid;
2-[3-[2-chloro-4-(ethylsulfonyl)phenoxy]-5-(trifluoromethyl)phenyl]propanoic acid;
2-[3-[2-chloro-4-(phenylsulfonyl)phenoxy]-5-(trifluoromethyl)phenyl]propanoic acid;
2-[3-{2-chloro-4-[(4-fluorobenzyl)sulfonyl]phenoxy}-5-(trifluoromethyl)phenyl]propanoic acid;
(3-chloro-5-{4-[(4-chlorobenzyl)sulfonyl]-2-fluorophenoxy}phenyl)acetic acid;
{3-bromo-5-[2-chloro-4-(ethylsulfonyl)phenoxy]phenyl}acetic acid;
{3-[2-chloro-4-(ethylsulfonyl)phenoxy]-5-methylphenyl}acetic acid;
methyl 3-[2-chloro-4-(ethylsulfonyl)phenoxy]-5-cyanobenzoate;
[3-{[2-chloro-4-(ethylsulfonyl)phenyl]thio}-5-(trifluoromethyl)phenyl]acetic acid;
{3-[2-chloro-4-(ethylsulfonyl)phenoxy]-5-methoxyphenyl}acetic acid;
[3-{2-chloro-4-[(2-fluorobenzyl)sulfonyl]phenoxy}-5-(trifluoromethyl)phenyl]acetic acid;
[3-{[3-methyl-5-(phenylsulfonyl)pyridin-2-yl]oxy}-5-(trifluoromethyl)phenyl]acetic acid;
[3-[2-chloro-4-(morpholin-4-ylsulfonyl)phenoxy]-5-(trifluoromethyl)phenyl]acetic acid;
[3-(4-benzoyl-2-chlorophenoxy)-5-(trifluoromethyl)phenyl]acetic acid;
[3-{2-chloro-4-[(3-fluorobenzyl)sulfonyl]phenoxy}-5-(trifluoromethyl)phenyl]acetic acid;
{3-bromo-5-[2-fluoro-4-(phenylsulfonyl)phenoxy]phenyl}acetic acid;
[3-{2-fluoro-4-[(4-fluorophenyl)sulfonyl]phenoxy}-5-(trifluoromethyl)phenyl]acetic acid;
{3-chloro-5-[4-(ethylsulfonyl)-3-(trifluoromethyl)phenoxy]phenyl}acetic acid;
{3-chloro-5-[5-chloro-2-fluoro-4-(pyrrolidin-1-ylcarbonyl)phenoxy]phenyl}acetic acid;
{3-cyano-5-[2-fluoro-4-(phenylsulfonyl)phenoxy]phenyl}acetic acid;
(3-chloro-5-{2-fluoro-4-[(4-fluorophenyl)sulfonyl]phenoxy}phenyl)acetic acid;
(3-chloro-5-{[2-cyano-4-(ethylsulfonyl)phenyl]thio}phenyl)acetic acid;
(3-chloro-5-{[4-(ethylsulfonyl)-2-(trifluoromethyl)phenyl]thio}phenyl)acetic acid;
(3-chloro-5-{[2-fluoro-4-(phenylsulfonyl)phenyl]thio}phenyl)acetic acid;
[3-(4-benzoyl-3,5-difluorophenoxy)-5-chlorophenyl]acetic acid;
{3-chloro-5-[2-chloro-4-(4-fluorobenzoyl)phenoxy]phenyl}acetic acid;
{3-[2-fluoro-4-(phenylsulfonyl)phenoxy]-5-methylphenyl}acetic acid;
{3-ethyl-5-[2-fluoro-4-(phenylsulfonyl)phenoxy]phenyl}acetic acid;
[3-{2-chloro-4-[(4-fluorobenzyl)sulfonyl]phenoxy}-5-(trifluoromethyl)phenyl]acetic acid;
[3-[2-cyano-4-(phenylsulfonyl)phenoxy]-5-(trifluoromethyl)phenyl]acetic acid;
{5-[2-chloro-4-(ethylsulfonyl)phenoxy]biphenyl-3-yl}acetic acid;
{3-[2-chloro-4-(ethylsulfonyl)phenoxy]-5-pyridin-2-ylphenyl}acetic acid;
{3-[2-chloro-4-(ethylsulfonyl)phenoxy]-5-[2-(dimethylamino)ethoxy]phenyl}acetic acid
[3-{2-chloro-4-[(pyridin-2-ylmethyl)sulfonyl]phenoxy}-5-(trifluoromethyl)phenyl]acetic acid
and pharmaceutically acceptable salts thereof.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, tertiarybutylamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

It will be appreciated by those skilled in the art that in the processes of the present invention certain functional groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of formula (I) can be prepared by reaction of a compound of formula (II) with a compound of formula (III) as outlined in Scheme 1:

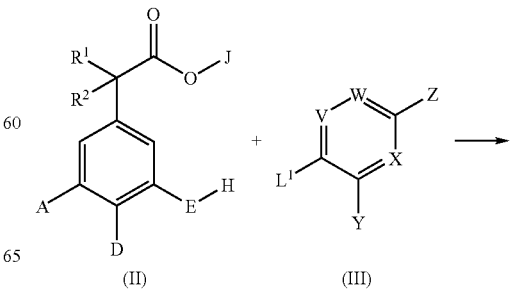

Scheme 1

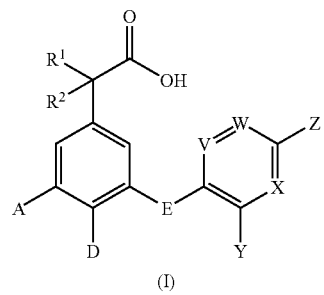

(I)

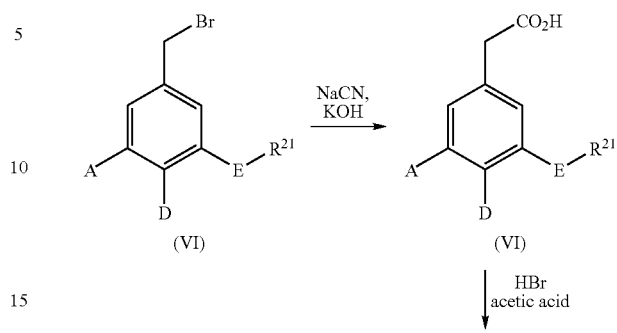

In which A, D, E, V, W, X, Y, Z, R¹ and R² are as defined in formula (I) or are protected derivatives thereof. $L^1$ is a leaving group such as halogen, preferably fluoro or chloro. J is alkyl for example methyl, ethyl or tertiary butyl. The reaction is carried out at elevated temperatures in a polar solvent such as NMP or DMF in the presence of a base, such as cesium carbonate or the like. The ester group is subsequently removed using a base such as sodium hydroxide in a suitable organic solvent such as methanol, ethanol or THF.

Compounds of formula (I) can also be prepared directly by reacting compounds of formula (IV) with compounds of formula (III).

Compounds of formula (II) and formula (IV) can be prepared as outlined in Scheme 2:

Scheme 2

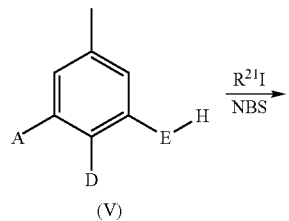

(V)

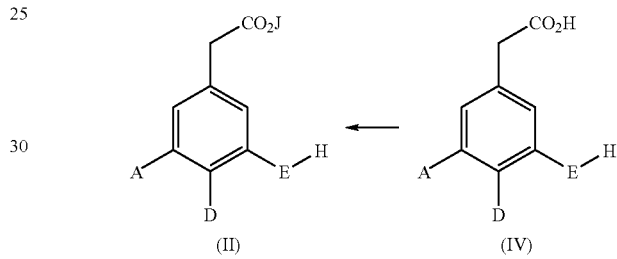

In which A, D and Y, are as defined in formula (I) or are protected derivatives thereof. J is as defined for compounds of formula (II). $R^{21}$ is $C_{1-3}$ alkyl, such as methyl.

Hydrolysis of the ester group J can be carried out using routine procedures, for example treatment of methyl and ethyl esters with aqueous sodium hydroxide, and treatment of tert-butyl esters with acids such as trifluoroacetic acid.

Compounds of formula (IV) in which E is O can be prepared as outlined in Scheme 2A:

Scheme 2A

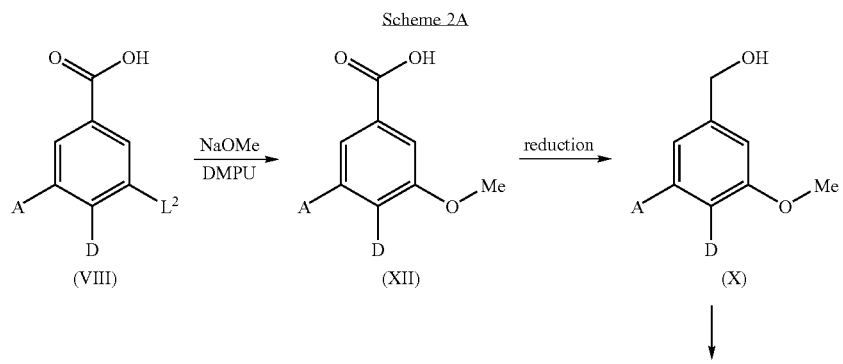

-continued

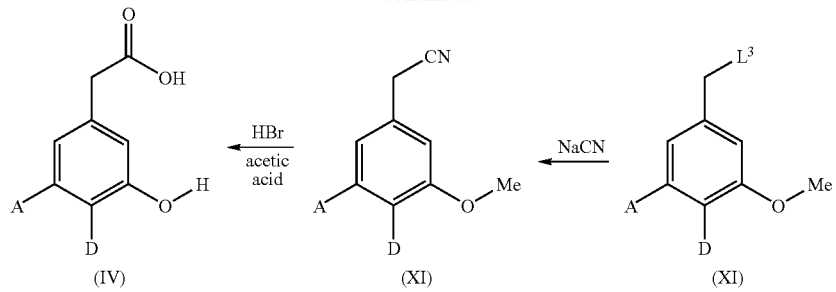

In which A and D are as defined in formula (I) or are protected derivatives thereof $L^2$ is a chlorine or flourine. $L^3$ is a suitable leaving group such as chlorine, bromine or mesylate.

The group $L^2$ in compounds of formula (VIII) is displaced using sodium methoxide in a suitable solvent such as DMPU or HMPA. The benzoic acid group is then reduced to the alcohol using lithium aluminium hydride or borane in a suitable solvent such as THF. The leaving group $L^3$ can be introduced by reacting compounds of formula (X) with thionyl chloride or phosphorus tribromide or by converting to the mesylate by reacting compounds of formula (X) with methane sulfonyl chloride in the presence of a base such as triethylamine in a suitable organic solvent such as dichloromethane. The group $L^3$ is then displaced with sodium cyanide in a polar solvent such as DMF at elevated temperatures to give compounds of formula (XII). The nitrile can be hydrolysed to the acid and the group Y deprotected in one step using aqueous HBr in acetic acid at elevated temperatures.

Certain compounds of formula (VIII) are commercially available.

Some compounds of formula (III) in which one of the substituents is $SO_2R^9$ can be prepared by general reaction Scheme 3:

Scheme 3

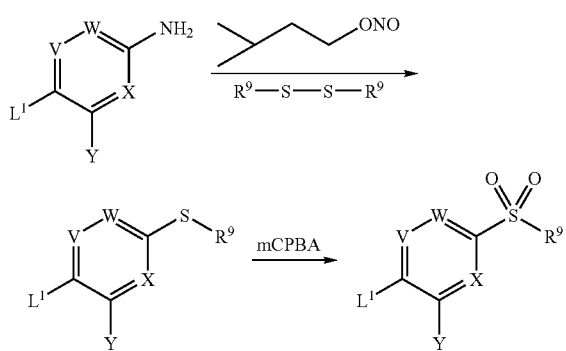

In which $L^1$, V, W, X and Y and $R^9$ are as defined in formula (III) or are protected derivatives thereof. The diazotisation is carried out at elevated temperatures, such as 60° C. in a suitable organic solvent for example acetonitrile. The corresponding sulfide is oxidised using MCPBA or oxone as the oxidising agent in a suitable solvent, for example, dichloromethane.

Certain compounds of formula (III) containing a sulfone moiety can also be prepared as outlined in reaction Scheme 4:

Scheme 4

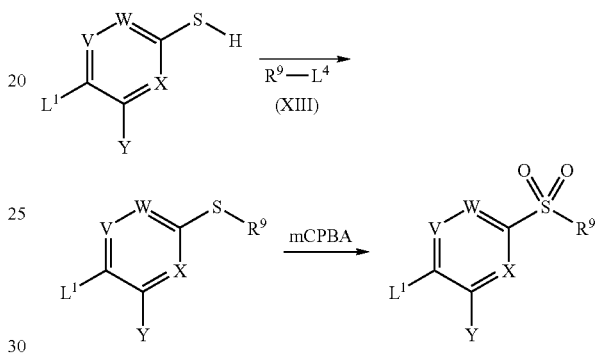

In which $L^1$, V, W, X, Y and $R^9$ are as defined in formula (III) or protected derivatives thereof.

$L^4$ is a suitable leaving group such as halogen, preferably iodide, bromide or chloride. The thiol is reacted with compounds of formula (XIII) and then oxidised using a suitable oxidising agent such as MCPBA or oxone.

Certain compounds of formula (III) in which Z is $COR^6$ can be prepared as outlined in Scheme 5:

Scheme 5.

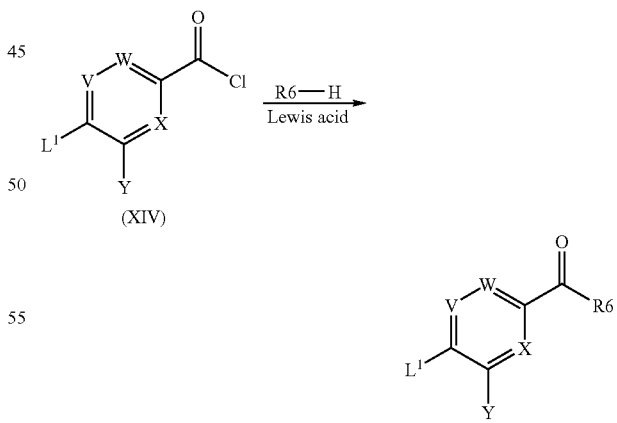

In which $L^1$, V, W, X, Y and $R^6$ are as defined in formula (III) or protected derivatives thereof. Compounds of formula (XIV) can undergo a Friedel-Crafts acylation using standard conditions, for example heating in the presence of a suitable Lewis Acid such as iron (III) chloride. Compounds of formula (XIV) are commercially available or are prepared using known literature procedures.

Certain compounds of formula (III) in which Z is SO$_2$NR$^4$R$^5$ or CONR$^4$R$^5$ are prepared as outlined in Scheme 6:

Scheme 6

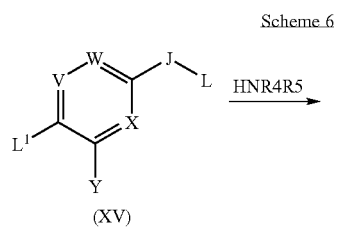

In which L$^1$, V, W, X, Y, R$^4$ and R$^5$ are as defined in formula (III) or are protected derivatives thereof and in which J is C(O) or SO$_2$ and L is a suitable leaving group such as halogen or alternatively L is hydroxy. The coupling is carried out using standard amide or sulphonamide coupling procedures. For example, where L is halogen the reaction can be carried out by stirring in a suitable solvent such as DCM in the presence of a suitable base such as Hunigs base or triethylamine. Alternatively where L is hydroxy the reaction can be carried out using a suitable coupling agent such as PyBOP or HATU or CDI with a suitable base such as Hunigs base or DBU in a suitable solvent such as DCM or THF. Compounds of formula (XV) are commercially available or are prepared using known literature procedures.

Compounds of formula (IV) where E is S can be prepared from compounds of formula (IV) where E is O as outlined in Scheme 7:

Scheme 7.

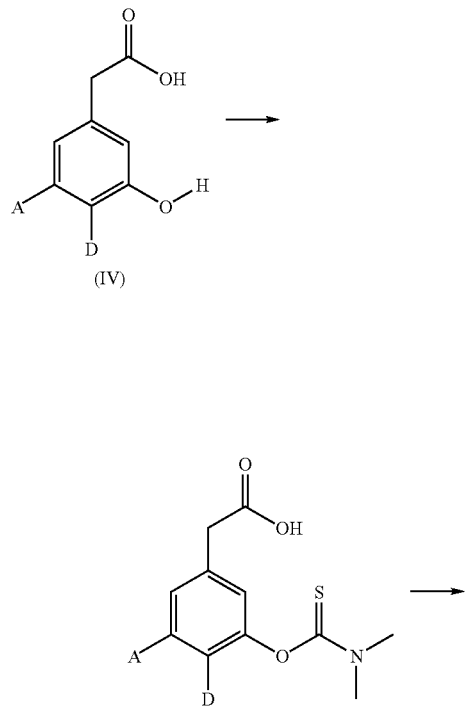

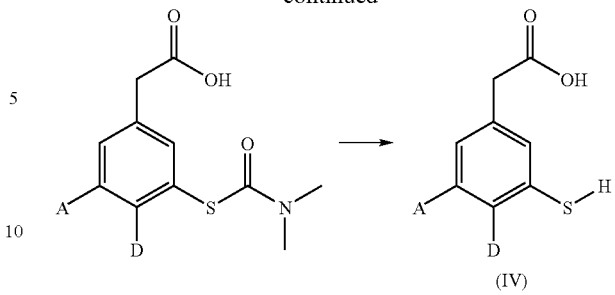

In which A and D are as defined in formula (I) or are protected derivatives thereof.

Compounds of formula (IV) undergo coupling with dimethylthiocarbamoyl chloride and subsequently rearrange on heating at elevated temperatures in a suitable solvent such as tetradecane or diphenylether. Compounds of formula (II) are obtained following hydrolysis with a suitable base such as sodium hydroxide.

Compounds of formula (I) in which A is CN, C$_{1-6}$ alkyl, aryl or heteroaryl can be prepared as outlined in Scheme 8:

Scheme 8.

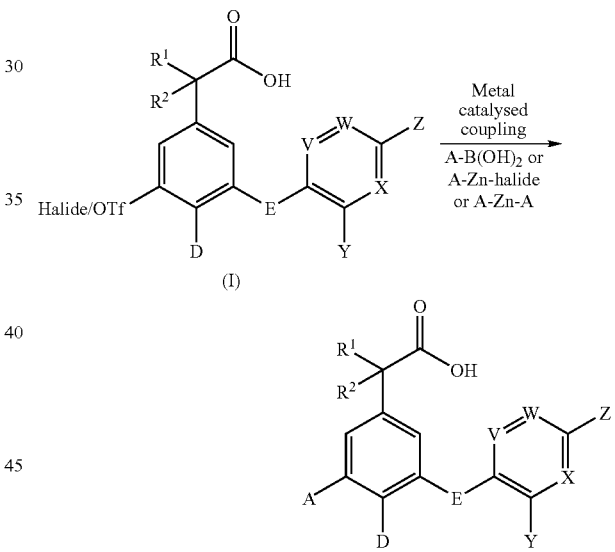

In which D, E, V, W, X, Y, Z, R$^1$ and R$^2$ are as defined in formula (I) or are protected derivatives thereof. The reaction is carried out using standard metal-catalysed coupling techniques. For example, the coupling reactions can be carried out by reacting compounds of formula (XVI) with an appropriate activated palladium catalyst such as bisdiphenylphosphino ferrocene palladium (II) and with the boronic acid adduct of A in the presence of a suitable base such as sodium carbonate or potassium carbonate or cesium carbonate in a suitable solvent such as toluene, THF or dioxane. The reactions are usually carried out at elevated temperatures, for example 80° C. Alternatively, the coupling reactions can be carried out by reacting compounds of formula (XVI) with an appropriate activated palladium catalyst such as bisdiphenylphosphinoferrocene palladium (II) and with the zinc adduct of A at elevated temperatures, for example 80° C., in a suitable solvent such as toluene, THF or dioxane.

Certain compounds of formula (I) in which A is OR³ can be prepared according to Scheme 9:

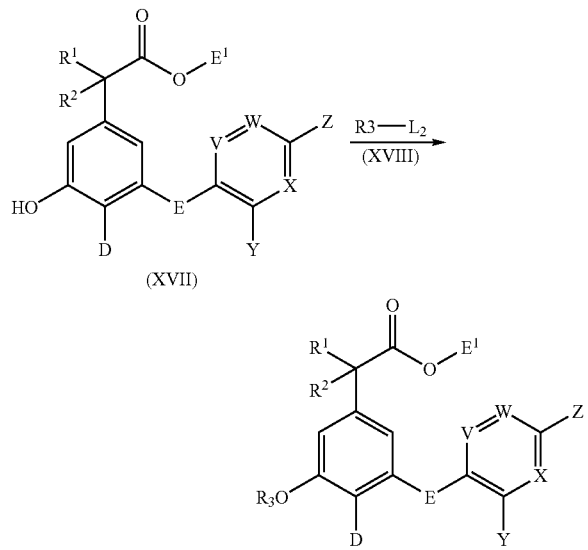

In which D, E, V, W, X, Y, Z, R¹ and R² are as defined in formula (I) or are protected derivatives thereof. E¹ is as defined in formula (II). L² is a suitable leaving group such as halogen or an activated alcohol such as mesylate or tosylate. Compounds of formula (I) are coupled with compounds of formula (XVIII) using a suitable base such as sodium carbonate or potassium carbonate or cesium carbonate in a suitable solvent such as acetonitrile or DMF. The ester group is subsequently removed as described above.

In a further aspect, the present invention provides the use of a compound of formula (I), a prodrug, pharmaceutically acceptable salt or solvate thereof for use in therapy.

The compounds of formula (I) or pharmaceutically acceptable slats thereof have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites.

A compound of the invention, or a pharmaceutically acceptable salt thereof, can be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. bone and joints: arthritides associated with or including osteoarthritis/osteoarthrosis, both primary and secondary to, for example, congenital hip is dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

3. pain and connective tissue remodelling of musculoskeletal disorders due to injury [for example sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

4. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. gastrointestinal tract: glossitis, gingivitis, periodontitis; oesophagitis, including reflux; eosinophilic gastro-enteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema);
7. abdominal: hepatitis, including autoimmune, alcoholic and viral; fibrosis and cirrhosis of the liver; cholecystitis; pancreatitis, both acute and chronic;
8. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);
9. allograft rejection: acute and chronic following, for example, transplantation of kidney, heart, liver, lung, bone marrow, skin or cornea or following blood transfusion; or chronic graft versus host disease;
10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes;
11. other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome;
12. other disorders with an inflammatory or immunological component; including acquired immune deficiency syndrome (AIDS), leprosy, Sezary syndrome, and paraneoplastic syndromes;
13. cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;
14. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and,
15. gastrointestinal tract: Coeliac disease, proctitis, eosinopilic gastro-enteritis, mastocytosis, Crohn's disease, ulcerative colitis, microscopic colitis, indeterminant colitis, irritable bowel disorder, irritable bowel syndrome, non-inflammatory diarrhea, food-related allergies which have effects remote from the gut, e.g., migraine, rhinitis and eczema.
16. Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy.

In a further aspect, the present invention provides the use of a compound or formula (I), or a pharmaceutically acceptable salt or solvate thereof, as hereinbefore defined in the manufacture of a medicament for use in therapy in combination with drugs used to treat asthma and rhinitis (such as inhaled and oral steroids, inhaled β2-receptor agonists and oral leukotriene receptor antagonists).

The invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumaroxcoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention, or a pharmaceutically acceptable salt thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY x 1005.

The present invention further relates to the combination of a compound of the invention, or a pharmaceutically acceptable salt thereof, and a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention, or a pharmaceutically acceptable salt thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, and a proton pump inhibitor (such as omeprazole) or a gastroprotective histamine type 2 receptor antagonist.

The present invention further relates to the combination of a compound of the invention, or a pharmaceutically acceptable salt thereof, and an antagonist of the histamine type 4 receptor.

The present invention still further relates to the combination of a compound of the invention, or a pharmaceutically acceptable salt thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, and an anticholinergic agents including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, and a chromone, such as sodium cromoglycate or nedocromil sodium.

The present invention still further relates to the combination of a compound of the invention, or a pharmaceutically acceptable salt thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, with an agent that modulates a nuclear hormone receptor such as PPARs.

The present invention still further relates to the combination of a compound of the invention, or a pharmaceutically acceptable salt thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, and an agent for the treatment of acute or chronic pain, such as a centrally or peripherally-acting analgesic (for example an opioid or derivative thereof), carbamazepine, phenyloin, sodium valproate, amitryptiline or other anti-depressant agent-s, paracetamol, or a non-steroidal anti-inflammatory agent.

The present invention further relates to the combination of a compound of the invention, or a pharmaceutically acceptable salt thereof, together with a parenterally or topically-applied (including inhaled) local anaesthetic agent such as lignocaine or a derivative thereof.

A compound of the present invention, or a pharmaceutically acceptable salt thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-$B_1$- or $B_2$-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin $NK_1$ or $NK_3$ receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2x7; or (xxvii) inhibitor of transcription factor activation such as NFkB, API, or STATS.

A compound of the invention, or a pharmaceutically acceptable salt thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD 1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy) quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The invention will now be illustrated by the following non-limiting examples in which, unless stated otherwise:

(i) when given, $^1$H NMR data is quoted in the form of delta values for major diagnostic protons, given in parts per million (ppm) relative to tetramethylsilane (TMS) as an internal standard;

(ii) mass spectra (MS): generally only ions which indicate the parent mass are reported, (MM)=MultiMode;

(iii) the title compounds of the examples and methods were named using the ACD/name and ACD/name batch (version 6.0) from Advanced Chemical Development Inc, Canada;

(iv) unless stated otherwise, reverse phase HPLC (RPHPLC) was conducted using a Symmetry, NovaPak or Ex-Terra reverse phase silica column;

(v) solvents were dried with $MgSO_4$ or $Na_2SO_4$; is (vi) reactions are carried out at room temperature unless otherwise stated;

(vii) the following abbreviations are used:
aq. Aqueous
BuLi Butyl lithium
HCl Hydrochloric acid
NBS N-Bromosuccinimide
DCM Dichloromethane
DMF N,N-dimethylformamide
Ether Diethyl ether
EtOAc Ethyl acetate
HBr Hydrogen bromide
MeI Methyl iodide
NMP 1-Methyl-2-pyrrolidone
THF Tetrahydrofuran
MCPBA 3-Chloroperoxybenzoic acid (Aldrich 77% max)
RT Room temperature

EXAMPLE 1

{4-chloro-3-[2-chloro-4-(methylsulfonyl)phenoxy]phenyl}acetic acid

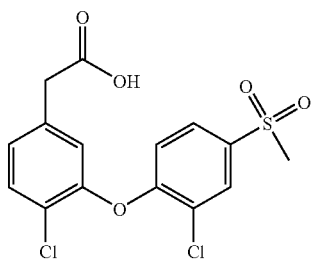

(i) 4-(Bromomethyl)-1-chloro-2-methoxybenzene

2-Chloro-5-methylphenol (20 g), $K_2CO_3$ (30 g), acetone (200 ml) and methyl iodide (9.4 ml) were charged to a flask and stirred for 24 h. The solvent was removed under reduced pressure and the residue partitioned between ether and water. The organics were separated, washed with 2 M sodium hydroxide, water, dried (MgSO$_4$) and evaporated under reduced pressure. The residue was dissolved in EtOAc, then NBS (25 g) and benzoyl peroxide (0.5 g) was added and the reaction mixture irradiated with a halogen lamp for 3 h. The solvent was removed under reduced pressure and the residue was purified by flash column chromatography (eluent isohexane) to give the subtitle compound (30 g) used directly without further purification or characterisation.

(ii) (4-Chloro-3-methoxyphenyl)acetic acid

The product from step (i), DMF (200 ml) and sodium cyanide (20 g) were charged to a flask and stirred for 2 h at RT. The residue was partitioned between ether and water; the organics were separated, washed with water, dried (MgSO$_4$) and evaporated under reduced pressure. Potassium hydroxide (40 g in water) was added and the mixture heated at reflux for 24 h. The reaction mixture was cooled to RT and extracted with ether. The aq layer was acidified to pH 1 with concentrated HCl and extracted with ethyl acetate. The organic layer was washed with water, dried (MgSO$_4$) and evaporated under reduced pressure. The residue was triturated with isohexane/ether, and then filtered to give the subtitle compound (12.2 g).

(iii) (4-Chloro-3-hydroxyphenyl)acetic acid

The product from step (ii) (12.2 g), HBr (48% aq.) and acetic acid (10 ml) were charged to a flask and heated at reflux for 24 h, cooled then evaporated under reduced pressure. The residue was triturated with ether/isohexane, and then filtered to give the subtitle compound (10.6 g).
$^1$H NMR CDCl$_3$-d6: δ 7.32 (1H, d), 6.85 (1H, s), 6.82 (1H, d), 3.9 (3H, s), 3.63 (2H, s).

(iv) Ethyl(4-chloro-3-hydroxyphenyl)acetate

The product of step (iii) (4 g) was added to a solution of acetyl chloride (10 ml) in ethanol (40 ml). The mixture was stirred for 1 h at RT then evaporated under reduced pressure. The residue was purified by flash column chromatography (eluent 2:1 isohexane/EtOAc) to give the subtitle compound (4.4 g).

(v) ethyl{4-chloro-3-[2-chloro-4-(methylsulfonyl) phenoxy]phenyl}acetate

The product from step (iv) (4.4 g), 3-chloro-4-fluorophenyl methyl sulfone (4.27 g), cesium carbonate (6.5 g) and NMP (40 ml) were charged to a flask and stirred at 90° C. for 2 h. The reaction was diluted with water, extracted with EtOAc, dried (MgSO$_4$) and evaporated under reduced pressure. The residue was purified by flash column chromatography (eluent 2:1 isohexane/ether) to give the subtitle compound (3.6 g).
MS: ESI−ve 401 (M−H).

(vi) {4-chloro-3-[2-chloro-4-(methylsulfonyl)phenoxy]phenyl}acetic acid

Sodium hydroxide (0.72 g) in water (40 ml) was added to the product from step (v) (3.6 g) in THF (40 ml) and stirred at RT overnight. The reaction was quenched with 2M HCl, extracted with EtOAc, dried (MgSO$_4$) and evaporated under reduced pressure. The residue was recrystallised from EtOAc/isohexane to give the subtitle compound (2.6 g).

$^1$H NMR DMSO-d6: δ 12.46 (1H, s), 8.15-8.14 (1H, s), 7.84 (1H, d), 7.63-7.59 (1H, d), 7.28-7.24 (2H, m), 6.93 (1H, d), 3.64 (2H, s), 3.27 (3H, s).
MS: ESI−ve 372 (M−H)

EXAMPLE 2

{4-chloro-3-[4-(methylsulfonyl)-2-(trifluoromethyl) phenoxy]phenyl}acetic acid

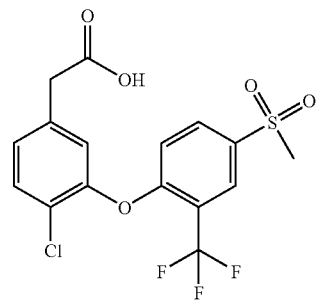

(i) 4-fluoro-3-(trifluoromethyl)phenyl methylsulfide

Isoamyl nitrite (1.13 ml) was added to a solution of diethyldisulfide (0.69 ml) 4-fluoro-3-(trifluoromethyl)aniline (1 g) in acetonitrile (50 ml). The solution was heated at reflux at 60° C. for 2 h, and then evaporated under reduced pressure. The residue was purified by flash column chromatography (eluent 2:1 isohexane/ether) to give the subtitle compound (0.57 g).
$^1$H NMR CDCl$_3$-d6: δ 7.41 (2H, m), 7.10 (1H, t), 2.5 (3H, s).

(ii) 4-fluoro-3-(trifluoromethyl)phenyl methylsulfone

MCPBA (1.1 g) was added to a solution of the product from step (i) (0.57 g) in DCM (20 ml) and stirred overnight. The solution was washed with aq sodium metabisulfite. The organic phase was dried (MgSO$_4$) and evaporated under reduced pressure, to give the subtitle compound (0.4 g).
$^1$H NMR CDCl$_3$-d6: δ 8.26-8.18 (2H, dd), 7.44 (1H, t), 3.10 (3H, s).

(iii) {4-chloro-3-[4-(methylsulfonyl)-2-(trifluoromethyl)phenoxy]phenyl}acetic acid The product of step (ii) (150 mg), the product of example 1 step (iii) (125 mg), cesium carbonate (437 mg) and NMP (10 ml) were charged to a flask and heated for 10 h at 80° C. The solution was acidified and extracted with ethyl acetate. The organic extracts were dried (MgSO$_4$) and evaporated under reduced pressure. The residue was purified by RPHPLC to give the title compound (117 mg).

$^1$H NMR DMSO-d6: δ 12.48 (1H, s), 8.27 (1H, s), 8.16-8.14 (1H, d), 7.66-7.64 (1H, d), 7.33-7.31 (2H, m), 6.96 (1H, d), 3.67 (2H, s), 3.31 (3H, s).
MS: APCI−ve 407 (M−H).

EXAMPLE 3

{4-chloro-3-[2-chloro-4-(ethylsulfonyl)phenoxy]phenyl}acetic acid

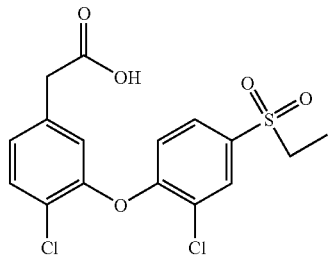

(i) 3-chloro-4-fluorophenyl ethyl sulfone 3-chloro-4-fluorobenzenethiol (10 g), iodoethane (4.9 ml), potassium carbonate (8.51 g) and DMF (40 ml) were charged to a flask and stirred for 2 h. The residue was partitioned between ether and water, the organics were separated then dried (MgSO$_4$) and evaporated under reduced pressure. The residue was dissolved in DCM (100 ml), cooled to 0° C., MCPBA (26.5 g) was added. The reaction mixture was stirred overnight then diluted with DCM, washed with aq sodium metabisulfite, sodium hydrogen carbonate then dried (MgSO$_4$) and evaporated under reduced pressure. The residue was purified by flash column chromatography (eluent 1:1 isohexane/ether) to give the subtitle compound (9.5 g).
$^1$H NMR CDCl$_3$-d6: δ 7.99 (1H, d), 7.79-7.84 (1H, m), 7.37-7.31 (1H, m), 3.12 (2H, q), 1.33-1.26 (3H, t).

(ii) {4-chloro-3-[2-chloro-4-(ethylsulfonyl)phenoxy]phenyl}acetic acid

The title compound was prepared by the method of example 2 step (iii) using the product of step (i) and the product of example 1 step (iii).
$^1$H NMR DMSO-d6: δ 8.1 (1H, s), 7.81 (1H, dd), 7.6 (1H, d), 7.28-7.25 (2H, m), 6.95-6.92 (1H, d), 3.62 (2H, s), 3.42-3.32 (2H, q), 1.47-1.07 (3H, t).
MS: ESI-ve 386 (M-H).

EXAMPLE 4

{4-chloro-3-[4-(ethylsulfonyl)-2-(trifluoromethyl)phenoxy]phenyl}acetic acid

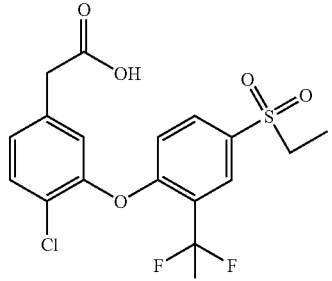

(i) ethyl 4-fluoro-3-(trifluoromethyl)phenyl sulfide

The subtitle compound was prepared by the method of example 2 steps (i) and (ii).
$^1$H NMR CDCl$_3$-d6: δ 7.51 (2H, dd), 7.13 (1H, t), 2.95 (2H, q), 1.28 (3H, t).

(ii) {4-chloro-3-[4-(ethylsulfonyl)-2-(trifluoromethyl)phenoxy]phenyl}acetic acid The title compound was prepared by the method of example 2 step (iii) using the product of step (i) and the product of example 1 step (iii).
$^1$H NMR DMSO-d6: δ 8.19 (1H, s), 8.11 (1H, d), 7.6 (1H, d), 7.29 (2H, m), 6.97-6.95 (1H, d), 3.52 (2H, s), 3.43-3.36 (2H, q), 1.15-1.05 (3H, t).
MS: ESI-ve 421 (M-H).

EXAMPLE 5

{4-chloro-3-[4-(methylsulfonyl)phenoxy]phenyl}acetic acid

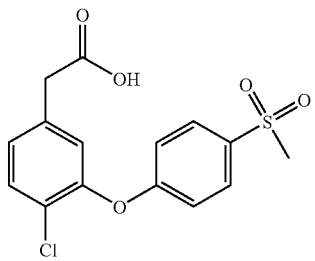

The title compound was prepared by the method of example 2 step (iii) using the product of example 1 step (iii) and 4-fluorophenyl methyl sulfone.
$^1$H NMR DMSO-d6: δ 7.93-7.89 (2H, m), 7.59-7.54 (1H, m), 7.23-7.06 (4H, m), 3.52 (2H, s), 3.18 (3H, s).
MS: APCI-ve 339 (M-H).

EXAMPLE 6

2-{4-chloro-3-[2-chloro-4-(methylsulfonyl)phenoxy]phenyl}propanoic acid

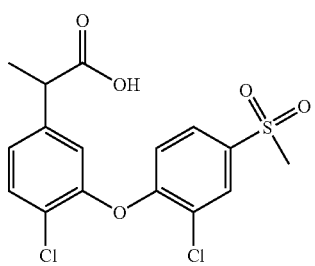

(i) methyl(4-chloro-3-methoxyphenyl)acetate

The product of example 1 step (iii) (1 g), dimethyl sulfate (1 ml), potassium carbonate (1.48 g) and acetone (20 ml) were charged to a flask and heated at reflux for 16 h. The reaction was diluted with water, extracted with EtOAc, dried (MgSO₄) and evaporated under reduced pressure to give the subtitle compound (1.5 g).

¹H NMR CDCl₃-d6: δ 7.31-7.26 (1H, m), 6.86-6.79 (2H, m), 3.9 (3H, s), 3.73 (3H, s), 3.59 (2H, s).

(ii) methyl 2-(4-chloro-3-methoxyphenyl)propanoate

The product of step (i) (0.5 g) was added to a solution of nBuLi (1.75 ml, 1.6 M in THF) and diisopropylamine (0.4 ml) in THF (10 ml) at −78° C. and stirred for 1 h, then methyl iodide (0.18 ml) was added, stirred for 1 h at −78° C. then at room temperature for 1 h and quenched with water. The product was extracted with ether, dried (MgSO₄) and evaporated under reduced pressure. The residue was purified by flash column chromatography (eluent 1:1 isohexane/ether) to give the subtitle compound (0.21 g).

¹H NMR CDCl₃-d6: δ 7.3-7.26 (1H, m), 6.87-6.81 (2H, m), 3.9 (3H, s), 3.67 (3H, s), 3.48 (1H, q), 1.47 (3H, d).

(iii) methyl 2-(4-chloro-3-hydroxyphenyl)propanoate

48% aqueous HBr (10 ml) was added to the product of step (ii) (0.21 g) in acetic acid (10 ml) and heated at 100° C. for 10 h.

MS: ESI−ve 199 (M−H).

(iv) 2-{4-chloro-3-[2-chloro-4-(methylsulfonyl)phenoxy]phenyl}propanoic acid

The title compound was prepared by the method of example 2 step (iii) using the product of step (iii) and 3-chloro-4-fluorophenyl methyl sulfone.

¹H NMR DMSO-d6: δ 8.14 (1H, s), 7.82 (1H, d), 7.61 (1H, d), 7.27 (2H, m), 6.88 (1H, d), 3.71 (1H, q), 3.26 (3H, s), 1.34 (3H, d).

MS: APCI−ve 387 (M−H).

EXAMPLE 7

(4-chloro-3-{2-chloro-4-[(dimethylamino)sulfonyl]phenoxy}phenyl)acetic acid

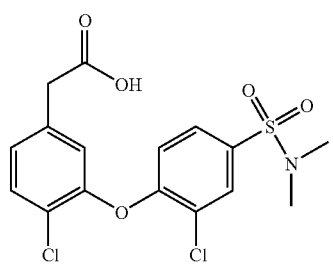

The title compound was prepared by the method of example 2 step (iii) using 3-chloro-4-fluoro-N,N-dimethylbenzenesulfonamide and the product of example 1 step (iii).

¹H NMR DMSO-d6: δ 7.93 (1H, s), 7.7 (2H, m), 7.24 (2H, m), 6.93 (1H, d), 3.61 (2H, s), 2.64 (6H, s).

MS: APCI−ve 401 (M−H).

EXAMPLE 8

[4-chloro-3-(3-cyanophenoxy)phenyl]acetic acid

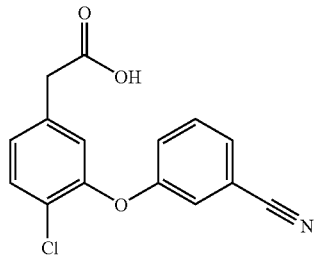

The product from example 1 step (iii) (0.5 g), 3-bromobenzonitrile (0.73 g), cesium carbonate (2.61 g), copper(I) chloride (0.13 g), 2,2,6,6-tetramethyl-3,5-heptanedione (0.06 ml) and NMP (10 ml) were charged to a flask and heated at 120° C. for 16 h. The mixture was partitioned between ether and 2M NaOH, the aqueous layer was acidified then extracted with EtOAc, dried (MgSO₄) and evaporated under reduced pressure. The residue was purified by RPHPLC to give the title compound (0.015 g).

¹H NMR DMSO-d6: δ 7.57-7.42 (4H, m), 7.28-7.12 (3H, m), 3.46 (2H, s).

MS: APCI−ve 286 (M−H).

EXAMPLE 9

{4-chloro-3-[2-fluoro-4-(methylsulfonyl)phenoxy]phenyl}acetic acid

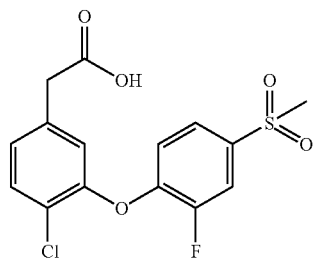

The title compound was prepared by the method of example 2 step (iii) using 3,4-difluorophenyl methyl sulfone and the product of example 1 step (iii).

¹H NMR DMSO-d6: δ 7.98 (1H, d), 7.7 (1H, d), 7.54 (1H, d), 7.2 (2H, m), 7.01 (1H, t), 7.06 (1H, s), 3.27 (3H, s), 3.48 (2H, s).

MS: APCI−ve 357 (M−H).

EXAMPLE 10

{4-chloro-3-[4-(ethylsulfonyl)-2-fluorophenoxy]phenyl}acetic acid

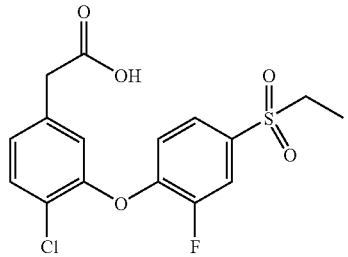

(i) 3,4-difluorophenyl ethyl sulfide

A solution of 3,4-difluorothiophenol (3 g), ethyl iodide (1.6 ml), potassium carbonate (2.64 g) and DMF (40 ml) were charged to a flask and stirred for 2 h. The solution was partitioned between ethyl acetate and water. The organic extracts were dried (MgSO$_4$) and evaporated under reduced pressure to give the subtitle compound (3.84 g).

$^1$H NMR CDCl$_3$-d6: δ 7.19-7.032 (3H, m), 2.95 (2H, q), 1.29 (3H, t).

(ii) 3,4-difluorophenyl ethyl sulfone

The subtitle compound was prepared by the method of example 2 step (ii) using the product of step (i).

$^1$H NMR CDCl$_3$-d6: δ 7.75 (2H, m), 7.4 (1H, q), 3.15 (2H, q), 1.33 (3H, t).

(iii) {4-chloro-3-[4-(ethylsulfonyl)-2-fluorophenoxy]phenyl}acetic acid

The title compound was prepared by the method of example 2 step (iii) using the product of step (ii) and the product of example 1 step (iii).

$^1$H NMR DMSO-d6: δ 7.93 (1H, d), 7.6 (2H, m), 7.23-7.21 (2H, m), 7.04 (1H, t), 3.55 (2H, s), 3.35 (2H, q), 1.1 (3H, t).
MS: APCI−ve 371 (M−H).

EXAMPLE 11

{4-chloro-3-[2-cyano-4-(methylsulfonyl)phenoxy]phenyl}acetic acid

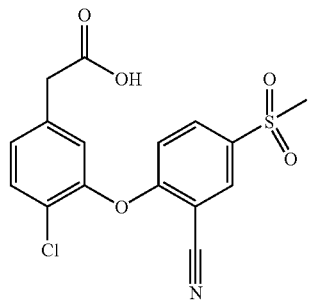

(i) 2-chloro-5-(methylsulfonyl)benzonitrile

The subtitle compound was prepared by the methods of example 2 steps (i) and (ii) using 5-amino-2-chlorobenzonitrile and dimethyldisulfide.

$^1$H NMR CDCl$_3$-d6: δ 8.26 (1H, s), 8.09 (1H, d), 7.76 (1H, d), 3.1 (3H, s).

(ii) {4-chloro-3-[2-cyano-4-(methylsulfonyl)phenoxy]phenyl}acetic acid

The title compound was prepared by the method of example 2 step (iii) using the product of step (i) and the product of example 1 step (iii).

$^1$H NMR DMSO-d6: δ 8.48 (1H, s), 8.11 (1H, d), 7.58 (1H, d), 7.37-7.27 (2H, m), 6.9 (1H, d), 3.46 (2H, s), 3.26 (3H, s).
MS: APCI−ve 364 (M−H).

EXAMPLE 12

{4-chloro-3-[2-cyano-4-(ethylsulfonyl)phenoxy]phenyl}actic acid

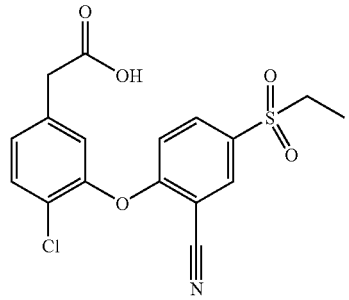

(i) 2-chloro-5-(ethylsulfonyl)benzonitrile

The subtitle compound was prepared by the methods of example 2 steps (i) and (ii) using 5-amino-2-chlorobenzonitrile and diethyldisulfide.

$^1$H NMR CDCl$_3$-d6: δ 8.21 (1H, s), 8.05 (1H, d), 7.75 (1H, d), 3.6 (2H, q), 1.32 (3H, t).

(ii) {4-chloro-3-[2-cyano-4-(ethylsulfonyl)phenoxy]phenyl}acetic acid

The title compound was prepared by the method of example 2 step (iii) using the product of step (i) and the product of example 1 step (iii).

$^1$H NMR DMSO-d6: δ 8.43 (1H, s), 8.07 (1H, d), 7.59 (1H, d), 7.39-7.21 (2H, m), 6.9 (1H, d), 3.49 (2H, s), 3.35 (2H, q), 1.09 (3H, t).
MS: APCI−ve 378 (M−H).

EXAMPLE 13

{4-chloro-3-[4-(methylsulfonyl)-3-(trifluoromethyl)phenoxy]phenyl}acetic acid

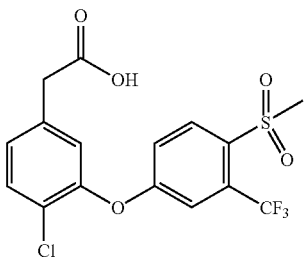

(i) 4-fluoro-3-(trifluoromethyl)phenylmethyl sulfone

The subtitle compound was prepared by the methods of example 2 steps (i) and (ii) using 4-fluoro-3-(trifluoromethyl)aniline and dimethyldisulfide.

¹H NMR CDCl₃-d6: δ 8.22 (2H, d), 7.44 (1H, t), 3.1 (3H, s).

(ii) {4-chloro-3-[4-(methylsulfonyl)-3-(trifluoromethyl)phenoxy]phenyl}acetic acid The title compound was prepared by the method of example 2 step (iii) using the product of step (i) and the product of example 1 step (iii).

¹H NMR DMSO-d6: δ 8.19 (1H, d), 7.56-7.55 (2H, m), 7.28-7.23 (3H, m), 3.43 (2H, s), 3.26 (3H, s).

MS: APCI–ve 407 (M–H).

EXAMPLE 14

{4-chloro-3-[2-cyano-5-(trifluoromethyl)phenoxy]phenyl}acetic acid

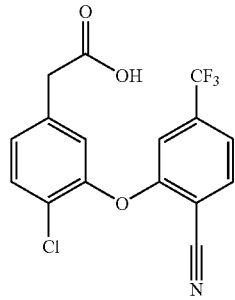

The title compound was prepared by the method of example 2 step (iii) using 3-fluoro-4-(trifluoromethyl)benzonitrile and the product of example 1 step (iii).

¹H NMR DMSO-d6: δ 8.22 (1H, d), 7.7 (2H, d), 7.36-7.27 (2H, m), 7 (1H, s), 3.59 (2H, s).

MS: APCI–ve 354 (M–H).

EXAMPLE 15

(4-chloro-3-{2-fluoro-4-[(4-fluorobenzyl)sulfonyl]phenoxy}phenyl)acetic acid

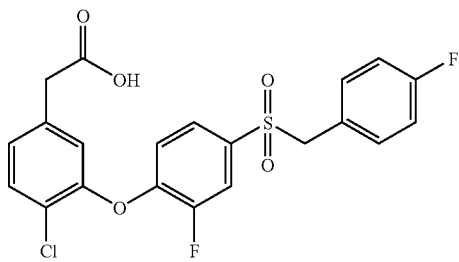

(i) 3,4-difluorophenyl 4-fluorophenyl sulfone

The subtitle compound was prepared by the method of example 10 step (i) and example 2 step (ii) using 3,4-difluorobenzenethiol and 1-(bromomethyl)-4-fluorobenzene.

¹H NMR CDCl₃-d6: δ 7.51-7.46 (1H, m), 7.41-7.37 (1H, m), 7.29-7.23 (1H, m), 7.12-7.00 (4H, m), 4.29 (2H, s).

(ii) (4-chloro-3-{2-fluoro-4-[(4-fluorobenzyl)sulfonyl]phenoxy}phenyl)acetic acid The title compound was prepared by the method of example 2 step (iii) using the product of step (i) and the product of example 1 step (iii).

¹H NMR DMSO-d6: δ 7.79 (1H, d), 7.6 (1H, d), 7.48 (1H, d), 7.25-7.14 (6H, m), 7.03-6.98 (1H, t), 4.75 (2H, s), 3.57 (2H, s).

MS: APCI–ve 451 (M–H).

EXAMPLE 16

[3-(4-benzoyl-2-fluorophenoxy)-4-chlorophenyl]acetic acid

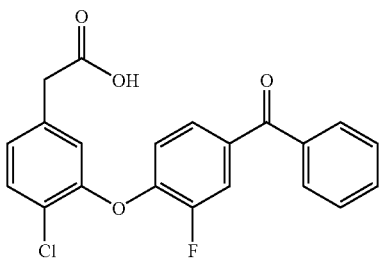

The title compound was prepared by the method of example 2 step (iii) using the product of step (i) and 3,4-difluorobenzophenone.

¹H NMR DMSO-d6: δ 7.70-7.75 (1H, d), 7.-6-7.57 (1H, d), 7.48-7.44 (1H, d), 7.25-7.14 (6H, m), 7.03-6.98 (1H, t), 4.75 (2H, s), 3.57 (2H, s).

MS: APCI–ve 385 (M–H).

EXAMPLE 17

(4-chloro-3-{2-chloro-4-[(isobutylamino)carbonyl]phenoxy}phenyl)acetic acid

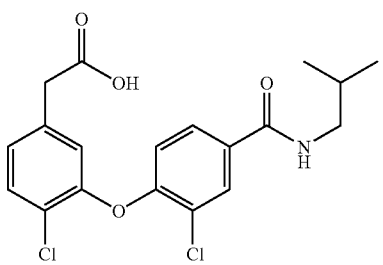

(i) 3-chloro-4-fluoro-N-isobutylbenzamide

Isobutyl amine (2 molar equivalent) was added to a solution of 3-chloro-4-fluorobenzoyl chloride (1 g) in DCM (10 ml) and stirred for 2 h. The reaction was diluted with DCM, washed with water, dried (MgSO₄) and evaporated under reduced pressure to give a white solid (1.2 g).

MS: ESI+ve 230 (M+H).

(ii) (4-chloro-3-{2-chloro-4-[(isobutylamino)carbonyl]phenoxy}phenyl)acetic acid The title compound was prepared by the method of example 2 step (iii) using the product of step (i) and the product of example 1 step (iii).

$^1$H NMR DMSO-d6: δ 8.53 (1H, t), 8.07 (1H, s), 7.8 (1H, d), 7.57 (1H, d), 7.17 (1H, d), 7.06 (1H, s), 6.88 (1H, d), 3.58 (2H, s), 3.08 (2H, t), 1.82 (1H, q), 0.88 (6H, d).

MS: APCI−ve 396 (M+H).

EXAMPLE 18

{3-chloro-5-[2-chloro-4-(methylsulfonyl)phenoxy]phenyl}acetic acid

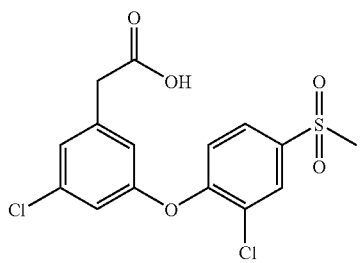

(i) 3-chloro-5-methoxybenzoic acid

Sodium methoxide (25% wt., 7 ml) was added to a stirred solution of 3,5-dichlorobenzoic acid (2 g) in DMPU (10 ml) and heated at 170° C. for 5 days. The reaction was poured onto 1M HCl (50 ml). The resulting solid formed was filtered and washed with water, then dried in vacuo to give the subtitle compound (0.8 g).

$^1$H NMR DMSO-d6: δ 13.34 (1H, s), 7.46 (1H, s), 7.38 (1H, s), 7.3 (1H, s), 3.77 (3H, s).

(ii) (3-chloro-5-methoxyphenyl)methanol

Lithium aluminium hydride (1M in THF, 8.76 ml) was added dropwise to a stirred solution of the product of step (i) (1.63 g) in THF (40 ml) and stirred for 2 h. The reaction was diluted with 2 M HCl and extracted with ethyl acetate. The organic layer was washed with aqueous sodium hydrogen carbonate, dried (MgSO$_4$) and evaporated under reduced pressure to give the subtitle compound (1.53 g).

$^1$H NMR CDCl$_3$-d6: δ 6.93 (1H, s), 6.82-6.71 (2H, m), 4.63 (2H, s), 3.79 (3H, s).

(iii) (3-chloro-5-methoxyphenyl)acetonitrile

Phosphorous tribromide (0.28 ml) was added to a solution of the product of step (ii) (1.55 g) in ether (20 ml) at 0° C., then stirred for 30 min. The reaction mixture was partitioned between ether and aqueous sodium hydrogen carbonate, the organics were separated then dried (MgSO$_4$) and evaporated under reduced pressure. The residue was dissolved in DMF (20 ml) and sodium cyanide (0.5 g) was added. The mixture was stirred overnight then partitioned between ether and water; the organics were separated, washed with aqueous sodium hydrogen carbonate then dried (MgSO$_4$) and evaporated under reduced pressure. The residue was purified by flash column chromatography (eluent 1:1 ether/isohexane) to give the subtitle compound (0.53 g).

$^1$H NMR CDCl$_3$-d6: δ 6.91-6.9 (1H, m), 6.86-6.85 (1H, m), 6.77-6.76 (1H, m), 3.79 (3H, s), 3.69 (2H, s).

(iv) (3-chloro-5-hydroxyphenyl)acetic acid

The product of step (iii) (0.53 g), tetrabutylammonium chloride (0.123 g) and 48% aqueous HBr (10 ml) were charged to a flask and heated at 125° C. for 36 h. The reaction mixture was partitioned between water and ethyl acetate, the organics were separated then dried (MgSO$_4$) and evaporated under reduced pressure.

$^1$H NMR DMSO-d6: δ 12.33 (1H, s), 9.87 (1H, s), 6.75-6.65 (3H, m), 3.50 (2H, s).

(v) {3-chloro-5-[2-chloro-4-(methylsulfonyl)phenoxy]phenyl}acetic acid

The title compound was prepared by the method of example 2 step (iii) using the product of step (iv) and 3-chloro-4-fluorophenyl methyl sulfone.

$^1$H NMR DMSO-d6: δ 8.14 (1H, s), 7.87 (1H, d), 7.33-7.02 (4H, m), 3.62 (2H, s), 3.27 (3H, s).

MS: APCI+ve 392 (M+NH$_4$).

EXAMPLE 19

{3-chloro-5-[2-chloro-4-(ethylsulfonyl)phenoxy]phenyl}acetic acid

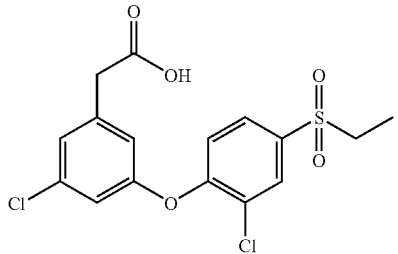

The title compound was prepared by the method of example 2 step (iii) using the product of example 3 step (i) and the product of example 18 step (iv).

$^1$H NMR DMSO-d6: δ 8.07 (1H, s), 7.82 (1H, d), 7.2 (3H, m), 7.03 (1H, s), 3.59 (2H, s), 3.35 (2H, q), 1.1 (3H, t).

MS: APCI−ve 386 (M−H).

EXAMPLE 20

{3-[2-chloro-4-(ethylsulfonyl)phenoxy]-5-fluorophenyl}acetic acid

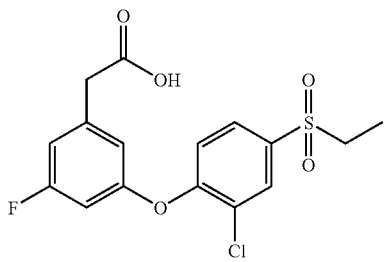

(i) 3-fluoro-5-methoxybenzoic acid

The subtitle compound was prepared by the method of example 18 step (i) using 3,5-difluoro-benzoic acid.
MS: APCI−ve 169 (M−H).

(ii) (3-fluoro-5-methoxyphenyl)methanol

The subtitle compound was prepared by the method of example 18 step (ii) using the product of step (i)
$^1$H NMR CDCl$_3$-d6: δ 6.68 (2H, m), 6.53 (1H, m), 4.67 (2H, d), 3.8 (3H, s).

(iii) (3-fluoro-5-methoxyphenyl)acetonitrile

Thionyl chloride (0.95 ml) was added to a solution of the product of step (ii) (0.95 ml) in DCM (20 ml) at 0° C., then stirred for 1 h. The reaction mixture was washed with 2M HCl, the organics were separated then dried (MgSO$_4$) and evaporated under reduced pressure. The residue was dissolved in DMF (10 ml) and sodium cyanide (0.3 g) was added. The mixture was stirred for 2 h, then partitioned between ether and water; the organics were separated, then dried (MgSO$_4$) and evaporated under reduced pressure. The residue was purified by flash column chromatography (eluent 1:1 ether/isohexane) to give the subtitle compound (0.47 g).
$^1$H NMR CDCl$_3$-d6: δ 6.66 (3H, m), 3.81 (3H, s), 3.70 (2H, s).

(iv) (3-fluoro-5-hydroxyphenyl)acetic acid

The subtitle compound was prepared by the method of example 18 step (iv) using the product of step (iii)
$^1$H NMR DMSO-d6: δ 12.10 (1H, s), 9.79 (1H, s), 6.42 (3H, m), 3.44 (2H, s).

(v) {3-[2-chloro-4-(ethylsulfonyl)phenoxy]-5-fluorophenyl}acetic acid

The title compound was prepared by the method of example 2 step (iii) using the product of step (iv) and the product of example 3 step (i).
$^1$H NMR DMSO-d6: δ 8.07 (1H, m), 7.82 (1H, d), 7.22 (1H, d), 7.03-6.89 (3H, m), 3.58 (2H, s), 3.32 (2H, q), 1.12 (3H, t).
MS: APCI−ve 371 (M−H).

EXAMPLE 21

{3-fluoro-5-[4-(methylsulfonyl)-2-(trifluoromethyl)phenoxy]phenyl}acetic acid

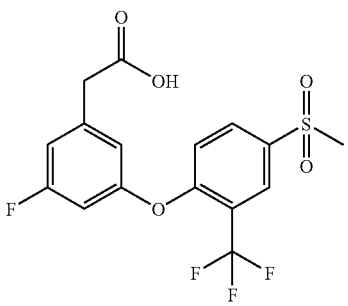

The title compound was prepared by the method of example 2 step (iii) using the product of example 2 step (ii) and the product of example 20 step (iv).
$^1$H NMR DMSO-d6: δ 8.23 (1H, s), 8.15 (1H, d), 7.23 (1H, d), 7.01 (3H, m), 3.51 (2H, s), 3.3 (3H, s).
MS: APCI−ve 391 (M−H).

EXAMPLE 22

{3-[2-chloro-4-(ethylsulfonyl)phenoxy]-4-fluorophenyl}acetic acid

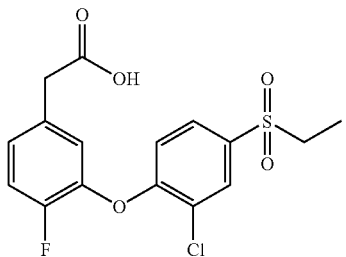

(i) 4-fluoro-3-methoxy-benzoic acid

The subtitle compound was prepared by the method of example 1 step (i) using 4-fluoro-3-hydroxybenzoic acid.
MS: APCI−ve 169 (M−H).

(ii) 2-fluoro-5-(hydroxymethyl)phenol

The subtitle compound was prepared by the method of example 18 step (ii) using the product of step (i).
$^1$H NMR CDCl$_3$-d6: δ 7.07-6.98 (2H, m), 6.88-6.80 (1H, m), 4.6 (2H, s), 3.89 (3H, s).

(iii) (4-fluoro-3-hydroxyphenyl)acetonitrile

The subtitle compound was prepared by the method of example 20 step (iii) using the product of step (ii).
$^1$H NMR CDCl$_3$-d6: δ 7.11 (1H, m), 7.03 (1H, m), 6.86 (1H, m), 3.91 (3H, s), 3.72 (2H, s).

(iv) (4-fluoro-3-hydroxyphenyl)acetic acid

The subtitle compound was prepared by the method of example 18 step (iv) using the product of step (iii).
¹H NMR DMSO-d6: δ 7.06-7.0 (2H, m), 6.88-6.83 (1H, m), 4.65-4.63 (2H, d), 3.89 (3H, s).

(v) {3-[2-chloro-4-(ethylsulfonyl)phenoxy]-4-fluorophenyl}acetic acid

The title compound was prepared by the method of example 2 step (iii) using the product of step (iv) and the product of example 3 step (i).
¹H NMR DMSO-d6: δ 8.07 (1H, s), 7.79 (1H, d), 7.4-7.35 (1H, m), 7.26-7.2 (2H, m), 7.03 (1H, d), 3.50 (2H, s), 3.36 (2H, q), 1.09 (3H, t)
MS: APCI–ve 371 (M–H).

EXAMPLE 23

{4-fluoro-3-[4-(methylsulfonyl)-2-(trifluoromethyl)phenoxy]phenyl}acetic acid

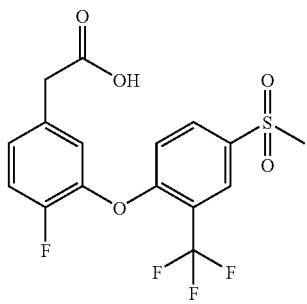

The title compound was prepared by the method of example 2 step (iii) using the product of example 22 step (iv) and the product of example 2 step (ii).
¹H NMR DMSO-d6: δ 8.24 (1H, s), 7.39-7.21 (3H, m), 7.10-7.07 (1H, d), 3.3 (3H, s).
MS: APCI–ve 391 (M–H).

EXAMPLE 24

{4-chloro-3-[2-fluoro-4-(phenylsulfonyl)phenoxy]phenyl}acetic acid

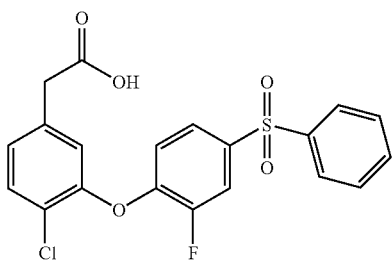

(i) 3,4-difluorophenyl phenyl sulfone 3,4-difluoroaniline (3.5 g), acetonitrile (60 ml), diphenyldisulfide (6 g) and isoamyl nitrite (8 ml) were charged to a flask and heated at 60° C. for 2 h then evaporated under reduced pressure. The residue was purified by flash column chromatography (eluent isohexane) to give the subtitle compound. The product (3,4-difluorophenyl phenyl sulfide) was dissolved in acetonitrile (60 ml). Water (10 ml) and oxone (20 g) were added and stirred for 72 h at RT. The reaction mixture was partitioned between ether/water, the organics were separated, washed with water, then dried (MgSO₄) and evaporated under reduced pressure. The residue was purified by flash column chromatography (eluent 5-10% ethyl acetate/isohexane) to give the subtitle compound (2.14 g).
¹H NMR CDCl₃-d6: δ 7.93 (2H, d), 7.81-7.71 (2H, m), 7.64-7.51 (3H, m), 7.34-7.28 (1H, m).

(ii) {4-chloro-3-[2-fluoro-4-(phenylsulfonyl)phenoxy]phenyl}acetic acid

The title compound was prepared by the method of example 2 step (iii) using the product of step (i) and the product of example 1 step (iii).
¹H NMR DMSO-d6: δ 8.07-7.99 (3H, m), 7.78-7.51 (5H, m), 7.21-7.19 (2H, m), 6.93 (1H, t), 3.43 (2H, s).
MS: APCI–ve 419 (M–H).

EXAMPLE 25

[3-[2-chloro-4-(methylsulfonyl)phenoxy]-5-(trifluoromethyl)phenyl]acetic acid

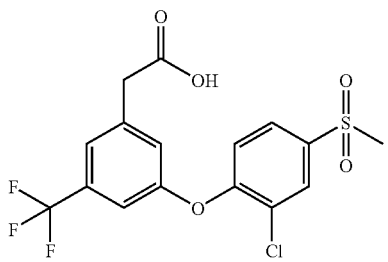

(i) 3-methoxy-5-(trifluoromethyl)benzoic acid

The subtitle compound was prepared by the method of example 1 step (i) using 3-fluoro-5-(trifluoromethyl)benzoic acid.
MS: APCI–ve 219 (M–H).

(ii) [3-methoxy-5-(trifluoromethyl)phenyl]methanol

The subtitle compound was prepared by the method of example 18 step (ii) using the product of step (i).
¹H NMR CDCl₃-d6: δ 7.26-7.04 (3H, m), 4.72 (2H, s), 4.08 (3H, s).

(iii) [3-methoxy-5-(trifluoromethyl)phenyl]acetonitrile

Triethylamine (2.04 ml) was added to a solution of the product of step (ii) (3.02 g) in DCM (30 ml) and cooled to 0° C. before adding methane sulfonyl chloride (1.13 ml). The reaction mixture was stirred for 2 h at RT. The reaction mixture was diluted with water, extracted with DCM then dried (MgSO₄) and evaporated under reduced pressure to give an oil. The oil was dissolved in DMF (20 ml), sodium cyanide (1.07 g) was added and stirred at 100° C. for 2 h. The reaction mixture was diluted with water, extracted with ether, dried (MgSO$_4$) and evaporated under reduced pressure. The residue was purified by flash column chromatography (eluent ether) to give the subtitle compound (1.9 g).

$^1$H NMR CDCl$_3$-d6: δ 7.16-7.06 (3H, m), 3.87 (3H, s), 3.78 (2H, s).

(iv) [3-hydroxy-5-(trifluoromethyl)phenyl]acetic acid

The subtitle compound was prepared by the method of example 18 step (iv) using the product of step (iii).

$^1$H NMR DMSO-d6: δ 7.02-6.83 (3H, m), 3.60 (2H, s).

(v) [3-[2-chloro-4-(methylsulfonyl)phenoxy]-5-(trifluoromethyl)phenyl]acetic acid The title compound was prepared by the method of example 2 step (iii) using the product of step (iv) and 3-chloro-4-fluorophenyl methyl sulfone.

$^1$H NMR DMSO-d6: δ 8.16 (1H, s), 7.89 (1H, d), 7.53 (1H, s), 7.37-7.23 (3H, m), 3.65 (2H, s), 3.29 (3H, s).

MS: APCI−ve 407 (M−H).

EXAMPLE 26

[3-[2-chloro-4-(ethylsulfonyl)phenoxy]-5-(trifluoromethyl)phenyl]acetic acid

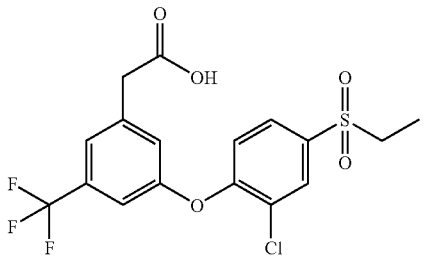

The title compound was prepared by the method of example 2 step (iii) using the product of example 25 step (iv) and the product of example 3 step (i).

$^1$H NMR DMSO-d6: δ 8.09 (1H, s), 7.83 (1H, d), 7.54-7.17 (4H, m), 3.70 (2H, s), 3.37 (2H, q), 1.12 (3H, t).

MS: APCI−ve 421 (M−H).

EXAMPLE 27

{3-chloro-5-[2-fluoro-4-(methylsulfonyl)phenoxy]phenyl}acetic acid

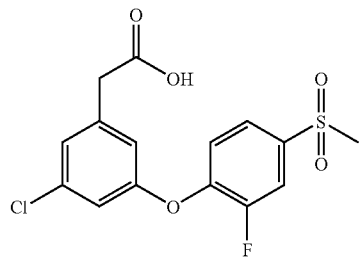

The title compound was prepared by the method of example 2 step (iii) using 3,4-difluorophenyl methyl sulfone and the product of example 18 step (iv).

$^1$H NMR DMSO-d6: δ 7.81 (1H, dd), 7.71 (1H, d), 7.15 (2H, s), 6.96 (1H, d), 6.89 (1H, s), 3.61 (2H, s), 3.09 (3H, s).

MS: APCI−ve 343 (M-CH$_3$).

EXAMPLE 28

{3-chloro-5-[2-cyano-4-(ethylsulfonyl)phenoxy]phenyl}acetic acid

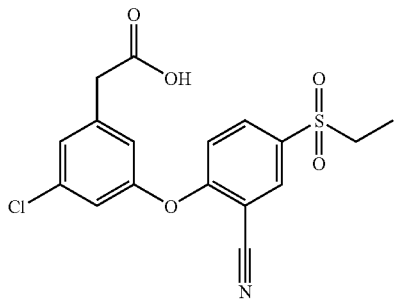

The title compound was prepared by the method of example 2 step (iii) using the product of example 12 step (ii) and the product of example 18 step (iv).

$^1$H NMR DMSO-d6: δ 8.41 (1H, d), 8.08 (1H, dd), 7.40 (1H, dd), 7.37 (1H, dd), 7.21 (1H, d), 7.13 (1H, d), 3.66 (2H, s), 3.37 (2H, q) and 1.12 (3H, t).

MS: APCI−ve 334 (M-CO$_2$).

EXAMPLE 29

{3-chloro-5-[2-chloro-4-(phenylsulfonyl)phenoxy]phenyl}acetic acid

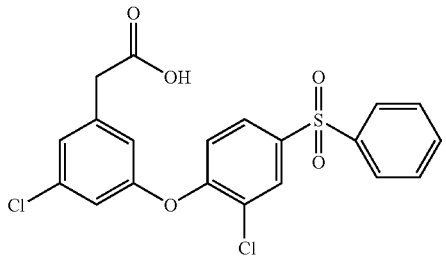

(i) 3-chloro-4-fluorophenyl phenyl sulfone

Ferric chloride (0.47 g), was added to a stirred mixture of 3-chloro-4-fluorosulfonyl chloride (1.5 g) and benzene (10 ml). The reaction mixture was then heated to reflux for 18 h, then allowed to cool to room temperature. The solvent was evaporated in vacuo and the residue was partitioned between DCM and aqueous sodium hydrogen carbonate, then extracted with DCM (×2). The combined organic extracts were washed with brine, dried (MgSO$_4$) and evaporated under reduced pressure. The residual solid was recrystallised from ethanol to give the subtitle compound as buff coloured crystals (1.1 g).

$^1$H NMR CDCl$_3$: δ 8.02-7.31 (8H, m).

(ii) {3-chloro-5-[2-chloro-4-(phenylsulfonyl)phenoxy]phenyl}acetic acid

The title compound was prepared by the method of example 2 step (iii) using the product of step (i) and the product of example 18 step (iv).

$^1$H NMR DMSO-d6: δ 8.19 (1H, d), 8.02 (2H, d), 7.91 (1H, dd), 7.76-7.63 (3H, m), 7.28 (1H, s), 7.18-7.13 (2H, m), 7.03 (1H, s), 3.56 (2H, s).

MS: APCI−ve 391 (M-CO$_2$).

EXAMPLE 30

{3-chloro-5-[4-(ethylsulfonyl)-2-fluorophenoxy]phenyl}acetic acid

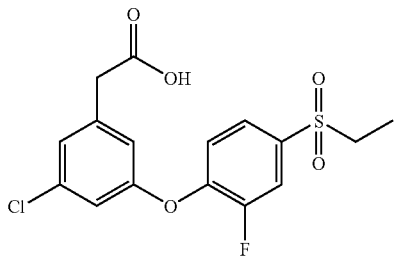

The title compound was prepared by the method of example 2 step (iii) using the product of example 10 step (ii) and the product of example 18 step (iv).

$^1$H NMR DMSO-d6: δ 7.77 (1H, dd), 7.67 (1H, dd), 7.21-7.12 (2H, m), 6.98 (1H, d), 6.89 (1H, s), 3.62 (2H, s), 3.15 (2H, q), 1.32 (3H, t).

MS: APCI−ve 327 (M-CO$_2$).

EXAMPLE 31

{3-chloro-5-[2-fluoro-4-(phenylsulfonyl)phenoxy]phenyl}acetic acid

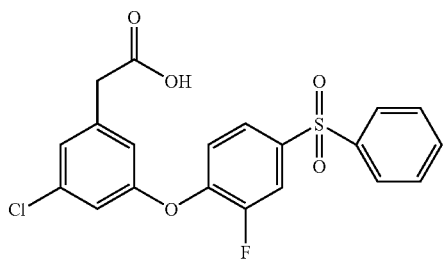

The title compound was prepared by the method of example 2 step (iii) using the product of example 24 step (i) and the product of example 18 step (iv).

$^1$H NMR DMSO-d6: δ 7.96-7.93 (2H, dd), 7.76-7.62 (2H, m), 7.61-7.48 (3H, m), 7.06-7.03 (2H, m), 6.88 (2H, d), 3.55 (2H, s).

MS: APCI−ve 419 (N—H).

EXAMPLE 32

[3-{2-fluoro-4-[(4-fluorobenzyl)sulfonyl]phenoxy}-5-(trifluoromethyl)phenyl]acetic acid

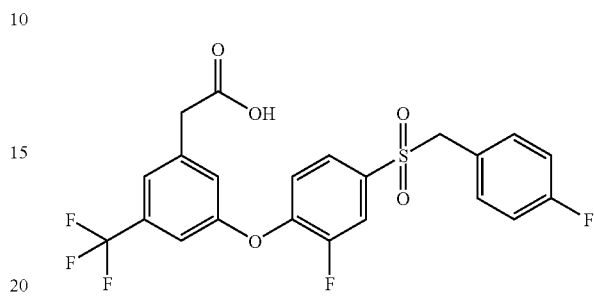

The title compound was prepared by the method of example 2 step (iii) using the product of example 25 step (iv) and the product of example 15 step (i).

$^1$H NMR DMSO-d6: δ 7.76-7.80 (1H, d) 7.48-7.53 (2H, m), 7.12-7.34 (7H, m), 4.76 (2H, s), 3.74 (2H, s).

MS: APCI−ve 441 (M-CO$_2$).

EXAMPLE 33

(3-chloro-5-{4-[(4-fluorobenzyl)sulfonyl]phenoxy}phenyl)acetic acid

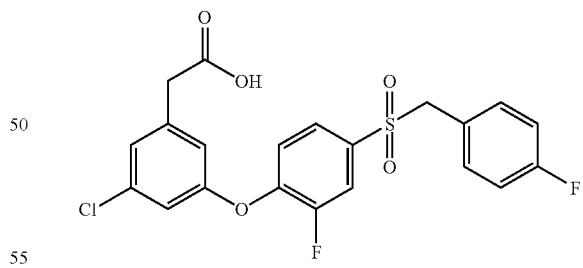

The title compound was prepared as described in example 2 step (iii) but instead using the product from example 18 step (iv) and the product from example 15 step (i).

$^1$H NMR DMSO-d6: δ 7.77-7.74 (1H, d), 7.53-7.47 (1H, d), 7.41-7.11 (8H, m), 4.76 (2H, s), 3.61 (2H, s).

MS: ESI−ve 407 (M-CO$_2$).

EXAMPLE 34

(3-chloro-5-{2-chloro-4-[(4-fluorobenzyl)sulfonyl]phenoxy}phenyl)acetic acid

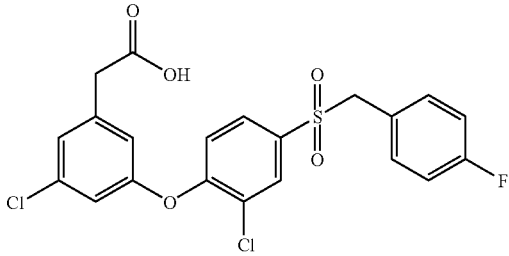

(i) 2-chloro-1-fluoro-4-[(4-fluorobenzyl)sulfonyl]benzene

A solution of 3-chloro-4-fluorobenzenethiol (1.0 g), 1-(bromomethyl)-4-fluorobenzene (1.15 g) and potassium carbonate (0.85 g) in DMF (10 ml) was stirred overnight at RT then diluted with water, extracted with ether, and the organics dried (MgSO$_4$) and evaporated under reduced pressure. The resulting oil was dissolved in DCM (10 ml) and MCPBA (1.2 g) added and stirred at RT overnight. The solution was then washed with aqueous sodium metabisulphite and aqueous sodium hydrogen carbonate, dried (MgSO$_4$) and evaporated under reduced pressure to give an oil which was purified by flash column chromatography (eluting 3:2 i-hexane/ether) to give the subtitle compound as a white solid (1.3 g).
$^1$H NMR CDCl$_3$: δ 7.74-7.71 (1H, d), 7.53-7.49 (1H, m), 7.28-7.20 (2H, m), 7.08-7.06 (1H, m), 6.92-6.86 (2H, m), 4.31 (2H, s).

(ii) (3-chloro-5-{2-chloro-4-[(4-fluorobenzyl)sulfonyl]phenoxy}phenyl)acetic acid The title compound was prepared as described in example 2 step (iii) but instead using the product from example 18 step (iv) and the product from step (i).
1H NMR DMSO-d6: δ 7.89-7.87 (1H, s), 7.64-7.59 (1H, d), 7.33-7.00 (8H, m), 4.76 (2H, s), 3.62 (2H, s).
MS: ESI-ve 423 (M-CO$_2$).

EXAMPLE 35

{3-chloro-5-[4-(methylsulfonyl)-2-(trifluoromethyl)phenoxy]phenyl}acetic acid

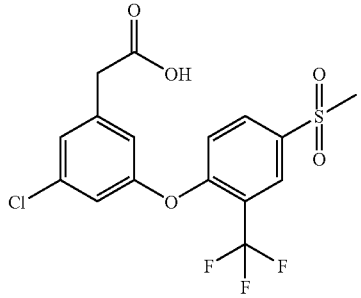

The title compound was prepared as described in example 2 step (iii) but instead using the product from example 18 step (iv) and the product from example 2 step (ii).
1H NMR DMSO-d6: δ 8.24-8.15 (2H, m), 7.27-7.16 (3H, m), 7.05 (1H, s), 3.46 (2H, s), 3.30 (3H, s).
MS: ESI-ve 363 (M-CO$_2$).

EXAMPLE 36

{3-chloro-5-[4-(ethylsulfonyl)-2-(trifluoromethyl)phenoxy]phenyl}acetic acid

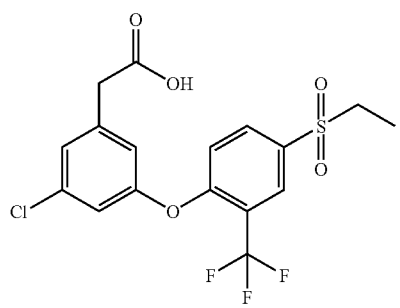

The title compound was prepared as described in example 2 step (iii) but instead using the product from example 18 step (iv) and the product from example 4 step (i).
1H NMR DMSO-d6: δ 8.24-8.15 (2H, m), 7.27-7.16 (3H, m), 7.05 (1H, s), 3.54 (2H, s), 3.46 (2H, q), 1.15-1.06 (3H, t).
MS: ESI-ve 377 (M-CO$_2$).

EXAMPLE 37

[3-[2-fluoro-4-(Phenylsulfonyl)phenoxy]-5-(trifluoromethyl)phenyl]acetic acid

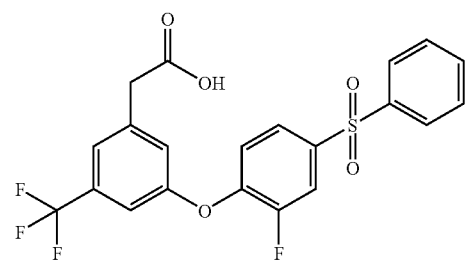

The title compound was prepared as described in example 2 step (iii) but instead using the product from example 25 step (iv) and the product from example 24 step (i).
1H NMR DMSO-d6: δ 8.11-8.01 (3H, m), 7.82-7.63 (4H, m), 7.54 (1H, s) 7.45 (1H, s) 7.32 (1H, s), 7.28-7.24 (1H, t), 3.74 (2H, s).
MS: ESI-ve 409 (M-CO$_2$).

EXAMPLE 38

[3-[2-chloro-4-(Phenylsulfonyl)phenoxy]-5-(trifluoromethyl)phenyl]acetic acid

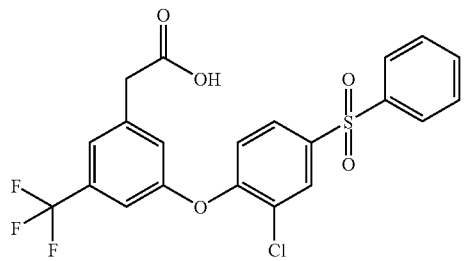

The title compound was prepared as described in example 2 step (iii) but instead using the product from example 25 step (iv) and the product from example 29 step (i).

1H NMR DMSO-d6: δ 8.17 (1H, s), 8.01-7.99 (2H, d), 7.91-7.88 (1H, d), 7.72-7.61 (3H, m) 7.50 (1H, s) 7.37-7.31 (2H, d), 7.12-7.09 (1H, d), 3.57 (2H, s).

MS: ESI−ve 425 (M-CO$_2$).

EXAMPLE 39

[3-[4-(ethylsulfonyl)-2-fluorophenoxy]-5-(trifluoromethyl)phenyl]acetic acid

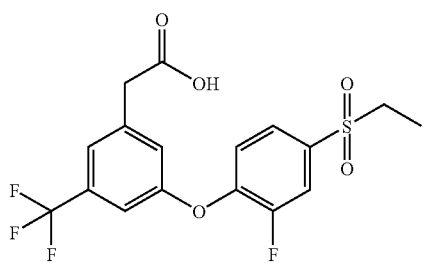

The title compound was prepared as described in example 2 step (iii) but instead using the product from example 25 step (iv) and the product from example 10 step (ii).

1H NMR DMSO-d6: δ 7.96-7.92 (1H, d), 7.73-7.71 (1H, d), 7.50 (1H, s), 7.37-7.30 (3H, m), 3.58 (2H, s), 3.38-3.33 (2H, q), 1.17-1.11 (3H, t).

MS: ESI−ve 361 (M-CO$_2$).

EXAMPLE 40

[3-[2-cyano-4-(ethylsulfonyl)phenoxy]-5-(trifluoromethyl)phenyl]acetic acid

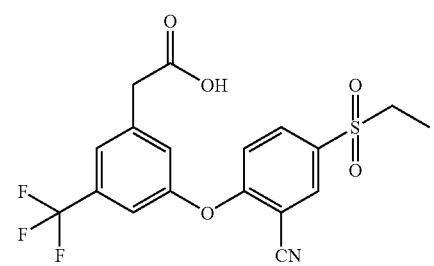

The title compound was prepared as described in example 2 step (iii) but instead using the product from example 25 step (iv) and the product from example 12 step (i).

1H NMR DMSO-d6: δ 8.46-8.45 (1H, m), 8.13-8.09 (1H, d), 7.65 (2H, bm), 7.54 (1H, s), 7.15-7.12 (1H, d), 3.69 (2H, s), 3.43-3.35 (2H, q), 1.16-1.11 (3H, t).

MS: ESI−ve 368 (M-CO$_2$).

EXAMPLE 41

[3-[4-(ethylsulfonyl)-2-(trifluoromethyl)phenoxy]-5-(trifluoromethyl)phenyl]acetic acid

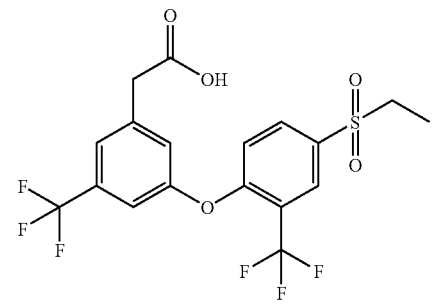

The title compound was prepared as described in example 2 step (iii) but instead using the product from example 25 step (iv) and the product from example 4 step (i).

1H NMR DMSO-d6: δ 8.21-8.14 (2H, m), 7.62 (1H, s), 7.52 (1H, s), 7.46 (1H, s), 7.26-7.24 (1H, d), 3.73 (2H, s), 3.46-3.39 (2H, q), 1.17-1.11 (3H, t).

MS: ESI−ve 411 (M-CO$_2$).

EXAMPLE 42

{3-[4-(benzylsulfonyl)-2-chlorophenoxy]-5-chlorophenyl}acetic acid

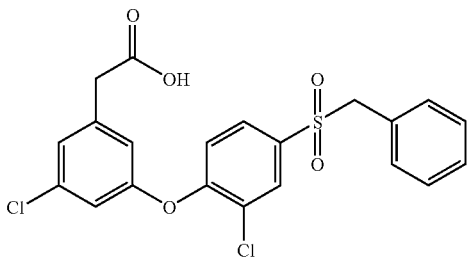

(i) 4-(benzylsulfonyl)-2-chloro-1-fluorobenzene

The subtitle compound was prepared by the method of example 34 step (i) using 3-chloro-4-fluorobenzenethiol (1.0 g) and benzyl bromide (0.73 ml) to give a white solid (1.2 g).
$^1$H NMR CDCl$_3$: δ 7.68-7.65 (1H, d), 7.49-7.09 (7H, m), 4.31 (2H, s).

(ii) {3-[4-(benzylsulfonyl)-2-chlorophenoxy]-5-chlorophenyl}acetic acid

The title compound was prepared as described in example 2 step (iii) but instead using the product from example 18 step (iv) and the product from step (i).
$^1$H NMR DMSO-d6: δ 7.88-7.87 (1H, s), 7.65-7.61 (1H, d), 7.35-7.19 (7H, m), 7.08-6.99 (2H, m), 4.76 (2H, s), 3.60 (2H, s).
MS: APCI−ve 449 (M−H).

EXAMPLE 43

{3-chloro-5-[4-(phenylsulfonyl)-2-(trifluoromethyl)phenoxy]phenyl}acetic acid

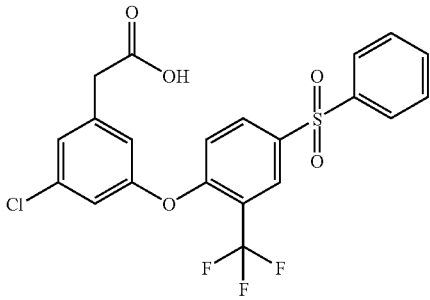

(i) 1-fluoro-4-(phenylsulfonyl)-2-(trifluoromethyl)benzene

4-Fluoro-3-(trifluoromethyl)aniline (5.0 g), diphenyldisulfide (6.0 g) and isoamylnitrite (8 ml) in acetonitrile (60 ml) were heated at 60° C. for 2 h, then cooled and evaporated under reduced pressure. The residue was purified by flash column chromatography (eluent isohexane) then dissolved in acetonitrile (60 ml) and water (10 ml) then oxone (20 g) added and the mixture stirred at RT for 72 h. The mixture was extracted between ether and water and the organics dried (MgSO$_4$) and evaporated under reduced pressure. The residue was purified by flash column chromatography (eluent: 5 to 10% ethyl acetate in isohexane) to give the subtitle compound (2.14 g).
1H NMR DMSO-d6: δ 8.24-8.13 (2H, m), 7.95 (2H, d), 7.66-7.53 (3H, m), 7.32 (1H, t).

(ii) {3-chloro-5-[4-(phenylsulfonyl)-2-(trifluoromethyl)phenoxy]phenyl}acetic acid The title compound was prepared as described in example 2 step (iii) but instead using the product from example 18 step (iv) and the product from step (i).
1H NMR DMSO-d6: δ 8.25-8.20 (2H, m), 8.06-8.03 (2H, d), 7.76-7.63 (3H, m), 7.38-7.10 (4H, m), 3.56 (2H, s).
MS: APCI−ve 469 (M−H).

EXAMPLE 44

{3-chloro-5-[2-cyano-4-(phenylsulfonyl)phenoxy]phenyl}acetic acid

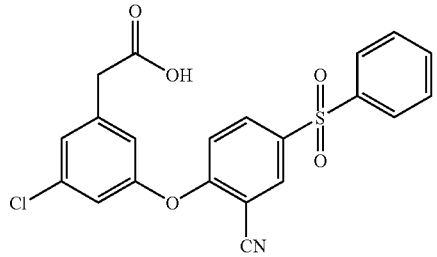

(i) 2-chloro-5-(phenylsulfonyl)benzonitrile

A solution of 5-amino-2-chlorobenzonitrile (6.6 g), diphenyldisulphide (11.0 g) and isoamylnitrile (10 ml) in acetonitrile (100 ml) was heated at 60° C. for 6 h then evaporated under reduced pressure. The residue was purified by flash column chromatography (eluent: iso-hexane to 1% EtOAc in iso-hexane) and the resulting solid dissolved in DCM. MCPBA (8.0 g) was added portionwise and the mixture stirred for 2 h, filtered and the filtrate washed with aqueous sodium metabisulphite, aqueous sodium hydrogen carbonate then water and the organics dried (MgSO$_4$) and evaporated under reduced pressure to give the subtitle compound (2.9 g).
$^1$H NMR CDCl$_3$: δ 8.22 (1H, s), 8.08 (1H, d), 7.95 (2H, d), 7.68-7.54 (4H, m).

(ii) {3-chloro-5-[2-cyano-4-(phenylsulfonyl)phenoxy]phenyl}acetic acid

The title compound was prepared as described in example 2 step (iii) but instead using the product from example 18 step (iv) and the product from step (i).
1H NMR DMSO-d6: δ 8.59 (1H, s), 8.19-8.15 (1H, d), 8.04-8.01 (2H, d), 7.76-7.63 (3H, m), 7.30-7.29 (2H, m), 7.13 (1H, s), 7.06-7.03 (1H, d), 3.41 (2H, s).
MS: APCI−ve 426 (M−H).

EXAMPLE 45

{3-[4-(benzylsulfonyl)-2-fluorophenoxy]-5-chlorophenyl}acetic acid

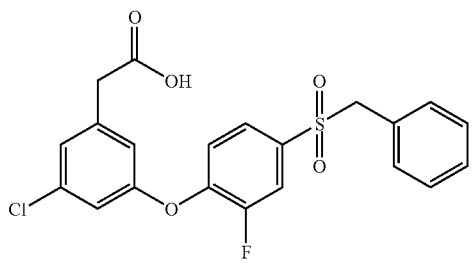

(i) 4-(benzylsulfonyl)-1,2-difluorobenzene

The subtitle compound was prepared by the method of example 34 step (i) using 3,4-difluorobenzenethiol (1.3 g) and benzyl bromide (1.5 ml) to give a white solid (2.4 g).
¹H NMR CDCl₃: δ 7.48-7.20 (8H, m), 4.33 (2H, s).

(ii) {3-[4-(benzylsulfonyl)-2-fluorophenoxy]-5-chlorophenyl}acetic acid

The title compound was prepared as described in example 2 step (iii) but instead using the product from example 18 and the product from step (i).
1H NMR DMSO-d6: δ 7.77-7.73 (1H, d), 7.66-7.51 (1H, d), 7.35-7.18 (7H, m), 7.05-6.99 (2H, m), 4.75 (2H, s), 3.61 (2H, s).
MS: APCI−ve 433 (M−H).

EXAMPLE 46

(3-chloro-5-{2-fluoro-4-[(3-fluorobenzyl)sulfonyl]phenoxy}phenyl)acetic acid

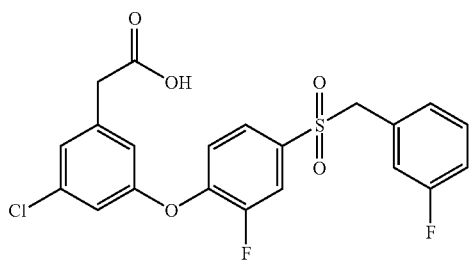

(i) 1,2-difluoro-4-[(3-fluorophenyl)sulfonyl]benzene

The subtitle compound was prepared by the method of example 34 step (i) using 3,4-difluorobenzenethiol (1.0 g), and 1-(bromomethyl)-3-fluorobenzene (1.28 g) to give a white solid (1.4 g).
¹H NMR CDCl₃: δ 7.53-7.39 (2H, m), 7.32-7.22 (2H, m), 7.09-7.03 (1H, m), 6.90-6.86 (2H, m), 4.30 (2H, s).

(ii) (3-chloro-5-{2-fluoro-4-[(3-fluorobenzyl)sulfonyl]phenoxy}phenyl)acetic acid The title compound was prepared as described in example 2 step (iii) but instead using the product from example 18 step (iv) and the product from step (i).
1H NMR DMSO-d6: δ 7.78-7.74 (1H, d), 7.52-7.49 (1H, d), 7.41-7.15 (4H, m), 7.06-6.96 (4H, m), 4.79 (2H, s), 3.48 (2H, s).
MS: APCI−ve 407 (M-CO₂).

EXAMPLE 47

{3-[4-(benzylsulfonyl)-2-(trifluoromethyl)phenoxy]-5-chlorophenyl}acetic acid

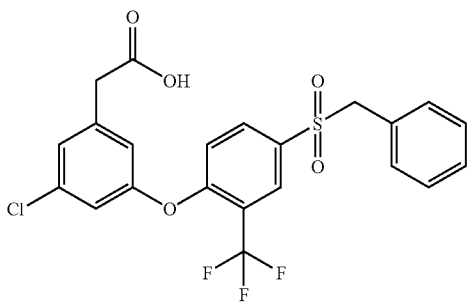

(i) 4-(benzylsulfonyl)-1-fluoro-2-(trifluoromethyl)benzene

The subtitle compound was prepared by the method of example 44 step (i) using 3-trifluoromethyl-4-fluoroaniline (2.0 g) and dibenzyldisulfide to give a white solid (0.42 g).
¹H NMR CDCl₃: δ 7.80-7.77 (2H, m), 7.39-7.25 (4H, m), 7.10-7.07 (2H, d), 4.34 (2H, s).

(ii) {3-[4-(benzylsulfonyl)-2-(trifluoromethyl)phenoxy]-5-chlorophenyl}acetic acid The title compound was prepared as described in example 2 step (iii) but instead using the product from example 18 step (iv) and the product from step (i).
1H NMR DMSO-d6: δ 7.94-7.86 (2H, d), 7.33-7.28 (4H, m), 7.20-7.16 (4H, m), 7.05 (1H, s), 4.76 (2H, s), 3.54 (2H, s).
MS: APCI−ve 439 (M-CO₂).

EXAMPLE 48

(3-chloro-5-{2-fluoro-4-[(2-fluorobenzyl)sulfonyl]phenoxy}phenyl)acetic acid

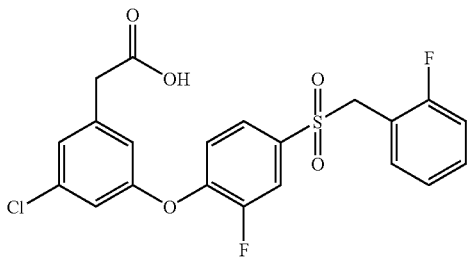

(i) 1,2-difluoro-4-[(2-fluorobenzyl)sulfonyl]benzene

The subtitle compound was prepared by the method of example 34 step (i) using 3,4-difluorobenzenethiol (1.0 g), and 1-(bromomethyl)-2-fluorobenzene (1.28 g) to give a white solid (2.3 g).

1H NMR CDCl$_3$: δ 7.62-7.14 (6H, m), 6.97-6.90 (1H, t), 4.41 (2H, s).

(ii) (3-chloro-5-{2-fluoro-4-[(2-fluorobenzyl)sulfonyl]phenoxy}phenyl)acetic acid The title compound was prepared as described in example 2 step (iii) but instead using the product from example 18 step (iv) and the product from step (i).

1H NMR DMSO-d6: δ 7.81-7.75 (1H, d), 7.57-7.39 (2H, d), 7.33-7.16 (5H, m), 7.06-6.97 (2H, m), 4.78 (2H, s), 3.49 (2H, s).

MS: APCI−ve 407 (M-CO$_2$).

EXAMPLE 49

(3-chloro-5-{4-[(4-chlorobenzyl)sulfonyl]-2-fluorophenoxy}phenyl)acetic acid

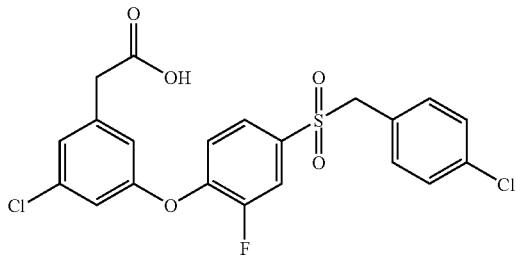

(i) 4-[(4-chlorobenzyl)sulfonyl]-1,2-difluorobenzene

Ferric chloride (1.27 g), was added to a stirred mixture of 3,4-difluorosulfonyl chloride (5 g) and chlorobenzene (4.65 ml). The reaction mixture was heated to reflux for 16 h then allowed to cool to room temperature. The reaction mixture was diluted with water, extracted with ethyl acetate (×2). The combined organic extracts were washed with brine, dried (MgSO$_4$) and evaporated under reduced pressure. The residual solid was recrystallised from ethanol to give the subtitle compound as buff coloured crystals (4.35 g).

1H NMR CDCl$_3$: δ 7.53-7.48 (2H, m), 7.30-7.22 (3H, m), 7.07-7.04 (2H, d), 4.28 (2H, s).

(ii) (3-chloro-5-{4-[(4-chlorobenzyl)sulfonyl]-2-fluorophenoxy}phenyl)acetic acid The title compound was prepared as described in example 2 step (iii) but instead using the product from example 18 step (iv) and the product from step (i).

1H NMR DMSO-d6: δ 12.49 (1H, s), 7.80-7.77 (1H, d), 7.51-7.19 (7H, m), 7.11 (1H, s), 7.02 (1H, s), 4.77 (2H, s), 3.64 (2H, s).

MS: APCI−ve 409 (M-CO$_2$).

EXAMPLE 50

2-[3-[4-(ethylsulfonyl)-2-(trifluoromethyl)phenoxy]-5-(trifluoromethyl)phenyl]propanoic acid

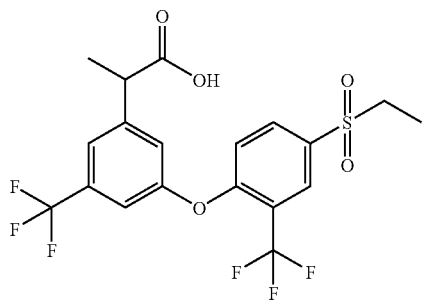

(i) methyl[3-methoxy-5-(trifluoromethyl)phenyl]acetate

The product from example 25 step (iv) (1.0 g) was dissolved in dry DMF (10 ml) and treated with iodomethane (0.6 ml) and potassium carbonate (1.25 g). The mixture was stirred at room temperature overnight. The mixture was diluted with water, extracted with ether, dried (MgSO$_4$) and evaporated under reduced pressure to give an oil. The oil was purified by flash column chromatography (eluent 2:1 diethylether/isohexane) (1.30 g).

1H NMR DMSO-d6 δ 7.13 (1H, s), 7.04-7.01 (2H, d), 3.85 (3H, s), 3.70 (3H, s), 3.65 (2H, s).

(ii) methyl 2-[3-methoxy-5-(trifluoromethyl)phenyl]propanoate

The product from step (i) (1.3 g) was added to a pre-formed solution of butyllithium (2.5M in hexanes, 2.51 ml), diisopropylamine (0.88 ml) in dry THF (30 ml) at −78° C. The mixture was kept at −78° C. for 1 hour before adding iodomethane (0.4 ml). The mixture was slowly allowed to warm to room temperature overnight. The mixture was diluted with 2M HCl, extracted with ether, dried (MgSO$_4$) and evaporated under reduced pressure to give an oil. The oil was purified by flash column chromatography (eluent 2:1 isohexane/diethylether) (0.8 g).

1H NMR DMSO-d6: δ 7.17-7.13 (1H, s), 7.02 (2H, s), 3.84 (3H, s), 3.74 (1H, q), 3.68 (3H, s), 1.52-1.50 (3H, d).

(iii) 2-[3-hydroxy-5-(trifluoromethyl)phenyl]propanoic acid

The product from step (ii) (0.8 g) was dissolved in glacial acetic acid (20 ml) and treated with 48% aqueous HBr (20 ml). The mixture was heated at 100° C. for 16 h. The mixture was cooled and diluted with 2M NaOH, extracted with ethyl acetate, dried (MgSO$_4$) and evaporated under reduced pressure to give an oil, which was purified by RPHPLC to give a colourless oil (0.5 g).

MS: APCI−ve 233 (M−H).

(iv) 2-[3-[4-(ethylsulfonyl)-2-(trifluoromethyl)phenoxy]-5-(trifluoromethyl)phenyl]propanoic acid The title compound was prepared as described in example 2 step (iii) but instead using the product from step (iii) and the product from example 4 step (i).

1H NMR DMSO-d6: δ 8.20-8.19 (1H, s), 8.14-8.11 (1H, d), 7.60 (1H, s), 7.50-7.47 (2H, d), 7.26-7.21 (1H, d), 3.85-3.80 (1H, q), 3.43-3.38 (2H, q), 1.39-1.38 (3H, d), 1.15-1.11 (3H, t).

MS: ESI–ve 425 (M-$CO_2$).

EXAMPLE 51

2-[3-[2-chloro-4-(ethylsulfonyl)phenoxy]-5-(trifluoromethyl)phenyl]propanoic acid

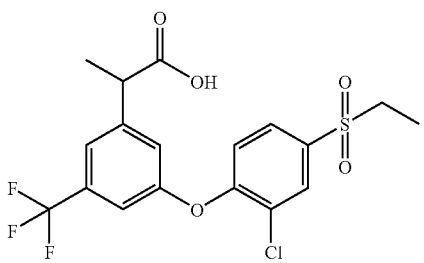

The title compound was prepared as described in example 2 step (iii) but instead using the product from example 50 step (iii) and the product from example 3 step (i).

1H NMR DMSO-d6: δ 8.10-8.09 (1H, s), 7.84-7.82 (1H, d), 7.54 (1H, s), 7.39-7.38 (2H, d), 7.22-7.20 (1H, d), 3.80-3.74 (1H,), 3.40-3.35 (2H, q), 1.37-1.35 (3H, d), 1.14-1.11 (3H, t).

MS: ESI–ve 391 (M-$CO_2$).

EXAMPLE 52

2-[3-[2-chloro-4-(phenylsulfonyl)phenoxy]-5-(trifluoromethyl)phenyl]propanoic acid

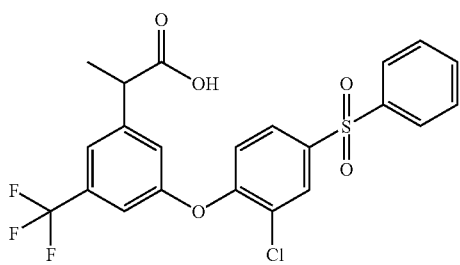

The title compound was prepared as described in example 2 step (iii) but instead using the product from example 50 step (iii) and the product from example 29 step (i).

1H NMR DMSO-d6: δ 8.19 (1H, s), 8.02-8.00 (2H, d), 7.91-7.88 (1H, d), 7.73-7.62 (3H, m), 7.53 (1H, s), 7.39-7.37 (2H, d), 7.12-7.09 (1H, d), 3.73-3.71 (1H, q), 1.34-1.32 (3H, d).

MS: ESI(–ve) 439 (M-$CO_2$).

EXAMPLE 53

2-[3-{2-chloro-4-[(4-fluorobenzyl)sulfonyl]phenoxy}-5-(trifluoromethyl)phenyl]propanoic acid

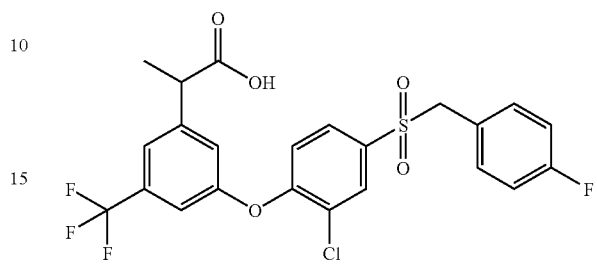

The title compound was prepared as described in example 2 step (iii) but instead using the product from example 50 step (iii) and the product from example 34 step (i).

1H NMR DMSO-d6: δ 7.92-7.91 (1H, s), 7.60-7.53 (2H, m), 7.34 (2H, s), 7.25-7.14 (5H, m), 4.77 (2H, s), 3.90-3.84 (1H, q), 1.40-1.39 (3H, d).

MS: ESI–ve 471 (M-$CO_2$).

EXAMPLE 54

(3-chloro-5-{4-[(4-chlorobenzyl)sulfonyl]-2-fluorophenoxy}phenyl)acetic acid

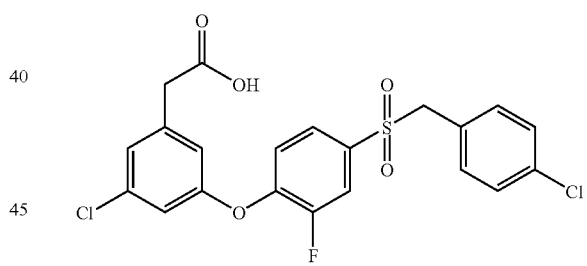

(i) 4-[(4-chlorobenzyl)sulfonyl]-1,2-difluorobenzene

A solution of 3,4-difluorobenzenethiol (1.0 g), 1-(bromomethyl)-4-chlorobenzene (1.28 g) and potassium carbonate (0.94 g) in DMF (10 ml) was stirred overnight at RT then diluted with water, extracted with ether, and the organics dried (MgSO$_4$) and evaporated under reduced pressure. The resulting oil was dissolved in DCM (10 ml) and MCPBA (2.94 g) added and stirred at RT overnight. The solution was then washed with aqueous sodium metabisulphite and aqueous sodium hydrogen carbonate, dried (MgSO$_4$) and evaporated under reduced pressure to give a solid, triturated with isohexane to give the subtitle compound as a white solid (2.3 g).

1H NMR CDCl3: δ 7.53-7.48 (2H, m), 7.30-7.22 (3H, m), 7.07-7.04 (2H, d), 4.28 (2H, s).

(ii) (3-chloro-5-{4-[(4-chlorobenzyl)sulfonyl]-2-fluorophenoxy}phenyl)acetic acid The title compound was prepared as described in example 2 step (iii) but instead using the product from example 18 step (iv) and the product from step (i).
1H NMR DMSO-d6: δ 12.49 (1H, s), 7.80-7.77 (1H, d), 7.51-7.19 (7H, m), 7.11 (1H, s), 7.02 (1H, s), 4.77 (2H, s), 3.64 (2H, s).
MS: APCI−ve: 423 (M−$CO_2$).

EXAMPLE 55

{3-bromo-5-[2-chloro-4-(ethylsulfonyl)phenoxy]phenyl}acetic acid

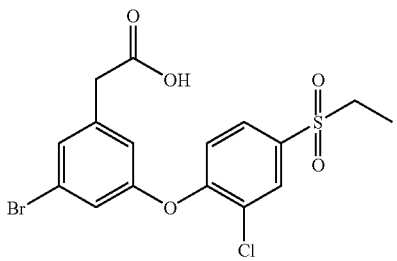

(i) 3-bromo-5-methoxybenzonitrile

Sodium methoxide (2.02 g) was added to a stirred solution of 3-fluoro-5-bromobenzonitrile (5.0 g) in DMPU (20 ml) and stirred at RT for 2 h. The reaction was diluted with water and the resulting solid formed was filtered and washed with water, then dried in vacuo to give the subtitle compound (5.10 g).
1H NMR DMSO-d6: δ7.39-7.38 (1H, s), 7.30-7.26 (1H, m), 7.11 (1H, s), 3.83 (3H, s).

(ii) 3-bromo-5-methoxybenzoic acid

The product from step (i) (5.10 g) was dissolved in methanol (20 ml) and 6N NaOH (20 ml) and heated to reflux for 6 h. The mixture was diluted with 2M HCl, extracted with ethyl acetate, dried ($MgSO_4$) and evaporated under reduced pressure to give a white solid (5.10 g).
MS: APCI−ve 229 (M−H).

(iii) (3-bromo-5-methoxyphenyl)methanol

Lithium aluminium hydride (1M in THF, 22.07 ml) was added dropwise to a stirred solution of the product of step (ii) (5.1 g) in THF (50 ml) at 0° C. and stirred at RT overnight. The reaction was quenched in 2M HCl, extracted with ether, dried ($MgSO_4$) and evaporated under reduced pressure to give an oil, which was purified by flash column chromatography (eluent 1:1 isohexane/diethylether) to give the subtitle compound (5.38 g).
1H NMR CDCl3: δ 7.08 (1H, s), 6.96-6.91 (1H, s), 6.83-6.81 (1H, s), 4.62 (2H, s), 3.79 (3H, s).

(iv) (3-bromo-5-methoxyphenyl)acetonitrile

The product from step (iii) (5.38 g) was dissolved in dry DCM (50 ml) and dry DMF (2.3 ml) added followed by thionyl chloride (2.17 ml). The reaction mixture was stirred at RT overnight, and then diluted with aqueous sodium hydrogen carbonate, extracted with DCM, dried ($MgSO_4$) and evaporated under reduced pressure to give an oil. The oil was dissolved in DMF (20 ml), sodium cyanide (1.30 g) was added and stirred at RT overnight. The reaction mixture was diluted with water, extracted with ether, dried ($MgSO_4$) and evaporated under reduced pressure. The residue was purified by flash column chromatography (eluent 1:2 ether/isohexane) to give the subtitle compound (4.50 g).
1H NMR CDCl3: δ7.07-7.02 (2H, m), 6.81 (1H, s), 3.83 (3H, s), 3.70 (2H, s).

(v) (3-bromo-5-hydroxyphenyl)acetic acid

The product of step (iv) (4.5 g), in glacial acetic acid (30 ml) was treated with 48% aqueous HBr (30 ml) and heated at 100° C. for 24 h. The reaction mixture was partitioned between water and ethyl acetate, the organics were separated then dried ($MgSO_4$) and evaporated under reduced pressure to give a tan solid which was triturated with ether/isohexane (4.24 g).
MS: APCI−ve 229/231 (M−H).

(vi) {3-bromo-5-[2-chloro-4-(ethylsulfonyl)phenoxy]phenyl}acetic acid

The title compound was prepared as described in example 2 step (iii) but instead using the product from step (v) and the product from example 3 step (i).
1H NMR DMSO-d6: 8.08-8.07 (1H, s), 7.84-7.81 (1H, d), 7.38-7.20 (3H, m), 7.07 (1H, s), 3.59 (2H, s), 3.39-3.34 (2H, q), 1.14-1.07 (3H, t).
MS: APCI−ve 431/433 (M−H).

EXAMPLE 56

{3-[2-chloro-4-(ethylsulfonyl)phenoxy]-5-methylphenyl}acetic acid

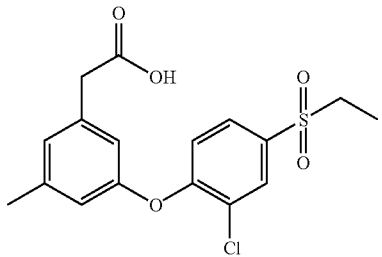

(i) methyl 3-bromo-5-hydroxybenzoate

The product from example 55 step (v) (3.24 g) was added to a preformed solution of methanol (200 ml) and acetyl chloride (20 ml) and stirred at RT overnight. The mixture was evaporated under reduced pressure to give an oil. The oil was purified by flash column chromatography (eluent 1:1 ether/isohexane) to give the subtitle compound (3.16 g).
1H NMR CDCl3: δ6.98-6.97 (1H, s), 6.92-6.91 (1H, s), 6.70-6.69 (1H, m), 5.71 (1H, bs), 3.71-3.70 (3H, s), 3.50 (2H, s).

(ii) methyl 3-bromo-5-[2-chloro-4-(ethylsulfonyl)phenoxy]benzoate

The subtitle compound was prepared as described in example 2 step (iii) but instead using the product from step (i) and the product from example 3 step (i).
MS: APCI−ve 446 (M−H).

(iii) {3-[2-chloro-4-(ethylsulfonyl)phenoxy]-5-methylphenyl}acetic acid

The title compound was prepared by treating the product from step (ii) (0.6 g) in dry THF (10 ml) with bisdiphenylphosphinoferrocene palladium (0.1 g) and 2.0M methyl zinc chloride (2.01 ml). The mixture was heated to reflux for 2 h, partitioned between water and ethyl acetate, the organics separated then dried (MgSO$_4$) and evaporated under reduced pressure to an oil. The oil was purified by flash column chromatography (eluent ether) then dissolved in methanol (10 ml) and 2M NaOH (10 ml) added and stirred at RT overnight. The mixture was diluted with water, extracted with ether (which was discarded) and the aqueous layer acidified with 2M HCl, extracted with ethyl acetate, and the ethyl acetate layer dried (MgSO$_4$) and evaporated under reduced pressure to an oil. The oil was purified by RPHPLC to give the title compound.
1H NMR DMSO-d6: δ 8.04 (1H, s), 7.80-7.78 (1H, d), 7.08-6.77 (4H, m), 3.43 (2H, s), 3.37-3.31 (2H, q), 2.29 (3H, s), 1.13-1.10 (3H, t).
MS: APCI−ve 367 (M−H).

EXAMPLE 57 methyl 3-[2-chloo-4-(ethylsulfonyl)phenoxy]-5-cyanobenzoate

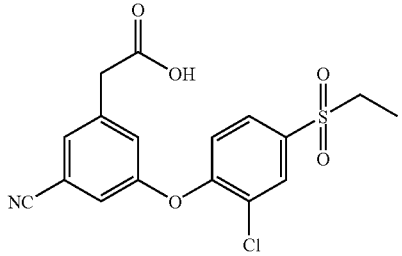

The title compound was prepared using the method described in example 56 step (iii) but instead using the product from example 56 step (ii) and zinc cyanide.
1H NMR DMSO-d6: 8.05 (1H, s), 7.84-7.82 (1H, d), 7.64-7.07 (3H, s), 6.99-6.97 (1H, d), 3.49 (2H, s), 3.38-3.34 (2H, q), 1.15-1.11 (3H, t).
MS: APCI−ve 334 (M−H).

EXAMPLE 58

[3-{[2-chloro-4-(ethylsulfonyl)phenyl]thio}-5-(trifluoromethyl)phenyl]acetic acid

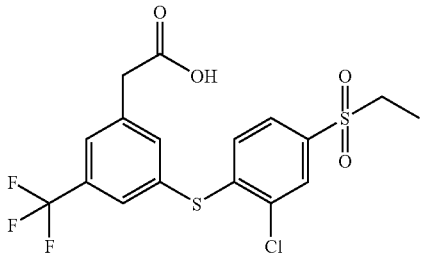

(i) [3-{[(dimethylamino)carbonothioyl]oxy}-5-(trifluoromethyl)phenyl]acetic acid The product from example 25 step (iv) (0.5 g), dimethylthiocarbamoyl chloride (0.32 ml), DMAP (0.026 g) and triethylamine (0.60 ml) in dry dioxane (10 ml) were stirred at 100° C. for 15 h. The mixture was diluted with water, extracted with ethyl acetate, dried (MgSO$_4$) and evaporated under reduced pressure to an oil. The oil was purified by flash column chromatography (eluent ether) to give the subtitle compound (0.52 g).
1H NMR CDCl3: δ 7.42 (1H, s), 7.26-7.23 (2H, m), 3.72 (5H, m), 3.44 (3H, s), 3.35 (3H, s).

(ii) [3-{[(dimethylamino)carbonyl]thio}-5-(trifluoromethyl)phenyl]acetic acid

The product from step (i) (0.51 g) in diphenylether (5 ml) was heated at 200° C. for 20 h. The reaction mixture was purified by flash column chromatography (eluent: DCM to diethylether) to give the subtitle compound (0.49 g).
MS: APCI(+ve): 322 (M+H).

(iii) [3-mercapto-5-(trifluoromethyl)phenyl]acetic acid

The product from step (ii) (0.49 g) was dissolved in methanol (10 ml) and 2M NaOH (10 ml) and stirred at RT overnight. The mixture was diluted with 2M HCl, extracted with ethyl acetate, dried (MgSO$_4$) and evaporated under reduced pressure to an solid (0.30 g)
1H NMR CDCl3-: δ 7.45 (1H, s), 7.32 (1H, s), 7.27-7.26 (1H, s), 3.76-3.66 (2H, s), 2.91 (1H, s).

(iv) [3-{[2-chloro-4-(ethylsulfonyl)phenyl]thio}-5-(trifluoromethyl)phenyl]acetic acid The title compound was prepared as described in example 2 step (iii) but instead using the product from step (iii) and the product from example 3 step (i).
1H NMR DMSO-d6: δ 7.97 (1H, s), 7.81-7.79 (3H, d), 7.73-7.69 (1H, d), 7.01-6.94 (1H, d), 3.63 (2H, s), 3.41-3.30 (2H, q), 1.19-1.06 (3H, t).
MS: APCI−ve 393 (M−CO$_2$).

EXAMPLE 59

{3-[2-chloro-4-(ethylsulfonyl)phenoxy]-5-methoxyphenyl}acetic acid

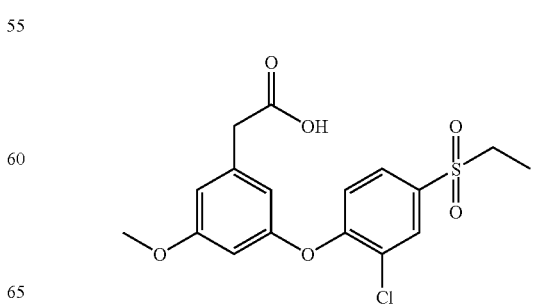

(i) methyl{3-[2-chloro-4-(ethylsulfonyl)phenoxy]-5-hydroxyphenyl}acetate

The subtitle compound was prepared as described in example 2 step (iii) but instead using the product from example 3 step (i) and methyl(3,5-dihydroxyphenyl)acetate.
MS: APCI–ve 383 (M–H).

(ii) {3-[2-chloro-4-(ethylsulfonyl)phenoxy]-5-methoxyphenyl}acetic acid

The product from step (i) was taken up in toluene (3 ml) and methanol (1 ml) and TMS-diazomethane (0.6 ml, 2M in diethylether) added, the mixture stirred at RT for 3 h then evaporated under reduced pressure. The residue was taken up in THF (2 ml) and methanol (1 ml) then 3M NaOH (2 ml) added and the mixture stirred at RT for 2 h. The mixture was then acidified to pH 2 and extracted with ethyl acetate. The organics were dried (MgSO$_4$), evaporated under reduced pressure and then passed onto a Varian NH$_2$ resin (eluting with ethyl acetate, acetonitrile, methanol, DCM then 20% acetic acid in DCM). The acidic fraction was evaporated under reduced pressure and then purified by RPHPLC to give a white solid.
1H NMR DMSO-d6: δ 8.07 (1H, d), 7.82 (1H, dd), 7.13 (1H, d), 6.78 (1H, s), 6.66 (1H, t), 6.63 (1H, s), 3.77 (3H, s), 3.54 (2H, s), 3.37 (3H, q), 1.14 (3H, t).
MS: APCI–ve 383 (M–H).

EXAMPLE 60

[3-{2-chloro-4-[(2-fluorobenzyl)sulfonyl]phenoxy}-5-(trifluoromethyl)phenyl]acetic acid

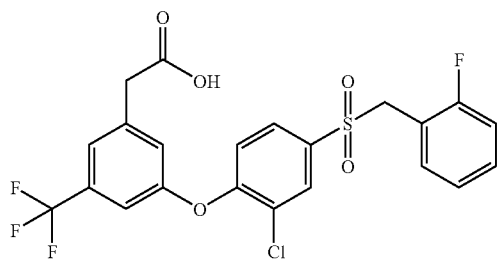

(i) 2-chloro-1-fluoro-4-[(2-fluorobenzyl)sulfonyl]benzene

The subtitle compound was prepared as described in example 54 step (i) but instead using the 3-chloro-4-fluorobenzenethiol and 1-(bromomethyl)-2-fluorobenzene.
1H NMR CDCl3: δ 7.71-7.68 (1H, m), 7.57-7.51 (1H, m), 7.39-7.32 (2H, m), 7.27-7.15 (2H, m), 6.98-6.92 (1H, m), 4.41 (2H, s).

(ii) [3-{2-chloro-4-[(2-fluorobenzyl)sulfonyl]phenoxy}-5-(trifluoromethyl)phenyl]acetic acid The title compound was prepared as described in example 2 step (iii) but instead using the product from example 25 step (iv) and the product from step (i).
1H NMR DMSO-d6: δ 8.02-7.94 (1H, m), 7.82-7.55 (2H, m), 7.45-7.12 (7H, m), 4.82-4.79 (2H, s), 3.76 (2H, s).
MS: APCI–ve 457 (M-CO$_2$).

EXAMPLE 61

[3-{[3-methyl-5-(phenylsulfonyl)pyridin-2-yl]oxy}-(trifluoromethyl)phenyl]acetic acid

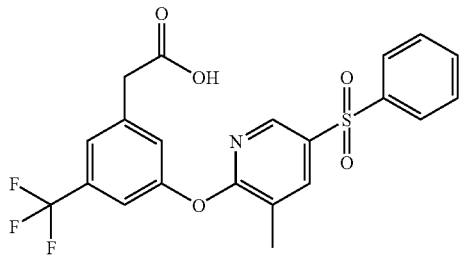

(i) 2-chloro-3-methyl-5-(phenylthio)pyridine

2-Chloro-3-methyl-5-bromopyridine (1.0 g) was added to a stirred solution of butyllithium (2.5M in hexanes, 1.94 ml) in dry THF (20 ml) at –78° C. The mixture was left at –78° C. for 5 minutes before treating with diphenyldisulphide (1.06 g). The mixture was allowed to warm to RT. After 1 h, the mixture was quenched with 2M HCl, extracted with ether (discarded) then the aqueous layer basified with saturated sodium hydrogen carbonate solution, extracted with ethyl acetate, dried (MgSO$_4$) and evaporated under reduced pressure to give a brown oil. The oil was subjected to flash column chromatography (eluent 3:2 DCM/ethyl acetate) to give the subtitle compound (2.30 g).
MS: APCI(–ve): 236 (M+H).

(ii) 2-chloro-3-methyl-5-(phenylsulfonyl)pyridine

The product from step (i) (2.30 g) was dissolved in DCM (10 ml) and TFA (5 ml). The mixture was evaporated under reduced pressure to give a yellow oil. The oil was dissolved in DCM (50 ml) and mCPBA (4.20 g) added and stirred at RT overnight. The solution was then washed with aqueous sodium metabisulphite and aqueous sodium hydrogen carbonate, dried (MgSO$_4$) and evaporated under reduced pressure to give an oil, which was purified by flash column chromatography (eluent 1:1 isohexane/diethylether) to give the subtitle compound (0.89 g).
1H NMR CDCl3: δ 8.75-8.74 (1H, s), 8.02-7.89 (2H, m), 7.69-7.49 (3H, m), 7.26 (1H, s), 2.31 (3H, s).

(iii) [3-{[3-methyl-5-(phenylsulfonyl)pyridin-2-yl]oxy}-5-(trifluoromethyl)phenyl]acetic acid The title compound was prepared as described in example 2 step (iii) but instead using the product from example 25 step (iv) and the product from step (ii).
1H NMR DMSO-d6: δ 8.54-8.53 (1H, s), 8.28 (1H, s), 8.01-7.98 (2H, m), 7.73-7.42 (6H, m), 3.74 (2H, s), 2.27 (3H, s).
MS: APCI–ve 450 (M–H).

EXAMPLE 62

[3-[2-chloro-4-(morpholin-4-ylsulfonyl)phenoxy]-5-(trifluoromethyl)phenyl]acetic acid

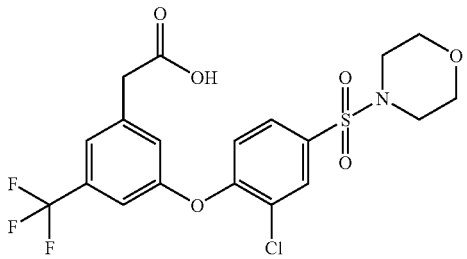

(i) 4-[(3-chloro-4-fluorophenyl)sulfonyl]morpholine 4-fluoro-3-chlorobenzenesulphonyl chloride (0.9 g) was stirred in dry DCM (10 ml) and morpholine (0.69 ml) added. The mixture was allowed to stir at RT for 1 h and then quenched with water, extracted with DCM, dried ($MgSO_4$) and evaporated under reduced pressure to give a white solid (1.10 g).

1H NMR CDCl3: δ 7.86-7.83 (1H, m), 7.69-7.64 (1H, m), 7.36-7.26 (1H, t), 3.78-3.75 (4H, m), 3.01 (4H, m).

(ii) [3-[2-chloro-4-(morpholin-4-ylsulfonyl)phenoxy]-5-(trifluoromethyl)phenyl]acetic acid The title compound was prepared as described in example 2 step (iii) but instead using the product from example 25 step (iv) and the product from step (i).

1H NMR DMSO-d6: δ 12.52 (1H, bs), 7.95-7.93 (1H, m), 7.73-7.33 (4H, m), 7.24-7.21 (1H, d), 3.76 (2H, s), 3.64 (4H, m), 2.93 (4H, m).

MS: APCI-ve 434 (M-$CO_2$).

EXAMPLE 63

[3-(4-benzoyl-2-chlorophenoxy)-5-(trifluoromethyl)phenyl]acetic acid

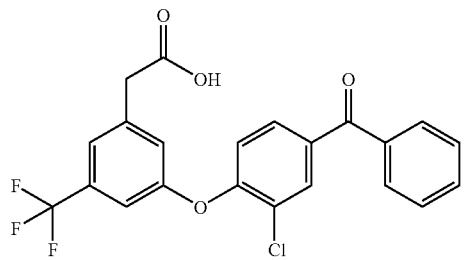

(i) (3-chloro-4-fluorophenyl)(phenyl)methanone 3-chloro-4-fluorobenzoyl chloride (1.0 g), benzene (2 ml) and ferric chloride (0.28 g) were heated to reflux for 16 h then diluted with water, extracted with ethyl acetate and the organics dried ($MgSO_4$) and evaporated under reduced pressure to give the subtitle compound as a brown solid (0.8 g).

1H NMR $CDCl_3$: δ 7.91-7.88 (1H, d), 7.77-7.48 (6H, m), 7.28-7.22 (1H, t).

(ii) [3-(4-benzoyl-2-chlorophenoxy)-5-(trifluoromethyl)phenyl]acetic acid

The title compound was prepared as described in example 2 step (iii) but instead using the product from example 25 step (iv) and the product from step (i).

1H NMR DMSO-d6: 7.95-7.93 (1H, m), 7.78-7.49 (7H, m), 7.25 (2H, s), 7.20-7.18 (1H, d), 3.60 (2H, s).

MS: APCI-ve 389 (N—$CO_2$).

EXAMPLE 64

[3-{2-chloro-4-[(3-fluorobenzyl)sulfonyl]phenoxy}-5-(trifluoromethyl)phenyl]acetic acid

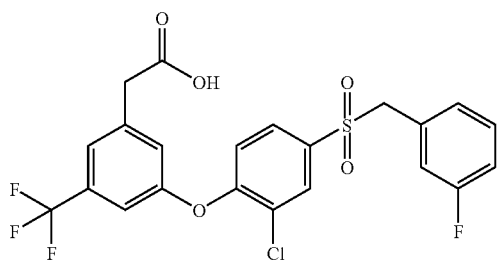

(i) 2-chloro-1-fluoro-4-[(3-fluorobenzyl)sulfonyl]benzene

The subtitle compound was prepared as described in example 54 step (i) but instead using 3-chloro-4-fluorobenzenethiol and 1-(bromomethyl)-3-fluorobenzene.

1H NMR CDCl3: δ 7.71-7.68 (1H, m), 7.57-7.51 (1H, m), 7.39-7.32 (2H, m), 7.27-7.15 (2H, m), 6.98-6.92 (1H, m), 4.41 (2H, s).

(ii) [3-{2-chloro-4-[(3-fluorobenzyl)sulfonyl]phenoxy}-5-(trifluoromethyl)phenyl]acetic acid The title compound was prepared as described in example 2 step (iii) but instead using the product from example 25 step (iv) and the product from step (i).

1H NMR DMSO-d6: δ 7.75 (1H, m), 7.68-6.97 (9H, m), 4.81 (2H, s), 3.65 (2H, s).

MS: APCI-ve 501 (M-H).

EXAMPLE 65

{3-bromo-5-[2-fluoro-4-(phenylsulfonyl)phenoxy]phenyl}acetic acid

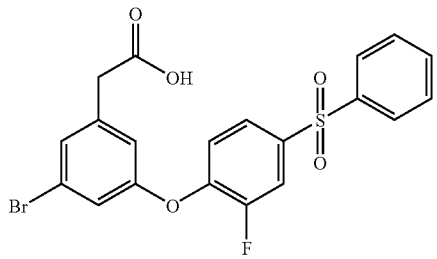

The title compound was prepared as described in example 2 step (iii) but instead using the product from example 55 step (v) and the product from example 24 step (i).

1H NMR DMSO-d6: 8.05-7.99 (3H, m), 7.80-7.62 (4H, m), 7.32 (1H, s), 7.21-7.17 (2H, m), 7.02 (1H, s), 3.35 (2H, s).

MS: APCI−ve 419 (M−CO$_2$).

EXAMPLE 66

[3-{2-fluoro-4-[(4-fluorophenyl)sulfonyl]phenoxy}-5-trifluoromethyl)phenyl]acetic acid

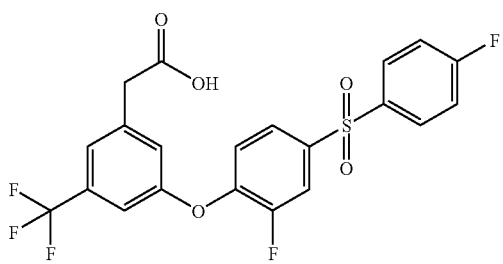

(i) 1,2-difluoro-4-[(4-fluorophenyl)sulfonyl]benzene

The title compound was prepared as described in example 29 step (i) but instead using 3,4-difluorosulfonyl chloride and fluorobenzene.

1H NMR CDCl3: δ 7.98-7.93 (2H, m), 7.78-7.70 (2H, m), 7.36-7.19 (3H, m).

(ii) [3-{2-fluoro-4-[(4-fluorophenyl)sulfonyl]phenoxy}-5-(trifluoromethyl)phenyl]acetic acid The title compound was prepared as described in example 2 step (iii) but instead using the product from example 25 step (iv) and the product from step (i).

1H NMR DMSO-d6: δ 8.12-8.08 (3H, m), 7.82-7.80 (1H, d), 7.53-7.44 (4H, m), 7.37 (1H, s), 7.27-7.23 (1H, t), 3.71 (2H, s).

MS: APCI−ve 471 (M−H).

EXAMPLE 67

{3-chloro-5-[4-(ethylsulfonyl)-3-(trifluoromethyl)phenoxy]phenyl}acetic acid

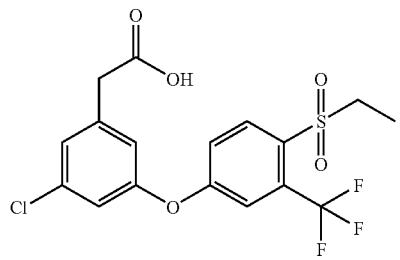

(i) 4-bromo-1-(ethylsulfonyl)-2-(trifluoromethyl)benzene

4-Bromo-1-(ethylthio)-2-(trifluoromethyl)benzene (3.80 g) was dissolved in DCM (50 ml) and MCPBA (5.71 g) added and stirred at RT overnight. The solution was then washed with aqueous sodium metabisulphite and aqueous sodium hydrogen carbonate, dried (MgSO$_4$) and evaporated under reduced pressure to give a solid, which was purified by flash column chromatography (eluent 1:1 isohexane/DCM) to give the subtitle compound (4.10 g).

1H NMR CDCl3: δ 8.13-7.87 (3H, m), 3.31-3.24 (2H, q), 1.34-1.26 (3H, t).

(ii) {3-chloro-5-[4-(ethylsulfonyl)-3-(trifluoromethyl)phenoxy]phenyl}acetic acid The title compound was prepared as described in example 2 step (iii) but instead using the product from example 18 step (iv) and the product from step (i).

1H NMR DMSO-d6: δ 8.16-8.14 (1H, d), 7.63-7.62 (1H, s), 7.41-7.38 (1H, d), 7.29-7.12 (3H, m), 3.59 (2H, s), 3.42-3.31 (2H, q), 1.18-1.14 (3H, t).

MS: APCI−ve 377 (M−CO$_2$).

EXAMPLE 68

{3-chloro-5-[5-chloro-2-fluoro-4-(pyrrolidin-1-ylcarbonyl)phenoxy]phenyl}acetic acid

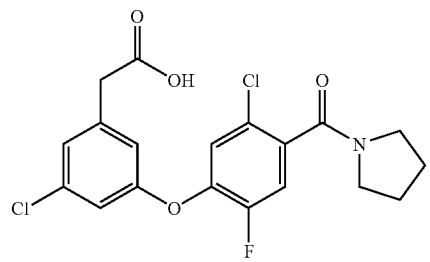

(i) 1-(2-chloro-4,5-difluorobenzoyl)pyrrolidine 2-chloro-4,5-difluorobenzoic acid (1.0 g) in DCM (10 ml) was treated with oxalyl chloride (0.45 ml) followed by a drop of DMF. The mixture was stirred at RT for 1 h before evaporating under reduced pressure. The solid was dissolved in DCM (20 ml) and pyrrolidine (2 ml) was added and stirred at RT overnight. The mixture was diluted with water, extracted with DCM, dried (MgSO$_4$) and evaporated under reduced pressure to give an oil (1.45 g).

1H NMR CDCl3: $\delta$ 7.27-7.23 (1H, m), 7.19-7.15 (1H, m), 3.66-3.62 (2H, t), 3.23-3.20 (2H, t), 2.05-1.88 (4H, m).

(ii) {3-chloro-5-[5-chloro-2-fluoro-4-(pyrrolidin-1-ylcarbonyl)phenoxy]phenyl}acetic acid The title compound was prepared as described in example 2 step (iii) but instead using the product from example 18 step (iv) and the product from step (i).

1H NMR DMSO-d6: $\delta$ 7.59-7.56 (1H, d), 7.40-7.38 (1H, d), 7.14 (1H, s), 7.02-7.01 (1H, s), 6.94 (1H, s), 3.44 (4H, m), 3.19-3.15 (2H, t), 1.90-1.81 (4H, m).

MS: APCI+ve 412 (M+H).

EXAMPLE 69

{3-cyano-5-[2-fluoro-4-(phenylsulfonyl)phenoxy]phenyl}acetic acid

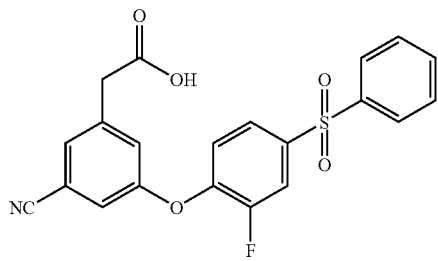

(i) {3-bromo-5-[2-fluoro-4-(phenylsulfonyl)phenoxy]phenyl}acetic acid

The subtitle compound was prepared as described in example 56 step (ii) but instead using the product of example 56 step (i) and example 24 step (i). The product was used crude without further characterisation.

(ii) {3-cyano-5-[2-fluoro-4-(phenylsulfonyl)phenoxy]phenyl}acetic acid

The title compound was prepared as described in example 56 step (iii) but instead using zinc cyanide and the product from step (i).

1H NMR DMSO-d6: 8.08-8.00 (3H, m), 7.80-7.55 (6H, m), 7.34 (1H, s), 7.29-7.18 (1H, t), 3.53 (2H, s).

MS: APCI-ve 366 (M-CO$_2$).

EXAMPLE 70

(3-chloro-5-{2-fluoro-4-[(4-fluorophenyl)sulfonyl]phenoxy}phenyl)acetic acid

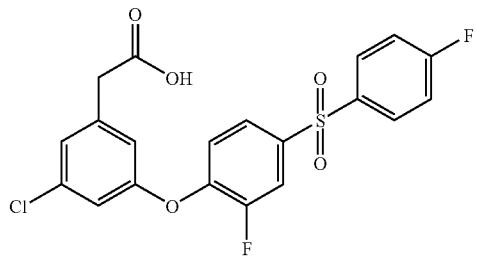

The title compound was prepared as described in example 2 step (iii) but instead using the product from example 18 step (iv) and the product from example 66 step (i).

1H NMR DMSO-d6: $\delta$ 8.10-8.00 (3H, m), 7.80-7.78 (1H, d), 7.50-7.46 (2H, t), 7.24-7.02 (2H, m), 6.87 & 6.82 (2H, 2×s), 3.41-3.39 (2H, s).

MS: APCI-ve 437 (M-H).

EXAMPLE 71

(3-chloro-5-{[2-cyano-4-(ethylsulfonyl)phenyl]thio}phenyl)acetic acid

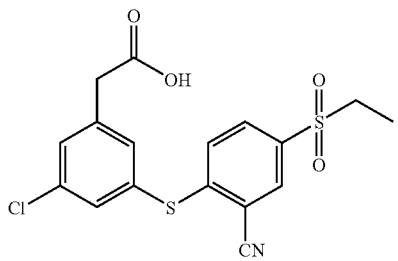

(i) (3-chloro-5-mercaptophenyl)acetic acid

The subtitle compound was prepared as described in example 58 steps (i) to (iii) but instead using the product from example 18 step (iv).

1H NMR CDCl3-: $\delta$ 7.32-7.31 (1H, s), 7.26 (1H, s), 7.08-7.07 (1H, s), 3.56 (2H, s), 2.9 (1H, s).

(ii) (3-chloro-5-{[2-cyano-4-(ethylsulfonyl)phenyl]thio}phenyl)acetic acid

The title compound was prepared as described in example 2 step (iii) but instead using the product from step (i) and the product from example 12 step (i).

1H NMR DMSO-d6: $\delta$ 8.36 (1H, s), 8.02-7.99 (1H, m), 7.59-7.48 (3H, m), 7.25-7.22 (1H, m), 3.54 (2H, s), 3.40 (2H, q), 1.13-1.08 (3H, t).

MS: APCI-ve 394 (M-H).

EXAMPLE 72

(3-chloro-5-{[4-(ethylsulfonyl)-2-(trifluoromethyl)phenyl]thio}phenyl)acetic acid

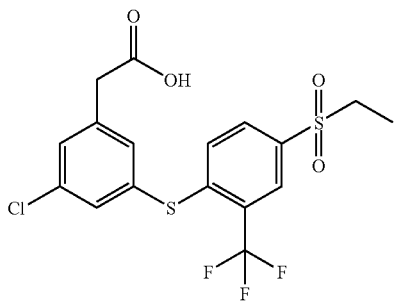

The title compound was prepared as described in example 2 step (iii) but instead using the product from example 71 step (i) and the product from example 2 step (ii).

1H NMR DMSO-d6: δ 12.53 (1H, bs), 8.21-8.20 (1H, s), 8.07-8.04 (1H, d), 7.57-7.53 (2H, m), 7.47 (1H, s), 7.34-7.32 (1H, d), 3.69 (2H, s), 3.30 (3H, s).

MS: APCI−ve 379 (N—CO₂).

EXAMPLE 73

(3-chloro-5-{[2-fluoro-4-(phenylsulfonyl)phenyl]thio}phenyl)acetic acid

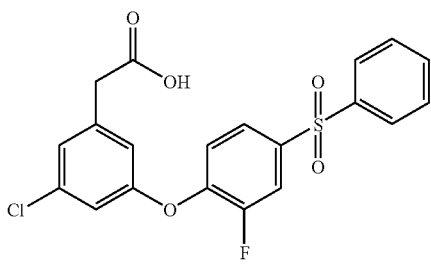

The title compound was prepared as described in example 1 step vi) but instead using the product from example 71 step (i) and the product from example 24 step (i).

1H NMR DMSO-d6: δ 12.51 (1H, s), 8.00-7.91 (3H, m), 7.73-7.60 (4H, m), 7.49-7.29 (3H, m), 7.24-7.18 (1H, t), 3.65 (2H, s).

MS: APCI−ve 435 (M−H).

EXAMPLE 74

[3-(4-benzoyl-3,5-difluorophenoxy)-5-chlorophenyl]acetic acid

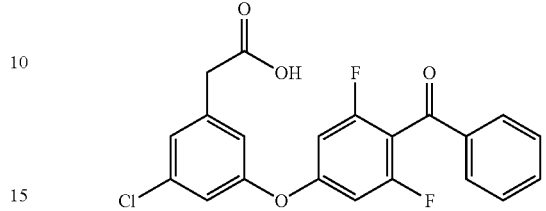

(i) phenyl(2,4,6-trifluorophenyl)methanone 2,4,6-trifluorobenzoyl chloride (5.0 g), benzene (5 ml) and ferric chloride (1.39 g) were heated at 80° C. for 16 h, then allowed to cool to room temperature. The reaction mixture was diluted with water, extracted with ethyl acetate (×2) and the combined organic extracts washed with brine, dried (MgSO₄) and evaporated under reduced pressure (5.80 g).

1H NMR CDCl3: δ 7.86-7.84 (2H, m), 7.66-7.61 (1H, m), 7.52-7.47 (2H, m), 6.81-6.74 (2H, m).

(ii) [3-(4-benzoyl-3,5-difluorophenoxy)-5-chlorophenyl]acetic acid

The title compound was prepared as described in example 2 step (iii) but instead using the product from example 18 step (iv) and the product from step (i).

1H NMR DMSO-d6: δ 7.87-7.68 (3H, m), 7.62-7.55 (2H, t), 7.26-7.24 (2H, m), 7.13-7.12 (1H, s), 7.01-6.92 (2H, d), 3.62 (2H, s).

MS: APCI+ve 357 (M-CO₂).

EXAMPLE 75

{3-chloro-5-[2-chloro-4-(4-fluorobenzoyl)phenoxy]phenyl}acetic acid

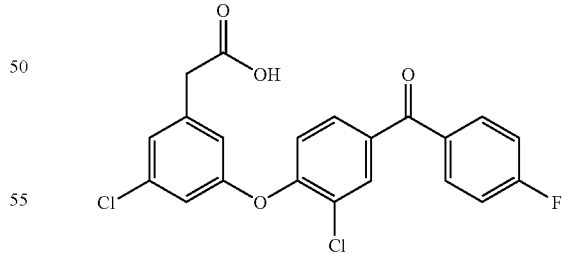

(i) (3-chloro-4-fluorophenyl)(4-fluorophenyl)methanone

The subtitle compound was prepared as described in example 74 step (i) but instead using 3-chloro-4-fluorobenzoyl chloride and fluorobenzene.

1H NMR CDCl3-d6: δ 7.88-7.78 (3H, m), 7.57-7.53 (1H, m), 7.29-7.15 (3H, m).

(ii) {3-chloro-5-[2-chloro-4-(4-fluorobenzoyl)phenoxy]phenyl}acetic acid

The title compound was prepared as described in example 2 step (iii) but instead using the is product from example 18 step (iv) and the product from step (i).

1H NMR DMSO-d6: δ 7.92-7.84 (3H, m), 7.72-7.69 (1H, d), 7.44-7.39 (2H, m), 7.21-7.17 (2H, m), 7.10-7.08 (1H, m), 7.00 (1H, s), 3.55 (2H, s).
MS: APCI+ve 373 (M-CO$_2$).

EXAMPLE 76

{3-[2-fluoro-4-(Phenylsulfonyl)phenoxy]-5-methylphenyl}acetic acid

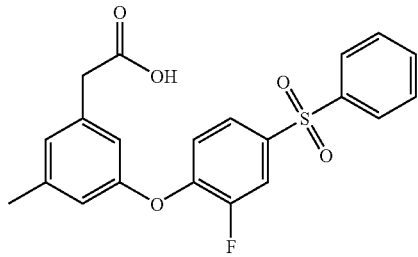

(i) {3-[2-fluoro-4-(phenylsulfonyl)phenoxy]-5-hydroxyphenyl}acetic acid

The subtitle compound was prepared as described in example 2 step (iii) but instead using 3,5-dihydroxyphenylacetic acid and the product from example 24 step (i).
MS: APCI-ve 415 (M-H).

(ii) (3-[2-fluoro-4-(phenylsulfonyl)phenoxy]-5-{[(trifluoromethyl)sulfonyl]oxy}phenyl)acetic acid The product from step (i) (4.16 g) in dry DCM (20 ml) was treated with pyridine (0.81 ml) and cooled to 0° C. before adding trifluoromethanesulphonic anhydride (1.68 ml). The mixture was stirred at RT overnight and then diluted with water, extracted with DCM, dried (MgSO$_4$) and evaporated under reduced pressure (2.09 g).

1H NMR CDCl3-d6: δ 7.97-7.95 (2H, d), 7.80-7.72 (2H, m), 7.65-7.52 (3H, m), 7.18-7.10 (1H, t), 7.05-6.85 (3H, s), 3.71 (3H, s), 3.63 (2H, s).

(iii) {3-[2-fluoro-4-(phenylsulfonyl)phenoxy]-5-methylphenyl}acetic acid

The title compound was prepared by treating the product from step (ii) (0.25 g) in dry dioxane (10 ml) with bisdiphenylphosphinoferrocene palladium (0.02 g) and 2.0M dimethylzinc in toluene (0.40 ml). The mixture was heated to reflux for 3 h, partitioned between water and ethyl acetate, the organics separated, dried (MgSO$_4$) and evaporated under reduced pressure to an oil. The oil was dissolved in methanol (10 ml), 2M NaOH (10 ml) added and stirred at RT overnight. The mixture was diluted with water, extracted with ether (discarded). The aqueous layer was acidified with 2M HCl, extracted with ethyl acetate, dried (MgSO$_4$) and evaporated under reduced pressure to an oil, which was purified by RPHPLC to give a white solid (0.085 g).

1H NMR DMSO-d6: δ 8.03-7.97 (3H, m), 7.77-7.60 (4H, m), 7.13-7.07 (1H, t), 6.94 (1H, s), 6.81 (2H, s), 3.34 (2H, s), 2.26 (3H, s).
MS: APCI-ve 355 (M-CO$_2$).

EXAMPLE 77

{3-ethyl-5-[2-fluoro-4-(phenylsulfonyl)phenoxy]phenyl}acetic acid

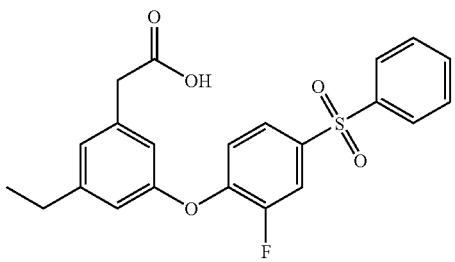

The title compound was prepared as described in example 76 step (iii) but instead using the product of example 76 step (ii) and 2.0M diethylzinc in toluene.

1H NMR DMSO-d6: δ 8.04-7.97 (3H, m), 7.78-7.60 (4H, m), 7.12-7.07 (1H, t), 6.98 (1H, s), 6.86-6.84 (2H, d), 3.48 (2H, s), 2.61-2.51 (2H, q), 1.17-1.12 (3H, t).
MS: APCI-ve 369 (M-CO$_2$).

EXAMPLE 78

[3-{2-chloro-4-[(4-fluorobenzyl)sulfonyl]phenoxy}-5-(trifluoromethyl)phenyl]acetic acid

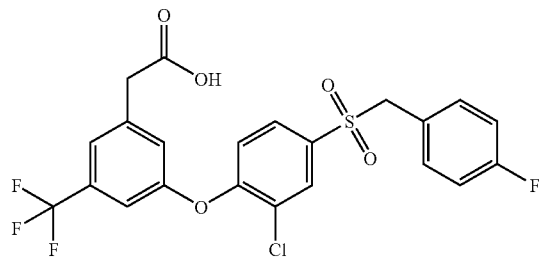

The title compound was prepared as described in example 2 step (iii) but instead using the product from example 25 step (iv) and the product from example 34 step (i).

$^1$H NMR DMSO-d6: δ 7.92 (1H, d), 7.61 (1H, dd), 7.55 (1H, s), 7.35 (2H, d), 7.27-7.13 (5H, m), 4.77 (2H, s), 3.76 (2H, s).
MS: MM-ve 501 (M-H).

EXAMPLE 79

[3-[2-cyano-4-(phenylsulfonyl)phenoxy]-5-(trifluoromethyl)phenyl]acetic acid

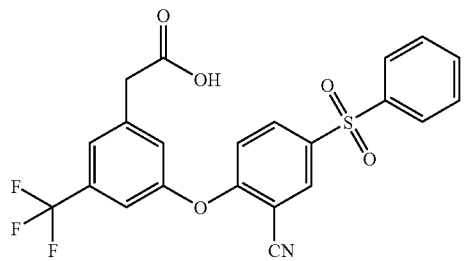

The title compound was prepared as described in example 2 step (iii) but instead using the product from example 25 step (iv) and the product from example 44 step (i).

1H NMR DMSO-d6: δ 12.57 (1H, s), 8.62 (1H, d), 8.17 (1H, dd), 8.03 (2H, dt), 7.76-7.61 (5H, m), 7.54 (1H, s), 7.04 (1H, d), 3.77 (2H, s).

MS: MM−ve 416 (M-CO₂).

EXAMPLE 80

{5-[2-chloro-4-(ethylsulfonyl)phenoxy]biphenyl-3-yl}acetic acid

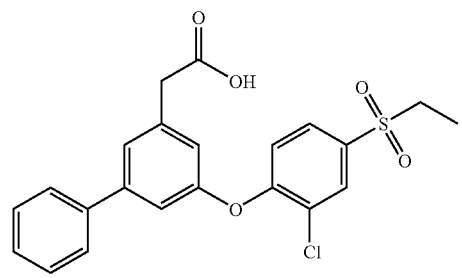

The product from example 55 step (vi) (0.45 g), phenyl boronic acid (0.190 g), sodium carbonate (0.44 g) and bis-diphenylphosphinoferrocene palladium (II) (0.04 g) in dry dioxane (20 ml) were heated to 80° C. for 20 h. Mixture diluted with 2M HCl, extracted with ethyl acetate, dried (MgSO₄) and evaporated under reduced pressure to an oil, which was purified by RPHPLC to give a cream solid (0.23 g).

1H NMR DMSO-d6: δ 8.07 (1H, s), 7.82-7.79 (1H, d), 7.69-7.66 (2H, d), 7.50-7.35 (5H, m), 7.18-7.06 (2H, m), 3.69 (2H, s), 3.39-3.31 (2H, q), 1.14-1.09 (3H, t).

MS: MM−ve 385 (M-CO₂).

EXAMPLE 81

{3-[2-chloro-4-(ethylsulfonyl)phenoxy]-5-pyridin-2-ylphenyl}acetic acid

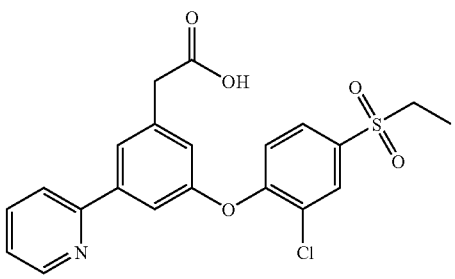

The product from example 55 step (vi) (0.45 g), 2-pyridyl zinc bromide (0.89 ml) and bisdiphenylphosphinoferrocene palladium (II) (0.04 g) in dry dioxane (20 ml) were heated to 90° C. for 20 h. Mixture diluted with water, extracted with DCM, dried (MgSO₄) and evaporated under reduced pressure to an oil, which was purified by RPHPLC to give a white solid (3 mg).

1H NMR DMSO-d6: δ 8.65-8.64 (1H, m), 8.09-7.72 (6H, m), 7.39-7.36 (1H, m), 7.19-7.15 (2H, m), 3.66 (2H, s), 3.39-3.35 (2H, q), 1.14-1.10 (3H, t).

MS: MM+ve 432 (M+H).

EXAMPLE 82

{3-[2-chloro-4-(ethylsulfonyl)phenoxy]-5-[2-(dimethylamino)ethoxy]phenyl}acetic acid

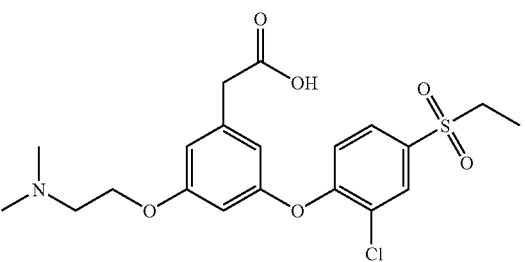

(i) methyl{3-[2-chloro-4-(ethylsulfonyl)phenoxy]-5-hydroxyphenyl}acetate

Methyl-3,5-dihydroxyphenyl acetate (0.20 g), cesium carbonate (1.08 g) and the product from example 3 step (i) in dry NMP were heated at 50° C. for 4 h. 2M HCl was added and extracted with ethyl acetate. The organics were dried (MgSO₄) and evaporated under reduced pressure to a brown oil, which was purified by flash column chromatography (eluent 1:1 ethyl acetate/isohexane) to give a mixture of the mono- and bis-coupled products used in the next step without further purification.

MS: MM−ve 383 (M−H).

(ii) methyl{3-[2-chloro-4-(ethylsulfonyl)phenoxy]-5-[2-(dimethylamino)ethoxy]phenyl}acetate Potassium carbonate (0.46 g) was added to a solution of the product from step (i) (1.10 mmol) and 2-dimethylamino ethyl chloride hydrochloride (0.16 g) in DMF at RT. After 1 h no reaction was evident so the mixture was heated to 60° C. for 18 h. Water was added and the mixture extracted with ethyl acetate, washed (brine) and the organics dried ($MgSO_4$) and concentrated to a green oil which was purified by flash column chromatography (eluent 1% triethylamine and 2% methanol in ethyl acetate) to give the subtitle compound as a coulourless oil (100 mg).
MS: MM+ve 456 (4+H).

(iii) {3-[2-chloro-4-(ethylsulfonyl)phenoxy]-5-[2-(dimethylamino)ethoxy]phenyl}acetic acid 1M sodium hydroxide (0.44 ml) was added to a solution of the product from step (ii) (100 mg) in 1:1 THF/methanol (6 ml) and stirred for 48 h. The mixture was evaporated under reduced pressure and purified by RPHPLC to give the title compound as a white solid (0.04 g).
1H NMR MeOD: δ 8.00 (1H, d), 7.75 (1H, dd), 7.41 (1H, d), 6.87 (1H, s), 6.69 (1H, s), 6.59 (1H, t), 4.27 (2H, t), 3.46 (2H, s), 3.34 (2H, t), 3.22 (2H, q), 2.79 (6H, s), 1.23 (3H, t).
MS: MM+ve 442 (M+H).

EXAMPLE 83

[3-{2-chloro-4-[(pyridin-2-ylmethyl)sulfonyl]phenoxy}-5-(trifluoromethyl)phenyl]acetic acid

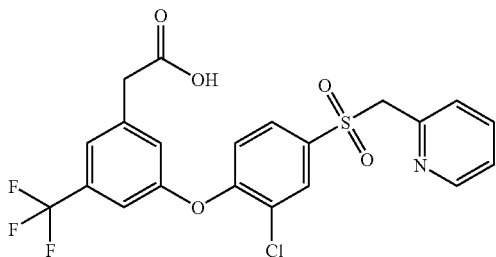

(i) 2-{[(3-chloro-4-fluorophenyl)thio]methyl}pyridine

2-Picolyl chloride hydrochloride (3.03 g) was added to a stirred suspension of 3-chloro-4-fluorobenzenethiol (3.0 g) and cesium carbonate (12.0 g) in DMF (50 ml) and the mixture stirred at RT overnight. Mixture poured into water, organics extracted into ether and the ether extracts washed (brine), dried ($MgSO_4$) and evaporated under reduced pressure to a green oil (4.0 g).
$^1$H NMR DMSO-d6: δ 8.48 (1H, d), 7.74 (1H, td), 7.62-7.58 (1H, m), 7.43-7.32 (3H, m), 7.26 (1H, ddd), 4.36 (2H, s).

(ii) 2-{[(3-chloro-4-fluorophenyl)sulfonyl]methyl}pyridine

TFA (0.59 ml) was added to a solution of the product from step (i) (2.0 g) in DCM (50 ml). MCPBA (6.6 g) was then added portionwise to the solution followed by further DCM (20 ml). The mixture was stirred at RT for 2 h then DCM added (150 ml) and the mixture washed with aqueous sodium hydrogen carbonate then brine. The organics were dried ($MgSO_4$) and evaporated under reduced pressure and the residue purified by flash column chromatography (eluent 1:1 i-hexane/ethyl acetate to 10% ethanol/DCM) to give the product (1.3 g) as a white solid.
1H NMR DMSO-d6: δ 8.42 (1H, ddd), 7.92 (1H, dd), 7.81 (1H, td), 7.70-7.61 (2H, m), 7.40 (1H, d), 7.34 (1H, ddd), 4.92 (2H, s).

(iii) [3-{2-chloro-4-[(pyridin-2-ylmethyl)sulfonyl]phenoxy}-5-(trifluoromethyl)phenyl]acetic acid The title compound was prepared as described in example 2 step (iii) but instead using the product from example 25 step (iv) and the product from step (ii).
1H NMR DMSO-d6: δ 8.43 (1H, dd), 7.89 (1H, d), 7.81 (1H, td), 7.61 (1H, dd), 7.55 (1H, s), 7.42 (1H, d), 7.37-7.32 (3H, m), 7.20 (1H, d), 4.91 (2H, s), 3.77 (2H, s).
MS: MM+ve 486 (M+H).

Pharmacological Data
Ligand Binding Assay

[$^3$H]$PGD_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 g/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 μg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 μl of 6.25 nM [$^3$H]$PGD_2$, 201 membrane saturated SPA beads both in assay buffer and 10 μl of compound solution or 13,14-dihydro-15-keto prostaglandin $D_2$ (DK-PGD$_2$, for determination of non-specific binding, Cayman chemical company).

Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well).

Compounds of formula (I) have an IC$_{50}$ value of less than (<) 10M. Specifically Example 7 has a pIC$_{50}$ value of 8.10, example 9 has a pIC$_{50}$ value of 7.85 and example 11 has a pIC$_{50}$ value of 8.05

The invention claimed is:

1. A compound of formula (I) or a pharmaceutically acceptable salt thereof:

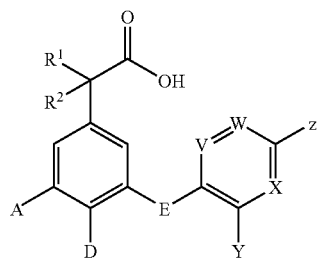

(I)

in which:
A is selected from hydrogen, halogen, CN, OR$^3$, phenyl, 6 member heteroaromatic ring containing N, or C$_{1-6}$alkyl, the latter group being optionally substituted by halogen atoms;
D is hydrogen, halogen or C$_{1-6}$alkyl, the latter group being optionally substituted by one or more halogen atoms;
E is O;
V is C(H);
W is a carbon atom substituted by hydrogen, halogen, CN, or C$_{1-3}$ alkyl (the latter group being optionally substituted by halogen atoms);
X is a carbon atom substituted by hydrogen, halogen, CN, or C$_{1-3}$ alkyl (the latter group being optionally substituted by halogen atoms);
Y is selected from hydrogen, CN, halogen or C$_{1-6}$ alkyl (the latter being optionally substituted by one or more halogen atoms);
Z is selected from SO$_2$morpholine, CONR$^4$R$^5$, COR$^6$ or SO$_2$R$^9$;
R$^1$ and R$^2$ independently represent a hydrogen atom, halogen or a C$_{1-6}$alkyl group;
R$^3$ is hydrogen or C$_{1-6}$ alkyl (optionally substituted by halogen or NR$^4$R$^5$) or;
R$^4$ and R$^5$ independently represent hydrogen or C$_{1-6}$alkyl
R$^6$ represents plenyl or pyrrolidine; and
R$^9$ represents phenyl, benzyl, methylpyridine or C$_{1-6}$alkyl, optionally substituted by one or more halogen atoms; provided that:
A and D cannot both be hydrogen;
A cannot be aryl substituted in the para-position by —S(O)$_n$—, where n is 0, 1 or 2; and
when V, W and X are all carbon then all of the substituents on the phenyl ring (V, W, X, Y and Z) cannot be hydrogen.

2. A compound according to claim 1 in which A is hydrogen, halogen or C$_{1-6}$alkyl, the latter group being optionally substituted by one or more halogen atoms.

3. A compound according to claim 1 in which where D is not hydrogen then A is hydrogen; where A is not hydrogen then D is hydrogen.

4. A compound according to claim 1 in which W is a carbon atom substituted by hydrogen, halogen or C$_{1-3}$ alkyl (the latter group being optionally substituted by halogen atoms).

5. A compound according to claim 1 in which W is C(H).

6. A compound according to claim 1 in which X is a carbon atom substituted by hydrogen or halogen.

7. A compound according to claim 1 in which X is C(H).

8. A compound according to claim 1 in which Y is halogen, cyano or C$_{1-3}$ alkyl optionally substituted by one or more halogen atoms.

9. A compound according to claim 1 in which R$^1$ and R$^2$ are both hydrogen, or one of R$^1$ or R$^2$ is methyl and the other is hydrogen.

10. A compound of formula (I) selected from the group consisting of:
{4-chloro-3-[2-chloro-4-(methylsulfonyl)phenoxy] phenyl}acetic acid;
{4-chloro-3-[4-(methylsulfonyl)-2-(trifluoromethyl)phenoxy]phenyl}acetic acid;
{4-chloro-3-[2-chloro-4-(ethylsulfonyl)phenoxy] phenyl}acetic acid;
{4-chloro-3-[4-(ethylsulfonyl)-2-(trifluoromethyl)phenoxy]phenyl}acetic acid;
{4-chloro-3-[4-(methylsulfonyl)phenoxy]phenyl}acetic acid;
2-{4-chloro-3-[2-chloro-4-(methylsulfonyl)phenoxy] phenyl}propanoic acid;
{4-chloro-3-[2-fluoro-4-(methylsulfonyl)phenoxy] phenyl}acetic acid;
{4-chloro-3-[4-(ethylsulfonyl)-2-fluorophenoxy] phenyl}acetic acid;
{4-chloro-3-[2-cyano-4-(methylsulfonyl)phenoxy] phenyl}acetic acid;
{4-chloro-3-[2-cyano-4-(ethylsulfonyl)phenoxy] phenyl}acetic acid;
{4-chloro-3-[4-(methylsulfonyl)-3-(trifluoromethyl)phenoxy]phenyl}acetic acid;
(4-chloro-3-{2-fluoro-4-[(4-fluorobenzyl)sulfonyl] phenoxy}phenyl)acetic acid;
[3-(4-benzoyl-2-fluorophenoxy)-4-chlorophenyl]acetic acid;
{3-chloro-5-[2-chloro-4-(methylsulfonyl)phenoxy] phenyl}acetic acid;
{3-chloro-5-[2-chloro-4-(ethylsulfonyl)phenoxy] phenyl}acetic acid;
{3-[2-chloro-4-(ethylsulfonyl)phenoxy]-5-fluorophenyl}acetic acid;
{3-fluoro-5-[4-(methylsulfonyl)-2-(trifluoromethyl)phenoxy]phenyl}acetic acid;
{3-[2-chloro-4-(ethylsulfonyl)phenoxy]-4-fluorophenyl}acetic acid;
{4-fluoro-3-[4-(methylsulfonyl)-2-(trifluoromethyl)phenoxy]phenyl}acetic acid;
{4-chloro-3-[2-fluoro-4-(phenylsulfonyl)phenoxy] phenyl}acetic acid;
[3-[2-chloro-4-(methylsulfonyl)phenoxy]-5-(trifluoromethyl)phenyl]acetic acid;
[3-[2-chloro-4-(ethylsulfonyl)phenoxy]-5-(trifluoromethyl)phenyl]acetic acid;
{3-chloro-5-[2-fluoro-4-(methylsulfonyl)phenoxy] phenyl}acetic acid;

{3-chloro-5-[2-cyano-4-(ethylsulfonyl)phenoxy]phenyl}acetic acid;
{3-chloro-5-[2-chloro-4-(phenylsulfonyl)phenoxy]phenyl}acetic acid;
{3-chloro-5-[4-(ethylsulfonyl)-2-fluorophenoxy]phenyl}acetic acid;
{3-chloro-5-[2-fluoro-4-(phenylsulfonyl)phenoxy]phenyl}acetic acid;
[3-{2-fluoro-4-[(4-fluorobenzyl)sulfonyl]phenoxy}-5-(trifluoromethyl)phenyl]acetic acid;
(3-chloro-5-{4-[(4-fluorobenzyl)sulfonyl]phenoxy}phenyl)acetic acid;
(3-chloro-5-{2-chloro-4-[(4-fluorobenzyl)sulfonyl]phenoxy}phenyl)acetic acid;
{3-chloro-5-[4-(methylsulfonyl)-2-(trifluoromethyl)phenoxy]phenyl}acetic acid;
{3-chloro-5-[4-(ethylsulfonyl)-2-(trifluoromethyl)phenoxy]phenyl}acetic acid;
[3-[2-fluoro-4-(phenylsulfonyl)phenoxy]-5-(trifluoromethyl)phenyl]acetic acid;
[3-[2-chloro-4-(phenylsulfonyl)phenoxy]-5-(trifluoromethyl)phenyl]acetic acid;
[3-[4-(ethylsulfonyl)-2-fluorophenoxy]-5-(trifluoromethyl)phenyl]acetic acid;
[3-[2-cyano-4-(ethylsulfonyl)phenoxy]-5-(trifluoromethyl)phenyl]acetic acid;
[3-[4-(ethylsulfonyl)-2-(trifluoromethyl)phenoxy]-5-(trifluoromethyl)phenyl]acetic acid;
{3-[4-(benzylsulfonyl)-2-chlorophenoxy]-5-chlorophenyl}acetic acid;
{3-chloro-5-[4-(phenylsulfonyl)-2-(trifluoromethyl)phenoxy]phenyl}acetic acid;
{3-chloro-5-[2-cyano-4-(phenylsulfonyl)phenoxy]phenyl}acetic acid;
{3-[4-(benzylsulfonyl)-2-fluorophenoxy]-5-chlorophenyl}acetic acid;
(3-chloro-5-{2-fluoro-4-[(3-fluorobenzyl)sulfonyl]phenoxy}phenyl)acetic acid;
{3-[4-(benzylsulfonyl)-2-(trifluoromethyl)phenoxy]-5-chlorophenyl}acetic acid;
(3-chloro-5-{2-fluoro-4-[(2-fluorobenzyl)sulfonyl]phenoxy}phenyl)acetic acid;
(3-chloro-5-{4-[(4-chlorobenzyl)sulfonyl]-2-fluorophenoxy}phenyl)acetic acid;
2-[3-[4-(ethylsulfonyl)-2-(trifluoromethyl)phenoxy]-5-(trifluoromethyl)phenyl]propanoic acid;
2-[3-[2-chloro-4-(ethylsulfonyl)phenoxy]-5-(trifluoromethyl)phenyl]propanoic acid;
2-[3-[2-chloro-4-(phenylsulfonyl)phenoxy]-5-(trifluoromethyl)phenyl]propanoic acid;
2-[3-{2-chloro-4-[(4-fluorobenzyl)sulfonyl]phenoxy}-5-(trifluoromethyl)phenyl]propanoic acid;
(3-chloro-5-{4-[(4-chlorobenzyl)sulfonyl]-2-fluorophenoxy}phenyl)acetic acid;
{3-bromo-5-[2-chloro-4-(ethylsulfonyl)phenoxy]phenyl}acetic acid;
{3-[2-chloro-4-(ethylsulfonyl)phenoxy]-5-methylphenyl}acetic acid;
{3-[2-chloro-4-(ethylsulfonyl)phenoxy]-5-methoxyphenyl}acetic acid;
[3-{2-chloro-4-[(2-fluorobenzyl)sulfonyl]phenoxy}-5-(trifluoromethyl)phenyl]acetic acid;
[3-[2-chloro-4-(morpholin-4-ylsulfonyl)phenoxy]-5-(trifluoromethyl)phenyl]acetic acid;
[3-(4-benzoyl-2-chlorophenoxy)-5-(trifluoromethyl)phenyl]acetic acid;
[3-{2-chloro-4-[(3-fluorobenzyl)sulfonyl]phenoxy}-5-(trifluoromethyl)phenyl]acetic acid;
{3-bromo-5-[2-fluoro-4-(phenylsulfonyl)phenoxy]phenyl}acetic acid;
[3-{2-fluoro-4-[(4-fluorophenyl)sulfonyl]phenoxy}-5-(trifluoromethyl)phenyl]acetic acid;
{3-chloro-5-[4-(ethylsulfonyl)-3-(trifluoromethyl)phenoxy]phenyl}acetic acid;
{3-chloro-5-[5-chloro-2-fluoro-4-(pyrrolidin-1-ylcarbonyl)phenoxy]phenyl}acetic acid;
{3-cyano-5-[2-fluoro-4-(phenylsulfonyl)phenoxy]phenyl}acetic acid;
(3-chloro-5-{2-fluoro-4-[(4-fluorophenyl)sulfonyl]phenoxy}phenyl)acetic acid;
[3-(4-benzoyl-3,5-difluorophenoxy)-5-chlorophenyl]acetic acid;
{3-chloro-5-[2-chloro-4-(4-fluorobenzoyl)phenoxy]phenyl}acetic acid;
{3-[2-fluoro-4-(phenylsulfonyl)phenoxy]-5-methylphenyl}acetic acid;
{3-ethyl-5-[2-fluoro-4-(phenylsulfonyl)phenoxy]phenyl}acetic acid;
[3-{2-chloro-4-[(4-fluorobenzyl)sulfonyl]phenoxy}-5-(trifluoromethyl)phenyl]acetic acid;
[3-[2-cyano-4-(phenylsulfonyl)phenoxy]-5-(trifluoromethyl)phenyl]acetic acid;
{5-[2-chloro-4-(ethylsulfonyl)phenoxy]biphenyl-3-yl}acetic acid;
{3-[2-chloro-4-(ethylsulfonyl)phenoxy]-5-pyridin-2-ylphenyl}acetic acid;
{3-[2-chloro-4-(ethylsulfonyl)phenoxy]-5-[2-(dimethylamino)ethoxy]phenyl}acetic acid; and
[3-{2-chloro-4-[(pyridin-2-ylmethyl)sulfonyl]phenoxy}-5-(trifluoromethyl)phenyl]acetic acid and pharmaceutically acceptable salts thereof.

11. Methyl 3-[2-chloro-4-(ethylsulfonyl)phenoxy]-5-cyanobenzoate or a pharmaceutically acceptable salt thereof.

12. A compound selected from the group consisting of (4-chloro-3-{2-chloro-4-[(dimethylamino)sulfonyl]phenoxy}phenyl)acetic acid, [4-chloro-3-(3-cyanophenoxy)phenyl]acetic acid, {4-chloro-3-[2-cyano-5-(trifluoromethyl)phenoxy]phenyl}acetic acid, (4-chloro-3-{2-chloro-4-[(isobutylamino)carbonyl]phenoxy}phenyl)acetic acid, and [3-{[3-methyl-5-(phenylsulfonyl)pyridin-2-yl]oxy}-5-(trifluoromethyl)phenyl] acetic acid or a pharmaceutically acceptable salt thereof.

\* \* \* \* \*